US011192938B2

(12) United States Patent
Baumeister et al.

(10) Patent No.: US 11,192,938 B2
(45) Date of Patent: *Dec. 7, 2021

(54) SERUM ALBUMIN BINDING PROTEINS CONTAINING IMMUNOGLOBULIN SINGLE VARIABLE DOMAINS

(71) Applicant: Ablynx N. V., Zwijnaarde (BE)

(72) Inventors: Judith Baumeister, Mechelen (BE); Marie-Paule Lucienne Armanda Bouche, Gentbrugge (BE); Carlo Boutton, Wielsbeke (BE); Marie-Ange Buyse, Merelbeke (BE); Veerle Snoeck, Zingem (BE); Stephanie Staelens, Wevelgem (BE); Bruno Dombrecht, Heusden (BE); Peter Schotte, De Pinte (BE); Cedric Jozef Neotere Ververken, Merelbeke (BE); Gerald Beste, Ghent (BE); Guy Hermans, Merelbeke (BE); Soren Steffensen, Etterbeek (BE); Alexander Szyroki, Oldenburg (DE); Tinneke Denayer, De Pinte (BE)

(73) Assignee: Ablynx N.V., Zwijnaarde (BE)

( * ) Notice: Subject to any disclaimer, the term of this patent is extended or adjusted under 35 U.S.C. 154(b) by 0 days.

This patent is subject to a terminal disclaimer.

(21) Appl. No.: 15/615,281

(22) Filed: Jun. 6, 2017

(65) Prior Publication Data
US 2017/0275361 A1   Sep. 28, 2017

Related U.S. Application Data

(63) Continuation of application No. 14/128,681, filed as application No. PCT/EP2012/062251 on Jun. 25, 2012.

(60) Provisional application No. 61/541,368, filed on Sep. 30, 2011, provisional application No. 61/500,360, filed on Jun. 23, 2011, provisional application No. 61/500,464, filed on Jun. 23, 2011.

(51) Int. Cl.
| | | |
|---|---|---|
| *C07K 16/00* | (2006.01) | |
| *C07K 16/18* | (2006.01) | |
| *A61K 39/00* | (2006.01) | |
| *A61K 39/395* | (2006.01) | |
| *C07K 16/28* | (2006.01) | |
| *C07K 16/42* | (2006.01) | |
| *G01N 33/53* | (2006.01) | |
| *G01N 33/543* | (2006.01) | |
| *G01N 33/68* | (2006.01) | |

(52) U.S. Cl.
CPC ............ *C07K 16/00* (2013.01); *C07K 16/18* (2013.01); *A61K 39/39533* (2013.01); *A61K 2039/505* (2013.01); *C07K 16/28* (2013.01); *C07K 16/2875* (2013.01); *C07K 16/42* (2013.01); *C07K 16/4283* (2013.01); *C07K 2317/22* (2013.01); *C07K 2317/31* (2013.01); *C07K 2317/34* (2013.01); *C07K 2317/35* (2013.01); *C07K 2317/567* (2013.01); *C07K 2317/569* (2013.01); *C07K 2317/92* (2013.01); *C07K 2317/94* (2013.01); *C07K 2319/30* (2013.01); *G01N 33/5306* (2013.01); *G01N 33/54393* (2013.01); *G01N 33/6854* (2013.01); *G01N 33/6857* (2013.01)

(58) Field of Classification Search
None
See application file for complete search history.

(56) References Cited

U.S. PATENT DOCUMENTS

| | | | |
|---|---|---|---|
| 4,108,837 A | 8/1978 | Johnson et al. | |
| 5,608,039 A | 3/1997 | Pastan et al. | |
| 7,622,259 B1 * | 11/2009 | Cauwenberghs | G01N 33/86 435/7.1 |
| 7,741,273 B2 | 6/2010 | McKay | |
| 7,807,162 B2 | 10/2010 | Silence | |
| 7,867,497 B2 | 1/2011 | Crowe, Jr. | |

(Continued)

FOREIGN PATENT DOCUMENTS

| | | |
|---|---|---|
| CA | 2842099 A1 | 1/2013 |
| CA | 2874498 A1 | 11/2013 |

(Continued)

OTHER PUBLICATIONS

Keller et al., Glia, 57:1130-1142 (2009).*
Checkhonin et al., Doklady Biochemistry and Biophysics, 2008, vol. 418, pp. 40-43. Original Russian Text published in Doklady Akademii Nauk, 2008, vol. 418, No. 5, pp. 697-700.*
Rungger-Brandle et al., Invest Ophthalmol Vis Sci., 41:1971-1980, 2000.*
U.S. Appl. No. 15/615,197, filed Jun. 6, 2017, Baumeister et al.
PCT/EP2011/067132, dated Dec. 22, 2011, International Search Report.

(Continued)

*Primary Examiner* — Marianne P Allen
(74) *Attorney, Agent, or Firm* — Wolf, Greenfield & Sacks, P.C.

(57) ABSTRACT

This invention provides, and in certain specific but non-limiting aspects relates to: assays that can be used to predict whether a given ISV will be subject to protein interference and/or give rise to an (aspecific) signal in such an assay (such as in an ADA immunoassay; methods for modifying and/or improving ISV's to as to remove or reduce their tendency to give rise to such protein interference or such a signal; modifications that can be introduced into an ISV that remove or reduce its tendency to give rise to such protein interference or such a signal; ISV's that have been specifically selected (for example, using the assay(s) described herein) to have no or low(er)/reduced tendency to give rise to such protein interference or such a signal; modified and/or improved ISV's that have no or a low(er)/reduced tendency to give rise to such protein interference or such a signal.

35 Claims, 20 Drawing Sheets

Specification includes a Sequence Listing.

(56) References Cited

U.S. PATENT DOCUMENTS

| | | | |
|---|---|---|---|
| 8,337,845 B2 | 12/2012 | Park et al. | |
| 8,372,808 B2 | 2/2013 | Messing et al. | |
| 8,460,888 B2 | 6/2013 | Lafaye et al. | |
| 8,614,548 B2 | 12/2013 | Huffer et al. | |
| 8,703,135 B2 | 4/2014 | Beste et al. | |
| 8,906,680 B2 | 12/2014 | Blanchetot et al. | |
| 8,907,065 B2 | 12/2014 | Hermans et al. | |
| 8,937,164 B2 * | 1/2015 | Descamps | C07K 16/2866 530/350 |
| 8,940,298 B2 | 1/2015 | Wu et al. | |
| 8,962,807 B2 * | 2/2015 | Verdonck | A61P 11/06 530/387.3 |
| 9,328,174 B2 | 5/2016 | Brown et al. | |
| 9,346,884 B2 | 5/2016 | Beste et al. | |
| 9,573,992 B2 | 2/2017 | Dombrecht et al. | |
| 9,683,045 B2 | 6/2017 | Beste et al. | |
| 9,745,372 B2 | 8/2017 | Buyse et al. | |
| 10,118,967 B2 * | 11/2018 | Hoefman | A61P 19/02 |
| 10,323,090 B2 | 6/2019 | Bowman et al. | |
| 10,501,542 B2 | 12/2019 | Punnonen et al. | |
| 10,544,222 B2 | 1/2020 | Punnonen et al. | |
| 10,544,211 B2 | 7/2020 | Buyse et al. | |
| 10,858,418 B2 | 12/2020 | Baumeister et al. | |
| 2007/0079391 A1 | 4/2007 | Yamaguchi | |
| 2008/0057063 A1 | 3/2008 | Rinkenberger et al. | |
| 2010/0022452 A1 | 1/2010 | Silence | |
| 2012/0244164 A1 | 9/2012 | Beste et al. | |
| 2013/0109842 A1 * | 5/2013 | De Brabandere | C07K 16/46 530/387.3 |
| 2013/0187539 A1 | 7/2013 | Huffer et al. | |
| 2014/0199295 A1 | 7/2014 | Baumeister et al. | |
| 2014/0205597 A1 | 7/2014 | Baumeister et al. | |
| 2014/0228546 A1 | 8/2014 | Dombrecht et al. | |
| 2014/0294847 A1 | 10/2014 | Beste et al. | |
| 2014/0341903 A1 | 11/2014 | Beste et al. | |
| 2015/0050266 A9 | 2/2015 | Baumeister et al. | |
| 2015/0307612 A9 | 10/2015 | Beste et al. | |
| 2015/0344568 A1 | 12/2015 | Baumeister et al. | |
| 2016/0009816 A1 | 1/2016 | Ritter et al. | |
| 2017/0121399 A1 | 5/2017 | Buyse et al. | |
| 2017/0137520 A1 | 5/2017 | Punnonen et al. | |
| 2017/0137521 A1 | 5/2017 | Punnonen et al. | |
| 2017/0210789 A1 | 7/2017 | Dombrecht et al. | |
| 2017/0275360 A1 | 9/2017 | Baumeister et al. | |
| 2018/0009888 A9 | 1/2018 | Baumeister et al. | |
| 2018/0355031 A1 | 12/2018 | Baumeister et al. | |
| 2019/0085096 A1 * | 3/2019 | Lenting | C12N 15/62 |
| 2019/0330339 A1 | 10/2019 | Bowman et al. | |
| 2019/0330340 A1 | 10/2019 | Bowman et al. | |
| 2019/0338025 A1 | 11/2019 | Bowman et al. | |
| 2020/0216532 A1 | 7/2020 | Baumeister et al. | |
| 2020/0325221 A1 | 10/2020 | Baumeister et al. | |

FOREIGN PATENT DOCUMENTS

| | | |
|---|---|---|
| CN | 101553505 A | 10/2009 |
| CN | 101611056 A | 12/2009 |
| GB | 1121226.3 | 12/2011 |
| JP | H06502526 A | 3/1994 |
| JP | 2008-539772 | 11/2008 |
| JP | 2010-505435 | 2/2010 |
| JP | 2010-518062 | 5/2010 |
| JP | 2011-522091 A | 7/2011 |
| JP | 2014-504866 A | 2/2014 |
| JP | 2014-520129 A | 8/2014 |
| RU | 2357974 C2 | 6/2009 |
| RU | 2007142444 A | 6/2009 |
| WO | WO 2004/041862 A2 | 5/2004 |
| WO | WO 2004/041865 A2 | 5/2004 |
| WO | WO 2004/044204 A2 | 5/2004 |
| WO | WO 2004/062551 A2 | 7/2004 |
| WO | WO 2004/065416 A2 | 8/2004 |
| WO | WO 2006/015371 A2 | 2/2006 |
| WO | WO 2006/122786 A2 | 11/2006 |
| WO | WO 2006/122787 A1 | 11/2006 |
| WO | WO 2006/122825 A2 | 11/2006 |
| WO | WO 2006/129828 A2 | 12/2006 |
| WO | WO 2006/129843 A2 | 12/2006 |
| WO | WO 2007/085814 A1 | 8/2007 |
| WO | WO 2007/126799 A2 | 11/2007 |
| WO | WO 2008/020079 A1 | 2/2008 |
| WO | WO 2008/028977 A2 | 3/2008 |
| WO | WO 2008/043821 A1 | 4/2008 |
| WO | WO 2008/068280 A1 | 6/2008 |
| WO | WO 2008/073300 A2 | 6/2008 |
| WO | WO 2008/096158 A2 | 8/2008 |
| WO | WO 2008/101985 A2 | 8/2008 |
| WO | WO 2008/122787 A1 | 10/2008 |
| WO | WO 2008/142164 A2 | 11/2008 |
| WO | WO 2009/007427 A2 | 1/2009 |
| WO | WO 2009/032949 A2 | 3/2009 |
| WO | WO 2009/042589 A1 | 4/2009 |
| WO | WO 2009/068627 A2 | 6/2009 |
| WO | WO 2009/068628 A1 | 6/2009 |
| WO | WO 2009/097128 A1 | 8/2009 |
| WO | WO 2009/127691 A1 | 10/2009 |
| WO | WO 2009/138519 A1 | 11/2009 |
| WO | WO 2009/147248 A2 | 12/2009 |
| WO | WO 2010/004432 A1 | 1/2010 |
| WO | WO 2010/042815 A2 | 4/2010 |
| WO | WO 2010/100135 A1 | 9/2010 |
| WO | WO 2010/108937 A2 | 9/2010 |
| WO | WO 2011/003622 A1 | 1/2011 |
| WO | WO 2011/064382 A1 | 6/2011 |
| WO | WO 2011/073954 A2 | 6/2011 |
| WO | WO 2011/075861 A1 | 6/2011 |
| WO | WO 2011/110642 A2 | 9/2011 |
| WO | WO 2012/042026 A2 | 4/2012 |
| WO | WO 2012/131035 A1 | 10/2012 |
| WO | WO 2012/131053 A1 | 10/2012 |
| WO | WO 2012/175400 A1 | 12/2012 |
| WO | WO 2012/175741 A2 | 12/2012 |
| WO | WO 2013/024059 A2 | 2/2013 |
| WO | WO 2014/111550 A1 | 7/2014 |

OTHER PUBLICATIONS

PCT/EP2011/067132, dated Apr. 11, 2013, International Preliminary Report on Patentability.
PCT/EP2012/069373, dated Jan. 14, 2013, Invitation to Pay Additional Fees.
PCT/EP2012/069373, dated Apr. 29, 2013, International Search Report and Written Opinion.
PCT/EP2012/062251, dated Dec. 18, 2012, International Search Report and Written Opinion.
PCT/EP2011/062251, dated Oct. 15, 2013, International Preliminary Report on Patentability.
PCT/EP2012/061304, dated Sep. 19, 2013, International Prelimiary Report on Patentability.
PCT/EP2012/061304, dated Sep. 5, 2012, International Search Report and Written Opinion.
[No Author Listed] Ablynx presentation. Sep. 9, 2015. P11-008-PCT-1.
[No Author Listed] Cure definition. Merriam-Webster.com Sep. 19, 2016.
[No. Author Listed] Treat definition. Merriam-Webster.com Sep. 19, 2016.
Arbabi-Ghahroudi et al., Selection and identification of single domain antibody fragments from camel heavy-chain antibodies. FEBS Lett. Sep. 15, 1997;414(3):521-6.
Birchmeier et al., Met, metastasis, motility and more. Nat Rev Mol Cell Biol. Dec. 2003;4(12):915-25.
Bottaro et al., Identification of the hepatocyte growth factor receptor as the c-met proto-oncogene product. Science. Feb. 15, 1991;251(4995):802-4.
Burgess et al., Fully human monoclonal antibodies to hepatocyte growth factor with therapeutic potential against hepatocyte growth factor/c-Met-dependent human tumors. Cancer Res. Feb. 1, 2006;66(3): 1721-9. Erratum in: Cancer Res. Jun. 1, 2006;66(11):5976.

(56) References Cited

OTHER PUBLICATIONS

Cao et al., Neutralizing monoclonal antibodies to hepatocyte growth factor/scatter factor (HGF/SF) display antitumor activity in animal models. Proc Natl Acad Sci U S A. Jun. 19, 2001;98(13):7443-8.

Conrath et al., Camel single-domain antibodies as modular building units in bispecific and bivalent antibody constructs. J Biol Chem. Mar. 9, 2001;276(10):7346-50. Epub Oct. 25, 2000.

Cooper et al., Molecular cloning of a new transforming gene from a chemically transformed human cell line. Nature. Sep. 6, 1984-11;311(5981):29-33.

Cortez-Retamozo et al., Efficient tumor targeting by single-domain antibody fragments of camels. Int J Cancer. Mar. 20, 2002;98(3):456-62.

Davies et al., 'Camelising' human antibody fragments: NMR studies on VH domains. FEBS Lett. Feb. 21, 1994;339(3):285-90.

Davies et al., Single antibody domains as small recognition units: design and in vitro antigen selection of camelized, human VH domains with improved protein stability. Protein Eng. Jun. 1996;9(6):531-7.

Deffar et al., Nanobodies—the new concept in antibody engineering. African Journal of Biotechnology. 2009;8(12):2645-2652.

European Medicines Agency, Guideline on immunogenicity assessment of monoclonal 5 antibodies intended for in vivo clinical use. Nov. 18, 2010.

Gibbs, Nanobodies. Sci Am. Aug. 2005;293(2):78-83.

Gottlin et al., Isolation of novel EGFR-specific VHH domains. J Biomol Screen. Jan. 2009;14(1):77-85. doi: 10.1177/1087057108327064.

Holliger et al., Engineered antibody fragments and the rise of single domains. Nat Biotechnol. Sep. 2005;23(9):1126-36.

Janeway et al., Immunobiology. The immune system in health and disease. Third edition. 1997;3.1-3.11.

Kakkar et al., Pharmacokinetics and safety of a fully human hepatocyte growth factor antibody, AMG 102, in cynomolgus monkeys. Pharm Res. Oct. 2007;24(10):1910-8. Epub May 23, 2007.

Keyaerts et al., Phase I Study of 68Ga-HER2-Nanobody for PET/CT Assessment of HER2 Expression in Breast Carcinoma. J Nucl Med. Jan. 2016;57(1):27-33. doi: 10.2967/jnumed.115.162024. Epub Oct. 8, 2015.

Klimov, Spontaneous emission of an atom in the presence of nanobodies. Quantum Electronics. 2001;31(7):569-586.

Lin, Pharmacokinetics of biotech drugs: peptides, proteins and monoclonal antibodies. Curr Drug Metab. Sep. 2009;10(7):661-91.

Liu et al., Targeting the c-MET signaling pathway for cancer therapy. Expert Opin Investig Drugs. Jul. 2008;17(7):997-1011.

Loyet et al., Technology comparisons for anti-therapeutic antibody and neutralizing antibody assays in the context of an anti-TNF pharmacokinetic study. J Immunol Methods. Jun. 30, 2009;345(1-2):17-28. doi: 10.1016/j.jim.2009.03.012. Epub Apr. 2, 2009.

Matsumoto et al., NK4 (HGF-antagonist/angiogenesis inhibitor) in cancer biology and therapeutics. Cancer Sci. Apr. 2003;94(4):321-7.

Mire-Sluis et al., Recommendations for the design and optimization of immunoassays used in the detection of host antibodies against biotechnology products. J Immunol Methods. Jun. 2004;289(1-2):1-16.

Muyldermans et al., Recognition of antigens by single-domain antibody fragments: the superfluous luxury of paired domains. Trends Biochem Sci. Apr. 2001;26(4):230-5.

Nguyen et al., Improved gene transfer selectivity to hepatocarcinoma cells by retrovirus vector displaying single-chain variable fragment antibody against c-Met. Cancer Gene Ther. Nov. 2003;10(11):840-9.

Nieba et al., Disrupting the hydrophobic patches at the antibody variable/constant domain interface: improved in vivo folding and physical characterization of an engineered scFv fragment. Protein Eng. Apr. 1997;10(4):435-44.

Peng et al., Clinical immunogenicity specificity assessments: a platform evaluation. J Pharm Biomed Anal. Feb. 20, 2011;54(3):629-35. doi: 10.1016/j.jpba.2010.09.035. Epub Oct. 29, 2010.

Poelmans et al., Immunogenicity monitoring during preclinical development of Nanobodies: comparing assay formats and species matrices. The AAPS Journal. vol. 12. No. S1. Jan. 1, 2010.

Ponzetto et al., A novel recognition motif for phosphatidylinositol 3-kinase binding mediates its association with the hepatocyte growth factor/scatter factor receptor. Mol Cell Biol. Aug. 1993;13(8):4600-8.

Revets et al., Nanobodies as novel agents for cancer therapy. Expert Opin Biol Ther. Jan. 2005;5(1):111-24.

Roitt et al., Immunology. Moscow, Mir. 2000;110-111.

Roovers et al., Efficient inhibition of EGFR signaling and of tumour growth by antagonistic anti-EFGR Nanobodies. Cancer Immunol Immunother. Mar. 2007;56(3):303-317.

Routledge et al., Reshaping antibodies for therapy—5. Prospects for producing non-immunogenic monoclonal antibodies. 1996. last accessed at http://www.path.cam.ac.uk/~mrc7/reshaping/index.html on Apr. 23, 2014.

Rudikoff et al., Single amino acid substitution altering antigen-binding specificity. Proc Natl Acad Sci U S A. Mar. 1982;79(6):1979-83.

Shankar et al., Recommendations for the validation of immunoassays used for detection of host antibodies against biotechnology products. J Pharm Biomed Anal. Dec. 15, 2008;48(5):1267-81. doi: 10.1016/j.jpba.2008.09.020. Epub Sep. 19, 2008.

Skottrup et al., Diagnostic evaluation of a nanobody with picomolar affinity toward the protease RgpB from Porphyromonas gingivalis. Anal Biochem. Aug. 15, 2011;415(2):158-67. doi: 10.1016/j.ab.2011.04.015. Epub Apr. 20, 2011.

Strothmeyer et al., Comparative analysis of predicted HLA binding of immunoglobulin idiotype sequences indicates T cell mediated immunosurveillance in follicular lymphoma. Blood. Sep. 9, 2010; 116(10):1734-6. doi: 10.1182/blood-2010-02-270199. Epub Jun. 3, 2010.

Subramanyam, Immunogenicity considerations for biologies. FABIAN. Presentation on Nov. 6, 2008.

Tibbitts et al., Key factors influencing ADME properties of therapeutic proteins: A need for ADME characterization in drug discovery and development. MAbs. Feb.-Mar. 2016;8(2):229-45. doi:10.1080/19420862.2015.1115937. Epub Dec. 4, 2015.

Tijink et al., Improved tumor targeting of anti-epidermal growth factor receptor Nanobodies through albumin binding: taking advantage of modular Nanobody technology. Mol Cancer Ther. Aug. 2008;7(8):2288-97. doi:10.1158/1535-7163.MCT-07-2384.

Trojan et al., Immunoglobulin framework-derived peptides function as cytotoxic T-cell epitopes commonly expressed in B-cell malignancies. Nat Med. Jun. 2000;6(6):667-72.

Xue et al., Pre-existing biotherapeutic-reactive antibodies: survey results within the American Association of Pharmaceutical Scientists. AAPS J. Jul. 2013;15(3):852-5. doi: 10.1208/s12248-013-9492-4.

Yakubke et al., Amino acids, peptides, proteins. Mir, Moscow. 1985. 465 pp. pp. 356-363.

Curriculum Vitae of Hubertus Schellekens. Jan. 6, 2016. 41 pages.

Expert Opinion on 3D Modeling of Carlo Boutton, with Curriculum Vitae attached. Mar. 20, 2018. 14 pages.

Expert Declaration of Marie-Ange Buyse with Curriculum Vitae attached. Mar. 20, 2018. 16 pages.

Declaration of Professor Guus van Dongen. Apr. 11, 2016. 6 pages.

Declaration of Professor Huub Schellekens. Oct. 7, 2017. 4 pages.

Declaration of Professor Roland Kontermann. Mar. 22, 2016. 21 pages.

Experimental Report on the reduction of binding of pre-existing antibodies in human serum resulting from various C-terminal amino acid extensions to two different ISVs having the amino acid sequence VTVSS at their C-terminus. Apr. 2016. 6 pages.

Opposition to EP 2723769 by Dr. Mathias Ricker, filed Oct. 11, 2017. 51 pages.

Opposition to EP 2723769 by Glaxo Group Limited, filed Oct. 10, 2017. 10 pages.

Response to Opposition Briefs Filed by Glaxo Group Limited and Dr. Mathias Ricker in EP 2723769, with Auxiliary Request. Mar. 23, 2018. 60 pages.

Summary of the Technical Data. Annex 1. Apr. 2016. 2 pages.

(56) References Cited

OTHER PUBLICATIONS

AFFIBODY presentation, Swedish-American Life Science Summit. Aug. 19-21, 2009. 19 pages.

Adlersberg, The immunoglobulin hinge (interdomain) region. Albert Einstein College of Medicine of Yeshiva University. Bronx, New York. La Ricerca Clin Lab. 6, 191, 1976.

Brezski et al., Human anti-IgG1 hinge autoantibodies reconstitute the effector functions of proteolytically inactivated IgGs. J Immunol. Sep. 1, 2008;181(5):3183-92.

Brezski et al., The origins, specificity, and potential biological relevance of human anti-IgG hinge autoantibodies. The Scientific World Journal. 2011;11:1153-1167.

Cordy et al., Specificity of human anti-variable heavy (VH) chain autoantibodies and impact on the design and clinical testing of a VH domain antibody antagonist of tumour necrosis factor-alpha receptor 1. Clin Exp Immunol. Nov. 2015;182(2):139-48. Epub Sep. 11, 2015.

Dennis et al., Albumin binding as a general strategy for improving the pharmacokinetics of proteins. J Biol Chem. Sep. 20, 2002;277(38):35035-43. Epub Jul. 15, 2002.

Fleischmann et al., ACR/ARHP Scientific meeting, Chicago. Nov. 9, 2011. Presentation 2630. A multiple ascending dose/proof of concept study of ATN-103.

Gorovits et al., Pre-existing antibody: biotherapeutic modality-based review. AAPS J. Mar. 2016;18(2):311-20.

Harboe et al., Properties of various anti-gamma-globulin factors in human sera. J Exp Med. Apr. 1, 1965;121:503-19.

Kontermann, Strategies to extend plasma half-lives of recombinant antibodies. Biodrugs. 2009;23(2):93-109.

Kormeier et al., Specificity of antiglobulin factors in normal human serum reacting with enzyme digested gamma-G-globulin. J Immunol. Mar. 1968;100(3):612-21.

Muyldermans, Single domain camel antibodies: current status. Reviews in Molecular Biotechnology. 2001;74:277-302.

Muyldermans et al., Sequence and structure of VH domain from naturally occurring camel heavy chain immunoglobulins lacking light chains. Protein Eng. Sep. 1994;7(9):1129-35.

O'Connor-Semmes et al., GSK2374697, a novel albumin-binding domain antibody (AlbudAb), extends systemic exposure of exendin-4: first study in humans—PK/PD and safety. Clin Pharmacol Ther. Dec. 2014;96(6):704-12. Doi: 10.1038/clpt.2014.187. Epub Sep. 19, 2014.

Osterland et al., Anti-gamma-globulin factors in human sera revealed by enzymatic splitting of anti-Rh antibodies. Vox Sang. Mar.-Apr. 1963;8:133-52.

Riechmann et al., Single domain antibodies: comparison of camel VH and camelised human VH domains. J Immunological Methods. 1999;231:25-38.

Schmidt et al., A synthetic peptide approach for elucidating the points of natural auto-antibody reactivity to proteolytic fragments of human IgG. 411-412. S. Del Valle et al. (eds.), In: Peptides for Youth: The Proceedings of the 20$^{th}$ American Peptide Symposium. Springer Science+Business Media, LLC. 2009.

Schoenfeld et al., Macroglobulin rheumatoid factors directed toward buried antigenic sites of human gamma-globulins. Vox Sang. Jul.-Aug. 1965;10(4):482-92.

Shankar et al. A risk-based bioanalytical strategy for the assessment of antibody immune responses against biological drugs. Nat Biotechnol. May 2007;25(5):555-61.

Steiner et al., Half-life extension using serum albumin-binding DARPin® domains. Protein Eng Des Sel. Sep. 1, 2017;30(9):583-591. Doi: 10.1093/protein/gzx022.

Van Schie et al., Cross-reactive and pre-existing antibodies to therapeutic antibodies—Effects on treatment and immunogenicity. Mabs. 2015;7(4):662-71.

Vincke et al., General strategy to humanize a camelid single-domain antibody and identification of a universal humanized nanobody scaffold. J Biol Chem. Jan. 30, 2009;284(5):3273-84. Doi: 10.1074/jbc.M806889200. Epub Nov. 14, 2008.

Waller et al., Further studies on the anti-globulin factors in human serum to the pepsin digested fragment of the Ri anti-Rh antibody. J Immunol. Sep. 1966;97(3):438-43.

Welschof et al., The antigen binding domain of non-idiotypic human anti-F(ab')2 autoantibodies: study of their interaction with IgG hinge region epitopes. Hum Immunol. Apr. 1999;60(4):282-90.

Xue et al., Evaluation of pre-existing antibody presence as a risk factor for posttreatment anti-drug antibody induction: analysis of human clinical study data for multiple biotherapeutics. AAPS J. Jul. 2013;15(3):893-6. doi: 10.1208/s12248-013-9497-z. Epub Jun. 13, 2013.

Adlersberg, The immunoglobulin hinge (interdomain) region. Ric Clin Lab. Jul.-Sep. 1976;6(3):191-205.

Illustration of the cloning technology of WO 2010/042815 published Apr. 15, 2010. 3 pages.

Sequence Listing of WO 2011/073954 published Jun. 23, 2011. 34 pages.

Summons to attend oral proceedings for EP Application No. 12729968.3 dated Oct. 29, 2018.

[No Author Listed], Sequence alignment between Seq ID No. 37 of the patent and "GSK1995057" of D35 (bottom line). Reference D49 submitted Mar. 29, 2019 in opposition proceedings to EP 2 723 769. 1 page.

[No Author Listed], Vobarilizumab. IUPHAR/BPS Guide to Pharmacology. Accessed Mar. 18, 2019 from <http://www.guidetopharmacology.org/>. 1 page.

Auxiliary Request 1, claims 1 to 17 (clean and marked copy) dated Mar. 2018, filed by Ablynx NV in Opposition Proceedings regarding EP 2723769. 6 pages.

Auxiliary Requests 2, 3, 4, and 5, claims 1 to 17 (clean and marked copies) dated Mar. 2019, filed by Ablynx NV in Opposition Proceedings regarding EP 2723769. 24 pages.

Boutton, Structure of VH/VL interaction region. Ablynx. Gent, Belgium. Mar. 2019. 4 pages.

Declaration of Professor Huub Schellekens. Mar. 18, 2019. 3 pages.

Singer et al., Genes and Genomes. University Science Books. Mill Valley, CA. Section 8.3: Structure and Expression of Class II Genes. 1991. pp. 478-539. pp. 63-4 of 1998 Russian publication also included which correspond to pp. 506-9 of English language publication.

Proudfoot et al., Novel anti-tumour necrosis factor receptor-1 (TNFR1) domain antibody prevents pulmonary inflammation in experimental acute lung injury. Thorax. Aug. 2018;73(8):723-730. doi:10.1136/thoraxjnl-2017-210305. Epub Jan. 29, 2018. Supplemental material included.

Sullivan, IL-6 nanobody vobarilizumab advances despite equivocal phase II data. Rheumatology News. MDedge. Jun. 25, 2017. 3 pages.

Written Submission before Oral Proceedings regarding the Opposition to EP 2723769 by Ablynx NV filed Mar. 20, 2019. 24 pages.

Written Submission before Oral Proceedings regarding the Opposition to EP 2723769 by Dr. Mathias Ricker, filed Mar. 20, 2019. 16 pages.

Written Submission before Oral Proceedings regarding the Opposition to EP 2723769 by Glaxo Group Limited, filed Mar. 19, 2019. 9 pages.

Zhu et al. Therapeutic target database update 2012: a resource for facilitating target-oriented drug discovery. Nucleic Acids Res. Jan. 2012;40(Database issue):D1128-36. doi: 10.1093/nar/gkr797. Epub Sep. 24, 2011.

Communication Pursuant to Rule 114(2) EPC: Third Party Observation for Application No. EP 20150173573, mailed Dec. 9, 2020. 64 pages.

Communication Pursuant to Rule 114(2) EPC: Third Party Observation for Application No. EP 20180162772, mailed Dec. 9, 2020. 66 pages.

Communication Pursuant to Rule 114(2) EPC: Third Party Observation for Application No. EP 20180162775, mailed Dec. 10, 2020. 13 pages.

Decanniere et al., A single-domain antibody fragment in complex with RNase A: non-canonical loop structures and nanomolar affinity

(56) References Cited

OTHER PUBLICATIONS using two CDR loops. Structure. Apr. 15, 1999;7(4):361-70. doi: 10.1016/s0969-2126(99)80049-5.

* cited by examiner

Figure 9

| SEQ ID NO | N-terminal amino acid(s) | Mutations in the C-terminal region | Sequence | Reference sequence |
|---|---|---|---|---|
| 37 | A | none | HHHHHHEVQLVESGGGLVQPGNSLRLSCAASGFTFSSFG MSWVRQAPGKGLEWVSSISGSGSDTLYADSVKGRFTISR DNAKTTLYLQMNSLRPEDTAVYYCTIGGSLSRSSQGTLV TVSSA | SEQ ID NO: 37 without the added C-terminal amino acid residues |
| 38 | A | none | EVQLVESGGGLVQPGGSLRLSCAASGFTFSSYAMSWVR QAPGKGLEWVSGIKSSGDSTRYAGSVKGRFTISRDNAKN TLYLQMNSLRPEDTAVYYCAKSRVSRTGLYTYDNRGQG TLVTVSSGGGGSGGGGSGGGGSGGGGSEVQLVESGGGL VQPGGSLRLSCAASGRTFNNYAMGWFRQAPGKEREFVA AITRSGVRSGVSAIYGDSVKDRFTISRDNAKNTLYLQMN SLRPEDTAVYYCAASAIGSGALRRFEYDYSGQGTLVTVS SA | SEQ ID NO: 38 without the added C-terminal amino acid residues |
| 39 | A | none | EVQLVESGGGLVQPGGSLRLSCAASGFTFSSYPMGWFR QAPGKGREFVSSITGSGSTYYADSVKGRFTISRDNAKN TLYLQMNSLRPEDTAVYYCAAYIRPDTYLSRDYRKYDY WGQGTLVTVSSGGGGSGGGGSGGGGSEVQLVESGGGLVQPGNSL RLSCAASGFTFSSFGMSWVRQAPGKGLEWSSISGSGSD TLYADSVKGRFTISRDNAKTTLYLQMNSLRPEDTAVYY CTIGGSLSRSSQGTLVTVSSGGGGSGGGGSEVQLVESGGG LVQPGGSLRLSCAASGFTFSSYPMGWFRQAPGKGREFVS SITGSGGSTYYADSVKGRFTISRDNAKNTLYLQMNSLRP EDTAVYYCAAYIRPDTYLSRDYRKYDYWGQGTLVTVSS A | SEQ ID NO: 39 without the added C-terminal amino acid residues |

Figure 9 (continued)

| | | | |
|---|---|---|---|
| 40 | A | EVQLVESGGGLVQPGGSLRLSCAASGFTFSDYWMYWV RQAPGKGLEWVSEINTNGLITKYPDSVKGRFTISRDNAK NTLYLQMNSLRPEDTAVYYCARSPSGFNRGQGTLVTVS SGGGGSGGGSEVQLVESGGGLVQPGNSLRLSCAASGFTF SSFGMSWVRQAPGKGLEWVSSISGSGSDTLYADSVKGR FTISRDNAKTTLYLQMNSLRPEDTAVYYCTIGGSLSRSSQ GTLVTVSSGGGGSGGGGSEVQLVESGGGLVQPGGSLRLSC AASGFTFSDYWMYWVRQAPGKGLEWVSEINTNGLITKY PDSVKGRFTISRDNAKNTLYLQMNSLRPEDTAVYYCAR SPSGFNRGQGTLVTVSSA | SEQ ID NO: 40 without the added C-terminal amino acid residues |
| 41 | A | EVQLVESGGGLVQPGGSLRLSCAASGSTSYADSVKGRFTISRDNAKNTL YLQMNSLRPEDTAVYYCAFITTESDYDLGRRYWGQGTL VTVSSGGGGSGGGGSEVQLVESGGGLVQPGNSLRLSCAA SGFTFSSFGMSWVRQAPGKGLEWVSSISGSGSDTLYADS VKGRFTISRDNAKTTLYLQMNSLRPEDTAVYYCTIGGSL SRSSQGTLVTVSSA | SEQ ID NO: 41 without the added C-terminal amino acid residues |
| 42 | A | EVQLVESGGGLVQPGGSLRLSCAASGRTFSYNPMGWFR QAPGKGRELVAAISRTGGSTYYPDSVEGRFTISRDNAKR MVYLQMNSLRAEDTAVYYCAAAGVRAEDGRVRTLPSE YTFWGQGTQVTVSSAAAEVQLVESGGGLVQPGGSLRLS CAASGRTFSYNPMGWFRQAPGKGRELVAAISRTGGSTY YPDSVEGRFTISRDNAKRMVYLQMNSLRAEDTAVYYCA AAGVRAEDGRVRTLPSEYTFWGQGTQVTVSSA | SEQ ID NO: 42 without the added C-terminal amino acid residues |

Figure 9 (continued)

| | | | | |
|---|---|---|---|---|
| 43 | A | none | DVQLVESGGGLVQPGGSLRLSCAASGFILDYYAIGWFRQ APGKEREGVLCIDASDDITYYADSVKGRFTISRDNSKNT VYLQMNSLRPEDTAVYYCATPIGLSSSCLLEYDYDYWG QGTLVTVSSGGGGSGGGGSEVQLLESGGGLVQPGGSLRLS CAASGFTFRSFGMSWVRQAPGKGPEWVSSISGSGSDTLY ADSVKGRFTISRDNSKNTLYLQMNSLRPEDTAVYYCTIG GSLSRSSQGTLVTVSSA | SEQ ID NO: 43 without the added C-terminal amino acid residues |
| 44 | A | none | DVQLVESGGGLVQPGGSLRLSCAASRSIGRLDRMGWYR HRPGEPRELVATITGGSSINYGDSVKGRFTISIDNSKNTV YLQMNSLRPEDTAVYYCNFNKYVTSRDTWGQGTLVTV SSGGGGSGGGGSEVQLVESGGGLVQPGNSLRLSCAASGFT FSSFGMSWVRQAPGKGLEWVSSISGSGSDTLYADSVKG RFTISRDNAKTTLYLQMNSLRPEDTAVYYCTIGGSLSRSS QGTLVTVSSGGGGSGGGGSEVQLVESGGGLVQPGGSLRL SCAASRSIGRLDRMGWYRHRPGEPRELVATITGGSSINY GDSVKGRFTISIDNSKNTVYLQMNSLRPEDTAVYYCNFN KYVTSRDTWGQGTLVTVSSA | SEQ ID NO: 44 without the added C-terminal amino acid residues |
| 45 | none | P14A, P41T, S62F, S74A, S82bN, R83K, L108Q | EVQLVESGGGLVQAGGSLRLSCAASRSIGRLDRMGWYR HRTGEPRELVATITGGSSINYGDFVKGRFTISIDNAKNTV YLQMNNLKPEDTAVYYCNFNKYVTSRDTWGQGTQVTV SS | SEQ ID NO: 45 without the added C-terminal amino acid residues and without the mentioned mutations in the C-terminal region |
| 46 | AAEQKLIS EEDLNGA AHHHHHH | A14P, T41P, F62S, A74S, N82bS, K83R, Q108L | EVQLVESGGGLVQAGGSLRLSCAASRSIGRLDRMGWYR HRTGEPRELVATITGGSSINYGDFVKGRFTISIDNAKNTV YLQMNNLKPEDTAVYYCNFNKYVTSRDTWGQGTQVTV SSAAAHHHHHHGAAEQKLISEEDLNGAA | SEQ ID NO: 46 without the added C-terminal amino acid residues and without the mentioned mutations in the C-terminal region |

Figure 9 (continued)

| | | | | |
|---|---|---|---|---|
| 47 | GGGGSGG GSRDWDF DVFGGGT PVGG | none | EVQLVESGGGLVQPGGSLRLSCAASGSVFKINVMAWYR QAPGKGRELVAGIISGGSTSYADSVKGRFTISRDNAKNTL YLQMNSLRPEDTAVYYCAFITTESDYDLGRRYWGQGTL VTVSSGGGGSGGGGSRDWDFDVFGGGTPVGG | SEQ ID NO: 47 without the added C-terminal amino acid residues |
| 48 | AAEQKLIS EEDLNGA AHHHHHH | none | EVQLVESGGGLVQPGGSLRLSCIASGLPFSTKSMGWFRQ APGKEREFVARISPGGTSRYYGDFVKGRFAISRDNAKNT TWLQMNSLKAEDTAVYYCASGERSTYIGSNYYRTNEYD YWGTGTQVTVSSAAAEQKLISEEDLNGAAHHHHHH | SEQ ID NO: 48 without the added C-terminal amino acid residues |
| 49 | AAEQKLIS EEDLNGA AHHHHHH | V5L, I23A, E44G, A49S, A68T, A74S, T78L, W79Y, K83R, T110Q, Q108L | EVQLLESGGGLVQPGGSLRLSCAASGLPFSTKSMGWFR QAPGKGREFVSRISPGGTSRYYGDFVKGRFTISRDNSKN TLYLQMNSLRAEDTAVYYCASGERSTYIGSNYYRTNEY DYWGQGTLVTVSSAAAEQKLISEEDLNGAAHHHHHH | SEQ ID NO: 49 without the added C-terminal amino acid residues and without the mentioned mutations in the C-terminal region |
| 50 | none | L11S | HHHHHHHEVQLVESGGGGSVQPGNSLRLSCAASGFTFSSFG MSWVRQAPGKGLEWVSSISGSGSDTLYADSVKGRFTISR DNAKTTLYLQMNSLRPEDTAVYYCTIGGSLSRSSQGTLV TVSS | SEQ ID NO: 50 without the mentioned mutations in the C-terminal region |
| 51 | none | T110Q | HHHHHHHEVQLVESGGGGSVQPGNSLRLSCAASGFTFSSFG MSWVRQAPGKGLEWVSSISGSGSDTLYADSVKGRFTISR DNAKTTLYLQMNSLRPEDTAVYYCTIGGSLSRSSQGTLV QVSS | SEQ ID NO: 51 without the mentioned mutations in the C-terminal region |

Figure 9 (continued)

| 52 | none | S112G | HHHHHHEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVGS | SEQ ID NO: 52 without the mentioned mutations in the C-terminal region |
| --- | --- | --- | --- | --- |
| 53 | none | S113G | HHHHHHEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSG | SEQ ID NO: 53 without the mentioned mutations in the C-terminal region |
| 54 | none | L11S, T110Q, S112G, S113G | HHHHHHEVQLVESGGGSVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVQVGG | SEQ ID NO: 54 without the mentioned mutations in the C-terminal region |
| 55 | A | none | HHHHHHEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSA | SEQ ID NO: 55 without the added C-terminal amino acid residues |
| 56 | G | S113G | HHHHHHEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSGG | SEQ ID NO:56 without the added C-terminal amino acid residues and without the mentioned mutations in the C-terminal region |
| 57 | AS | none | HHHHHHEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSAS | SEQ ID NO:57 without the added C-terminal amino acid residues |

Figure 9 (continued)

| | | | |
|---|---|---|---|
| 58 | AST | none | HHHHHHEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSAST | SEQ ID NO:58 without the added C-terminal amino acid residues |
| 59 | ASTK | none | HHHHHHEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSASTK | SEQ ID NO:59 without the added C-terminal amino acid residues |
| 60 | ASP | none | HHHHHHEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSASP | SEQ ID NO:60 without the added C-terminal amino acid residues |
| 61 | AP | none | HHHHHHEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSAP | SEQ ID NO:61 without the added C-terminal amino acid residues |
| 62 | APT | none | HHHHHHEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSAPT | SEQ ID NO:62 without the added C-terminal amino acid residues |
| 63 | W | none | HHHHHHEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSW | SEQ ID NO:63 without the added C-terminal amino acid residues |
| 64 | L | none | HHHHHHEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSL | SEQ ID NO:64 without the added C-terminal amino acid residues |

Figure 9 (continued)

| | | | |
|---|---|---|---|
| 65 | none | P14A | HHHHHHEVQLVESGGGLVQAGGSLRLSCAASRSIGRLD RMGWYRHRPGEPRELVATITGGSSINYGDSVKGRFTISID NSKNTVYLQMNSLRPEDTAVYYCNFNKYVTSRDTWGQ GTLVTVSS | SEQ ID NO:65 without the mentioned mutations in the C-terminal region |
| 66 | none | L11S | HHHHHHEVQLVESGGGSVQPGGSLRLSCAASRSIGRLDR MGWYRHRPGEPRELVATITGGSSINYGDSVKGRFTISIDN SKNTVYLQMNSLRPEDTAVYYCNFNKYVTSRDTWGQG TLVTVSS | SEQ ID NO:66 without the mentioned mutations in the C-terminal region |
| 67 | none | R83K | HHHHHHEVQLVESGGGLVQPGGSLRLSCAASRSIGRLDR MGWYRHRPGEPRELVATITGGSSINYGDSVKGRFTISIDN SKNTVYLQMNSLKPEDTAVYYCNFNKYVTSRDTWGQG TLVTVSS | SEQ ID NO:67 without the mentioned mutations in the C-terminal region |
| 68 | none | P14A, L108Q | HHHHHHEVQLVESGGGLVQAGGSLRLSCAASRSIGRLD RMGWYRHRPGEPRELVATITGGSSINYGDSVKGRFTISID NSKNTVYLQMNSLRPEDTAVYYCNFNKYVTSRDTWGQ GTQVTVSS | SEQ ID NO:68 without the mentioned mutations in the C-terminal region |
| 69 | none | L108Q | HHHHHHEVQLVESGGGLVQPGGSLRLSCAASRSIGRLDR MGWYRHRPGEPRELVATITGGSSINYGDSVKGRFTISIDN SKNTVYLQMNSLRPEDTAVYYCNFNKYVTSRDTWGQG TQVTVSS | SEQ ID NO:69 without the mentioned mutations in the C-terminal region |
| 70 | none | T110Q | HHHHHHEVQLVESGGGLVQPGGSLRLSCAASRSIGRLDR MGWYRHRPGEPRELVATITGGSSINYGDSVKGRFTISIDN SKNTVYLQMNSLRPEDTAVYYCNFNKYVTSRDTWGQG TLVQVSS | SEQ ID NO:70 without the mentioned mutations in the C-terminal region |
| 71 | none | S113G | HHHHHHEVQLVESGGGLVQPGGSLRLSCAASRSIGRLDR MGWYRHRPGEPRELVATITGGSSINYGDSVKGRFTISIDN SKNTVYLQMNSLRPEDTAVYYCNFNKYVTSRDTWGQG TLVTVSG | SEQ ID NO:71 without the mentioned mutations in the C-terminal region |

Figure 9 (continued)

| | | | |
|---|---|---|---|
| 72 | none | S112G, S113G | HHHHHHEVQLVESGGGLVQPGGSLRLSCAASRSIGRLDRMGWYRHRPGEPRELVATITGGSSINYGDSVKGRFTISIDNSKNTVYLQMNSLRPEDTAVYYCNFNKYVTSRDTWGQGTLVTVGG | SEQ ID NO:72 without the mentioned mutations in the C-terminal region |
| 73 | G | S112G, S113G | HHHHHHEVQLVESGGGLVQPGGSLRLSCAASRSIGRLDRMGWYRHRPGEPRELVATITGGSSINYGDSVKGRFTISIDNSKNTVYLQMNSLRPEDTAVYYCNFNKYVTSRDTWGQGTLVTVGGG | SEQ ID NO:73 without the added C-terminal amino acid residues and without the mentioned mutations in the C-terminal region |
| 74 | G | none | HHHHHHEVQLVESGGGLVQPGGSLRLSCAASRSIGRLDRMGWYRHRPGEPRELVATITGGSSINYGDSVKGRFTISIDNSKNTVYLQMNSLRPEDTAVYYCNFNKYVTSRDTWGQGTLVTVSSG | SEQ ID NO:74 without the added C-terminal amino acid residues |
| 75 | AA | none | HHHHHHEVQLVESGGGLVQPGGSLRLSCAASRSIGRLDRMGWYRHRPGEPRELVATITGGSSINYGDSVKGRFTISIDNSKNTVYLQMNSLRPEDTAVYYCNFNKYVTSRDTWGQGTLVTVSSAA | SEQ ID NO:75 without the added C-terminal amino acid residues |
| 76 | GGG | none | HHHHHHEVQLVESGGGLVQPGGSLRLSCAASRSIGRLDRMGWYRHRPGEPRELVATITGGSSINYGDSVKGRFTISIDNSKNTVYLQMNSLRPEDTAVYYCNFNKYVTSRDTWGQGTLVTVSSGGG | SEQ ID NO:76 without the added C-terminal amino acid residues |
| 77 | A | none | HHHHHHEVQLVESGGGLVQPGGSLRLSCAASRSIGRLDRMGWYRHRPGEPRELVATITGGSSINYGDSVKGRFTISIDNSKNTVYLQMNSLRPEDTAVYYCNFNKYVTSRDTWGQGTLVTVSSA | SEQ ID NO:77 without the added C-terminal amino acid residues |

Figure 9 (continued)

| | | | | |
|---|---|---|---|---|
| 78 | none | Q13R | HHHHHHEVQLVESGGGLVRPGGSLRLSCAASRSIGRLDRMGWYRHRPGEPRELVATITGGSSINYGDSVKGRFTISIDNSKNTVYLQMNSLRPEDTAVYYCNFNKYVTSRDTWGQGTLVTVSS | SEQ ID NO:78 without the mentioned mutations in the C-terminal region |
| 79 | GG | none | HHHHHHEVQLVESGGGLVQPGGSLRLSCAASRSIGRLDRMGWYRHRPGEPRELVATITGGSSINYGDSVKGRFTISIDNSKNTVYLQMNSLRPEDTAVYYCNFNKYVTSRDTWGQGTLVTVSSGG | SEQ ID NO:79 without the added C-terminal amino acid residues |
| 80 | none | T110Q, S112G, S113G | HHHHHHEVQLVESGGGLVQPGGSLRLSCAASRSIGRLDRMGWYRHRPGEPRELVATITGGSSINYGDSVKGRFTISIDNSKNTVYLQMNSLRPEDTAVYYCNFNKYVTSRDTWGQGTLVQVGG | SEQ ID NO:80 without the mentioned mutations in the C-terminal region |
| 81 | none | L11V | HHHHHHEVQLVESGGGVVQPGGSLRLSCAASRSIGRLDRMGWYRHRPGEPRELVATITGGSSINYGDSVKGRFTISIDNSKNTVYLQMNSLRPEDTAVYYCNFNKYVTSRDTWGQGTLVTVSS | SEQ ID NO:81 without the mentioned mutations in the C-terminal region |
| 82 | none | P84A | HHHHHHEVQLVESGGGLVQPGGSLRLSCAASRSIGRLDRMGWYRHRPGEPRELVATITGGSSINYGDSVKGRFTISIDNSKNTVYLQMNSLRAEDTAVYYCNFNKYVTSRDTWGQGTLVTVSS | SEQ ID NO:82 without the mentioned mutations in the C-terminal region |
| 83 | none | T87A | HHHHHHEVQLVESGGGLVQPGGSLRLSCAASRSIGRLDRMGWYRHRPGEPRELVATITGGSSINYGDSVKGRFTISIDNSKNTVYLQMNSLRPEDAAVYYCNFNKYVTSRDTWGQGTLVTVSS | SEQ ID NO:83 without the mentioned mutations in the C-terminal region |
| 84 | none | S112G | HHHHHHEVQLVESGGGLVQPGGSLRLSCAASRSIGRLDRMGWYRHRPGEPRELVATITGGSSINYGDSVKGRFTISIDNSKNTVYLQMNSLRPEDTAVYYCNFNKYVTSRDTWGQGTLVTVGS | SEQ ID NO:84 without the mentioned mutations in the C-terminal region |

Figure 9 (continued)

| | | | |
|---|---|---|---|
| 85 | none | L11S, T110Q, S112G, S113G | HHHHHHEVQLVESGGGSVQPGGSLRLSCAASRSIGRLDR MGWYRHRPGEPRELVATITGGSSINYGDSVKGRFTISIDN SKNTVYLQMNSLRPEDTAVYYCNFNKYVTSRDTWGQG TLVQVGG | SEQ ID NO:85 without the mentioned mutations in the C-terminal region |
| 86 | none | L11S, T110Q | HHHHHHEVQLVESGGGSVQPGGSLRLSCAASRSIGRLDR MGWYRHRPGEPRELVATITGGSSINYGDSVKGRFTISIDN SKNTVYLQMNSLRPEDTAVYYCNFNKYVTSRDTWGQG TLVQVSS | SEQ ID NO:86 without the mentioned mutations in the C-terminal region |
| 87 | none | L11S, S112G, S113G | HHHHHHEVQLVESGGGSVQPGGSLRLSCAASRSIGRLDR MGWYRHRPGEPRELVATITGGSSINYGDSVKGRFTISIDN SKNTVYLQMNSLRPEDTAVYYCNFNKYVTSRDTWGQG TLVTVGG | SEQ ID NO:87 without the mentioned mutations in the C-terminal region |
| 88 | A | L11S, T110Q | HHHHHHEVQLVESGGGSVQPGGSLRLSCAASRSIGRLDR MGWYRHRPGEPRELVATITGGSSINYGDSVKGRFTISIDN SKNTVYLQMNSLRPEDTAVYYCNFNKYVTSRDTWGQG TLVQVSSA | SEQ ID NO:88 without the added C-terminal amino acid residues and without the mentioned mutations in the C-terminal region |
| 89 | none | L11S, P14A, T110Q, S112G, S113G | HHHHHHEVQLVESGGGSVQAGGSLRLSCAASRSIGRLD RMGWYRHRPGEPRELVATITGGSSINYGDSVKGRFTISID NSKNTVYLQMNSLRPEDTAVYYCNFNKYVTSRDTWGQ GTLVQVGG | SEQ ID NO:89 without the mentioned mutations in the C-terminal region |

SERUM ALBUMIN BINDING PROTEINS CONTAINING IMMUNOGLOBULIN SINGLE VARIABLE DOMAINS

RELATED APPLICATIONS

This application is a continuation of U.S. application Ser. No. 14/128,681, filed Mar. 4, 2014, which is a national stage application under 35 U.S.C. § 371 of international application PCT/EP2012/062251, filed Jun. 25, 2012, which was published under PCT Article 21(2) in English, which claims the benefit under 35 U.S.C. § 119(e) of U.S. provisional application Ser. No. 61/500,360, filed Jun. 23, 2011, U.S. provisional application 61/500,464, filed Jun. 23, 2011, and U.S. provisional application 61/541,368, filed Sep. 30, 2011; PCT/EP2012/062251 also claims the benefit under 35 U.S.C. § 120 of international application PCT/EP2011/067132, filed Sep. 30, 2011, U.S. application Ser. No. 13/435,567, filed Mar. 30, 2012 and now issued as U.S. Pat. No. 8,703,135, and international application PCT/EP2012/061304, filed Jun. 14, 2012. The disclosures of all of the foregoing applications are incorporated by reference herein in their entireties.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Jun. 6, 2017, is named A0848.70142US05-SEQ-JRV, and is 125,232 bytes in size.

The present invention relates to the field of immunoglobulin single variable domains.

An immunoglobulin single variable domain or "IS V" is generally defined herein as an amino acid sequence that:
- comprises an immunoglobulin fold or that, under suitable conditions (such as physiological conditions) is capable of forming an immunoglobulin fold (i.e., by folding), i.e., so as to form an immunoglobulin variable domain (such as, for example, a VH, VL or VHH domain);
and that
- forms (or under such suitable conditions is capable of forming) an immunoglobulin variable domain that comprises a functional antigen binding site (in the sense that it does not require an interaction with another immunoglobulin variable domain (such as a VH-VL interaction) to form a functional antigen binding site).

Some examples of immunoglobulin single variable domains that are currently known in the art are VHH's and/or (other) Nanobodies, dAb's and (single) domain antibodies. Of these, as of the date of filing of the present application, various Nanobodies are in phase I and phase II clinical trials. This makes it important to have available reliable assays for analyzing biological samples from people that are treated with ISV's (such as clinical trial subjects and, after such ISV's reach the market, patients that are treated with such ISV's).

This is not only important for regulatory purposes, but also for the treatment of patients with biological drugs, because the clinicians that prescribe the treatment would also like to have available reliable assays to monitor various aspects of the treatment.

For example, in the clinical development of biological drug molecules, it is important to assess their immunogenic potential, and in particular the degree to which they can elicit so-called "anti-drug antibodies" or "ADA's". This is determined using so-called "anti-drug antibody" or "ADA (immuno)assays" (see for example the review by Shankar et al., Journal of Pharmaceutical and Biomedical Analysis, 48 (2008), 1267-1281; as well as Mire-Sluis et al., J. Immunol. Meth. 289 (2004), 1-16; Peng et al., Journal of Pharmaceutical and Biomedical Analysis, 54, (2011), 629-635; and Loyet et al., J. Immunol. Meth. 345 (2009), 17-28. Such ADA assays and methods for performing them are standard knowledge in the field of pharmacology and they are routinely used during the clinical development of biological drug products (as well as being required by various regulatory agencies around the world).

For example, as described on pages 3 and 4 of the article by Mire-Sluis and as for example also exemplified schematically in the Figures of the article by Peng, a number of different ADA assay formats are known, such as "ELISA-bridging format", "ELISA-Direct Format", "Indirect Format", Radio Immuno-precipitation Assay (RIP), "Surface Plasmon Resonance" and "Electrochemiluminescence-Bridging Format". Other formats for performing ADA immunoassays will be clear to the skilled person.

The skilled person will also be familiar with a number of different commercially available technology platforms that have been shown to be suitable for setting up and performing ADA assays. These include but are not limited to the MSD platform (Mesoscale), Gyrolab (Gyros) and the octet platform (Fortebio).

Some non-limiting examples of ADA assay formats are also schematically shown in FIGS. 1A to 1C.

Generally, it should be noted that in such ADA assays for detecting or measuring ADA's against an ISV, the ISV is used as the "analytical agent" (i.e., as the compound used to detect whether any ADA's are present in the sample that is tested), and the ADA's are the "antigen" (i.e., the compound to be detected in the sample that is tested). Thus, in these assays, the ISV will usually/often be bound to the carrier (such as the ELISA plate), whereas the ADA's (if any) will be present in the sample that is subjected to the assay.

To better understand the invention described herein, it should already be noted that—by contrast—in the methods that are used herein to predict whether an ISV will give rise to protein interference, the ISV will usually be used as the "antigen" (i.e., as the compound to be detected), and an antibody (which is as further described herein) is used as the "analytical agent" (i.e., as a means to detect whether a given ISV binds or not, respectively; and thus has a high or increased risk of giving rise to protein interference or not, respectively). Thus, in this method according to the invention, the antibody used as analytical agent (which is also referred to herein as the "analytical antibody") will usually be bound to the carrier (i.e., to the ELISA plate) and the ISV will be (present in) the sample to be tested. However, it should generally be noted that the invention is not limited to assays in which the "analytical antibody" is bound to the carrier. For example, in an alternative way of performing an assay according to the invention (As shown for instance in FIG. 1 and described in the Examples), the analytical antibody is instead used as a bridging agent and thus will be in solution rather than bound to the plate (although it is indirectly bound to the plate via the ISV that is coated on the plate). However, also in the specific bridging assay described in the Examples (which is a competitive assay) the analytical antibody is still used as the analytical agent (i.e., to determine whether the ISV of interest binds or not, respectively; and thus has a high or increased risk of giving rise to protein interference or not, respectively). It is also envisaged that, based on the further disclosure herein, the skilled person will be able to design other assay formats in which the analytical antibody can be used as an analytical agent in order to determine whether a given ISV can bind or not, respectively; and thus has a high or increased risk of giving rise to protein interference or not).

As a result of research into single chain Fv's or "ScFv's" (which are constructs that contain immunoglobulin single variable domains that, similar to ISV's, are not associated with constant domains), it has been described in the art that the C-terminus of an immunoglobulin variable domain forms a hydrophobic patch that in an antibody is buried in the interface between the variable domain and the constant domain but that becomes solvent-exposed when the variable domain is not associated with a constant domain (Nieba et al., Protein Engineering, 10, 435-444 (1997)). It has also been described that the exposed C-terminus may form B-cell epitopes which can give rise to and/or interact with (emerging and/or pre-existing) anti-drug antibodies (WO 11/07586), the presence of which can then be determined using the ADA assays referred to above. For this reason, it has been proposed to make mutations to some of the amino acid residues that form part of the C-terminus of the variable domains to reduce said hydrophobicity and/or to remove said epitopes. For example, Nieba et al. suggest to mutate positions 11, 14, 41, 84, 87 and/or 89 of a VH region (numbering according to Kabat), whereas in WO 11/07586 it is suggested to mutate positions 99, 101 and/or 148 (AHo numbering) of a VL domain or positions 12, 97, 98, 99, 103 and/or 144 of a VH domain (again AHo numbering—these positions correspond to positions 11, 83, 84, 85, 89 and 103 according to Kabat).

However, neither of these references recognizes that certain proteins present in the blood or serum of a subject can interfere with ADA assays involving ISV's, and because of this these references are not directed to (nor offer a solution for) the problem of how to avoid aspecific protein interference in such ADA assays so as to allow the ADA assay to be used to determine the true presence/extent of (arising or pre-existing) anti-drug antibodies in the sample to be tested.

By contrast, the present invention provides methods and assays that easily allow the skilled person to predict whether an immunoglobulin single variable domain will or will not have a tendency to undergo aspecific protein interference in an ADA assay. The methods and assays described herein also allow the skilled person, when it is found that a variable domain may have a tendency or risk to undergo such protein interference in an ADA assay, to easily test (proposed) modifications to a variable domain in order to predict whether any such (proposed) modifications will reduce or essentially completely avoid such protein interference.

The present invention also describes a number of modifications that can be made to variable domains in order to reduce or essentially avoid such protein interference. According to one non-limiting aspect, this modification involves adding a limited number (as further described herein) of amino acid residues (as further described herein) to the C-terminal end of the variable domain. Surprisingly, it has been found that, for a number of different variable domains or constructs based thereon, even adding a single amino acid residue to the C-terminal end (such as a single alanine residue) can substantially or even essentially completely remove the problem of protein interference in ADA assays, even though adding one such amino acid is by itself is not sufficient to "cover" or "bury" the hydrophobic patch that according to Nieba et al. is present at the C-terminus of an ISV. Similarly, but without wishing to limit the invention in any way or to any mechanism or explanation, is also assumed that adding one such amino acid would not be sufficient to "cover" or "bury" any B-cell epitopes that according to WO 11/07586 may be present at the C-terminus of a variable domain It should also be noted that, although according to this specific aspect of the present invention, adding a limited number or even a single amino acid at the C-terminus of the variable domain (i.e. without making any substitutions within the C-terminal region itself, as proposed by Nieba et al and WO 11/07586) may—and in many cases will—significantly reduce or even essentially remove the problem of aspecific protein interference, it is also within the scope of this aspect of the invention that such additions to the C-terminal end are combined with mutations in the C-terminal region. In this respect, however, it should also be noted that the invention is not particularly limited as to the rationale behind making such mutations. For example, it is well known to make mutations to amino acid residues within the C-terminus (including at those positions that are explicitly referred to by Nieba et al. and in WO 11/07586) in order to humanize a variable domain (including, without limitation, a VHH domain) or in order to "camelize" a $V_H$ domain (reference is for example made to WO 08/020079 and some of the other applications by Ablynx N.V. referred to herein).

It is envisaged that the methods, assays and modifications taught herein can be applied to any variable domain that is not linked to or otherwise associated with a constant domain (or with another group or peptide moiety that functions to "shield", cover or "bury" the C-terminal region of the variable domain) and more generally to any variable domain that has a C-terminal regions that is solvent-exposed. However, according to one preferred, but non-limiting aspect of the invention, the methods, assays and modifications may in particular be applied to heavy chain variable domains ($V_H$ domains), and according to one specific aspect of the invention to $V_{HH}$ domains.

It is also envisaged that the methods, assays and modifications described herein can be suitably applied to protein constructs that contain one or more variable domains, and in particular to such constructs in which a variable domain forms the C-terminal part of the construct or, in the case of the methods and assays described herein, in which the C-terminal region of a variable domain is otherwise solvent-exposed. Again, according to one preferred, but non-limiting aspect of the invention, the methods, assays and modifications are applied to constructs in which a $V_H$ domain (and in particular a $V_{HH}$ domain) forms the C-terminal part of the construct or, in case of the methods and assays of the invention, is otherwise solvent-exposed.

Some non-limiting examples of such constructs are multivalent, multispecific (such as bispecific) or multiparatopic (such as biparatopic) constructs that contain two or more ISV's linked directly or via one or more suitable linkers (with again, according to one specific aspect, a $V_H$ or $V_{HH}$ domain) forming the C-terminal part of such a construct. For example, and without limitation, such a construct may be entirely comprised of $V_H$ domains, and in particular of Nanobodies (i.e. $V_{HH}$ domains, humanized $V_{HH}$ domains or camelized $V_H$ domains), again linked directly or via one or more suitable linkers. For some non-limiting examples of such constructs and a general teaching on how such constructs can be made (in particular based on Nanobodies) reference is for example made to Conrath et al., JBC 276, 10(9), 7346 (2001) as well as to the review article by Muyldermans. Reviews in Mol. Biotechnol., 74: 27 (2001).

However, it is for example also envisaged that the invention can be applied to other constructs which have a solvent-exposed variable domain and in particular have a variable domain at their C-terminus, such as for example single chain Fv's, and in particular ScFv's that have their heavy chain variable domain at the C-terminus.

In the present specification and claims, terms like "ISV", "analytical agent" and "protein interference" have the meaning as further defined herein.

In particular, an ISV as described herein may in particular either be a Nanobody or an(other) ISV (i.e. other than a Nanobody) that is a $V_H$ domain or that comprises a $V_H$ domain; and is preferably a Nanobody.

Also, any protein or polypeptide that comprises an ISV (such as an IS V-based drug) preferably has said (or at least one) such ISV at its C-terminal end. Again, said ISV may in particular either be a Nanobody or an(other) ISV (i.e. other than a Nanobody) that is a VH domain or that comprises a VH domain; and is preferably a Nanobody.

The invention described herein is in particular intended and suitable to be applied to ISVs that comprise, are based on and/or have been derived from heavy chain variable domains, such as VH domains (including human VH domains) and Nanobodies such as VHH domains (including humanized and sequence optimized VHH domains) or camelized VH domains. These may be synthetic (for example, obtained starting from a synthetic library and/or based on a fixed framework regions), semi-synthetic (for example, humanized, camelized or sequence-optimized, or obtained by affinity maturation or CDR grafting, starting from a natural VH or VHH domain) or fully naturally occurring VH or VHH domains. The invention will therefore be further described herein with reference to IS V's that are, are based on and/or have been derived from VH or VHH domains.

In establishing the present invention, it has been found that in some assays (such as, for example, in ADA immunoassays) that are used for analyzing biological samples (such as blood samples including whole blood, serum and plasma, ocular fluid, bronchoalveolar fluid/BALF, cerebrospinal fluid or other samples of biological fluids) protein interference may occur, and that such protein interference may give rise to an aspecific signal in some of these assays and/or in some of these samples. It has also been found that such protein interference may occur not only in samples that were obtained from subjects that have been treated with ISV's (and in particular with Nanobodies; or with proteins, polypeptides or other biological drugs that comprise at least one such ISV or Nanobody) and/or to whom the same have been administered (such as patients or clinical trial subjects), but also in samples from subjects that have never received an ISV (indicating that such interference is likely due to an aspecific protein-protein interaction with pre-existing proteins rather than any emerging ADA's).

Although it has been found that such protein interference and/or such a signal in such assays is not associated with any change or reduction in pharmacological properties (such as pharmacokinetic/PK or pharmacodynamic/PD properties) of the ISV's, it would be desirable to have techniques available for predicting, detecting, reducing and/or if possible avoiding such aspecific protein interference. This is the general objective of the present invention.

In particular, the invention provides, and in certain specific but non-limiting aspects relates to:
  assays that can be used to predict whether a given ISV will be subject to such protein interference and/or give rise to such an (aspecific) signal in such an assay (such as for example in an ADA immunoassay). Such predictive assays could for example be used to test whether a given ISV could have a tendency to give rise to such protein interference and/or such a signal; to select ISV's that are not or less prone to such protein interference or to giving such a signal; as an assay or test that can be used to test whether certain modification(s) to an ISV will (fully or partially) reduce its tendency to give rise to such interference or such a signal; and/or as an assay or test that can be used to guide modification or improvement of an ISV so as to reduce its tendency to give rise to such protein interference or signal;
  methods for modifying and/or improving IS V's to as to remove or reduce their tendency to give rise to such protein interference or such a signal;
  modifications that can be introduced into an ISV that remove or reduce its tendency to give rise to such protein interference or such a signal;
  ISV's that have been specifically selected (for example, using the assay(s) described herein) to have no or low(er)/reduced tendency to give rise to such protein interference or such a signal;
  modified and/or improved ISV's that have no or a low (er)/reduced tendency to give rise to such protein interference or such a signal.

For example, in a first non-limiting aspect, the invention relates to a method that can be used to predict whether a given ISV or Nanobody (or IS V-based or Nanobody-based drug) will give rise to (or has an high or increased risk of giving rise to) protein interference in an immunoassay (i.e., after it has been administered to a subject, a sample of a biological fluid has been obtained from said subject, and said sample is subjected to an immunoassay as further described herein), said method comprising performing an immunoassay that at least comprises the steps of:
  (i) contacting said ISV or Nanobody (or ISV-based or Nanobody-based drug) with an antibody that has been obtained from a human subject and that has been selected, generated and/or isolated based on its ability to recognize and/or bind to the C-terminal end of an ISV or Nanobody (the "analytical antibody"); and
  (ii) determining whether said ISV or Nanobody (or ISV-based or Nanobody-based drug) is bound by said antibody in said immunoassay.

In this method, when the ISV, Nanobody, ISV-based drug or Nanobody-based drug is bound by said analytical antibody, it can be expected that said ISV, Nanobody, ISV-based drug or Nanobody-based drug will give rise to (or has a high or increased risk of giving rise to) such protein interference (as further defined herein). Based on this, for example, said ISV, Nanobody, ISV-based drug or Nanobody-based drug may be modified or improved so as to reduce or remove its tendency to give rise to such protein interference (which may again be determined using the assay above), and some strategies that can be used to modify said ISV, Nanobody, IS V-based drug or Nanobody-based drug will be described herein (and for example include attaching a small number of amino acid residues to the C-terminal end and/or introducing one or more specific amino acid substitutions).

Thus, generally, the invention makes available to the skilled person assays and methods/techniques that can be used to predict the tendency of an ISV, Nanobody, ISV-based drug or Nanobody-based drug to give rise to protein interference and/or as a tool to improve ISVs so as to reduce or avoid their tendency to give rise to protein interference. In doing so, the invention also provides the skilled person with means to select ISV's, Nanobodies, ISV-based drugs or Nanobody-based drugs based on their low or reduced ability (or the absence of any ability) to give rise to protein interference. Thus, the invention provides the skilled person with an important assay and tool that can be used in the optimization and development of ISV's, Nanobodies, ISV-based drugs or Nanobody-based drugs.

Also, as further described herein, the invention teaches the skilled person a number of ways in which an ISV, Nanobody, ISV-based drug or Nanobody-based drug can be modified or improved so as to reduce or avoid their tendency to give rise to protein interference. Thus, the invention also generally makes available modified and/or improved ISV's, Nanobodies, ISV-based drugs or Nanobody-based drugs with a reduced, low or without any tendency to give rise to protein interference.

As further described herein, the invention can in particular be used to predict whether a given ISV or Nanobody (or ISV-based or Nanobody-based drug) will give rise to protein interference (as further described herein) in an immunoassay, and more in particular in an ADA assay. Said ADA assay may for example be an ADA assay for detecting or measuring ADA's against ISV's generally, and may in particular be an ADA assay for detecting or measuring ADA's against the ISV used in steps (i) and (ii) above.

Again, as mentioned herein, an ISV as described herein may in particular either be a Nanobody or an(other) ISV (i.e. other than a Nanobody) that is a VH domain or that comprises a VH domain; and is preferably a Nanobody.

Also, any protein or polypeptide that comprises an ISV (such as an IS V-based drug) preferably has said (or at least one) such ISV at its C-terminal end. Again, said ISV may in particular either be a Nanobody or an(other) ISV (i.e. other than a Nanobody) that is a VH domain or that comprises a VH domain; and is preferably a Nanobody.

The sample that is tested in said immunoassay or ADA assay is also referred to herein as the "test sample" or "assay sample". To avoid confusion, such as "test sample" or "assay sample" should not be confused with the biological sample that is used herein as a starting material for obtaining the (polyclonal or monoclonal) "analytical antibody" used in the invention.

In one particular preferred but non-limiting aspect, the invention can be used to predict whether a given ISV or Nanobody (or ISV-based or Nanobody-based drug) will give rise to protein interference (as further described herein) in an immunoassay (and in particular, in an ADA assay) that involves the use of such an ISV. Again, said ADA assay may for example be an ADA assay for detecting or measuring ADA's against ISV's generally, and may in particular be an ADA assay for detecting or measuring ADA's against the ISV used in steps (i) and (ii) above.

In an even more particular but non-limiting aspect, the invention can be used to predict whether a given ISV or Nanobody (or ISV-based or Nanobody-based drug) will give rise to protein interference (as further described herein) in an immunoassay (and in particular, in an ADA assay) that is intended to determine or measure whether the sample contains any ADA's against the ISV. Again, for example, such an immunoassay may be one of the known types of ADA assay (for which reference is for example made to the prior art on ADA assays cited herein) that is performed to determine or measure whether any ADA's against said ISV are present in the "test sample", wherein said test sample is a sample of biological fluid (as described herein) that is obtained from a subject to which said ISV has been administered (as further described herein).

As further described herein, in all these aspects (and the further aspects of the invention described herein), the invention can also be used to select ISV's that are not or less prone to such protein interference in such immunoassays or ADA assays; as an assay or test that can be used to test whether certain modification(s) to an ISV will (fully or partially) reduce its tendency to give rise to such interference in such immunoassays or ADA assays; and/or as an assay or test that can be used to guide modification or improvement of an ISV so as to reduce its tendency to give rise to such protein interference in such immunoassays or ADA assays.

Other aspects, embodiments, advantages and applications of the invention will become clear from the further description herein.

In the present specification, whenever the term "ISV" is used, it should be understood that:

such an ISV is preferably a Nanobody, in which the term "Nanobody" is generally as defined in or WO 08/020079 or WO 09/138519, and thus in a specific aspect generally denotes a VHH, a humanized VHH or a camelized VH (such as a camelized human VH) or generally a sequence optimized $V_{HH}$ (such as e.g. optimized for chemical stability and/or solubility, maximum overlap with known human framework regions and maximum expression). It is noted that the terms Nanobody or Nanobodies are registered trademarks of Ablynx N.V. and thus may also be referred to as Nanobody® and/or Nanobodies®);

the term "ISV" in its broadest sense also includes "ISV-based biologicals" and, when the ISV is a Nanobody, "Nanobody-based biologicals". An "ISV-based biological" is defined herein as a protein, polypeptide or other biological drug that comprises or essentially consist of at least one (such as one, two or three) ISV's. Similarly, a "Nanobody-based biological" is defined as a protein, polypeptide or other biological drug that comprises or essentially consist of at least one (such as one, two or three) Nanobodies. As with the term "ISV", whenever the term "ISV-based biological" is used, it should be understood that such an ISV-based biological is preferably a Nanobody-based biological. Within the context of the present invention, both an "ISV-based biological" and a "Nanobody-based biological" may for example be a monovalent, bivalent (or multivalent), bispecific (or multispecific), and biparatopic (or "multiparatopic) ISV construct or Nanobody construct, respectively. Also, any ISV-based or Nanobody-based biological may for example, in addition to the one or more (such as one, two or three) ISV's or Nanobodies, optionally further comprise one or more (such as one or two) other further therapeutic moieties and/or one or more (such as one or two) other moieties that influence the pharmacokinetic or pharmacodynamic properties of the ISV-based or Nanobody-based biological (such as its half-life). Suitable examples of such further therapeutic or other moieties will be clear to the skilled person, and for example generally can include any therapeutically active protein, polypeptide or other binding domain or binding unit, as well as for example modifications such as those described on pages 149 to 152 of WO 09/138159. An ISV-based biological or Nanobody-based biological is preferably a therapeutic or intended for use as a therapeutic (which includes prophylaxis and diagnosis) and for this purpose preferably contains at least one ISV against a therapeutically relevant target (such as for example RANK-L, vWF, IgE, RSV, CXCR4, IL-23 or other interleukins, etc.). For some specific but non-limiting examples of such ISV-based or Nanobody-based biologicals, reference is for example made to the various applications by Ablynx N.V. (such as for example and without limitation WO 2004/062551, WO 2006/122825, WO 2008/020079 and WO 2009/068627), as well as for example (and without limitation) to applications such as WO 06/038027, WO 06/059108, WO 07/063308, WO 07/063311, WO 07/066016 and WO 07/085814. Also, in the present specification, unless explicitly mentioned otherwise herein, all terms mentioned herein have the meaning given in WO 09/138519 (or in the prior art cited in WO 09/138519) or WO 08/020079 (or in the prior art cited in WO 08/020079). Also, where a method or technique is not specifically described herein, it can be performed as described in WO 09/138519 (or in the prior art cited in WO 09/138519) or WO 08/020079 (or in the prior art cited in WO 08/020079).

In particular, the following terms have the same meaning as given on, and/or where applicable can be determined in the manner described in, pages 62-75 of WO 09/138519: "agonist", "antagonist", "inverse agonist", "non-polar, uncharged amino acid residue", "polar uncharged amino acid residue", "polar, charged amino acid residue", "sequence identity", "exactly the same" and "amino acid difference" (when referring to a sequence comparison of two amino acid sequences), "(in) essentially isolated (form)", "domain", "binding domain", "antigenic determinant", "epitope", "against" or "directed against" (an antigen), "specificity" and "half-life". In addition, the terms "modulating" and "to modulate", "interaction site", "specific for", "cross-block", "cross-blocked" and "cross-blocking" and "essentially independent of the pH" are as defined on (and/or can be determined as described on) pages 74-79 of WO 10/130832 of applicant. Also, when referring to a construct, compound, protein or polypeptide of the invention, terms like "monovalent", "bivalent" (or "multivalent"), "bispecific" (or "multispecific"), and "biparatopic" (or "multiparatopic") may have the meaning given in WO 09/138.519, WO 10/130832 or WO 08/020079.

The term "half-life" as used herein relation to an ISV, Nanobody, IS V-based biological, Nanobody-based biological or any other amino acid sequence, compound or polypeptide can generally be defined as described in paragraph o) on page 57 of WO 08/020079 and as mentioned therein refers to the time taken for the serum concentration of the amino acid sequence, compound or polypeptide to be reduced by 50%, in vivo, for example due to degradation of the sequence or compound and/or clearance or sequestration of the sequence or compound by natural mechanisms. The in vivo half-life of an amino acid sequence, compound or polypeptide of the invention can be determined in any manner known per se, such as by pharmacokinetic analysis. Suitable techniques will be clear to the person skilled in the art, and may for example generally be as described in paragraph o) on page 57 of WO 08/020079. As also mentioned in paragraph o) on page 57 of WO 08/020079, the half-life can be expressed using parameters such as the t1/2-alpha, t1/2-beta and the area under the curve (AUC). In this respect it should be noted that the term "half-life" as used herein in particular refers to the t1/2-beta or terminal half-life (in which the t1/2-alpha and/or the AUC or both may be kept out of considerations). Reference is for example made to the Experimental Part below, as well as to the standard handbooks, such as Kenneth, A et al: Chemical Stability of Pharmaceuticals: A Handbook for Pharmacists and Peters et al, Pharmacokinete analysis: A Practical Approach (1996). Reference is also made to "Pharmacokinetics", M Gibaldi & D Perron, published by Marcel Dekker, 2nd Rev. edition (1982). Similarly, the terms "increase in half-life" or "increased half-life" as also as defined in paragraph o) on page 57 of WO 08/020079 and in particular refer to an increase in the t1/2-beta, either with or without an increase in the t1/2-alpha and/or the AUC or both.

When a term is not specifically defined herein, it has its usual meaning in the art, which will be clear to the skilled person. Reference is for example made to the standard handbooks, such as Sambrook et al, "Molecular Cloning: A Laboratory Manual" (2nd.Ed.), Vols. 1-3, Cold Spring Harbor Laboratory Press (1989); F. Ausubel et al, eds., "Current protocols in molecular biology", Green Publishing and Wiley Interscience, New York (1987); Lewin, "Genes II", John Wiley & Sons, New York, N.Y., (1985); Old et al., "Principles of Gene Manipulation: An Introduction to Genetic Engineering", 2nd edition, University of California Press, Berkeley, Calif. (1981); Roitt et al., "Immunology" (6th. Ed.), Mosby/Elsevier, Edinburgh (2001); Roitt et al., Roitt's Essential Immunology, 10th Ed. Blackwell Publishing, U K (2001); and Janeway et al., "Immunobiology" (6th Ed.), Garland Science Publishing/Churchill Livingstone, New York (2005), as well as to the general background art cited herein.

Also, herein, the amino acid residues of a Nanobody are numbered according to the general numbering for VH domains given by Kabat et al. ("Sequence of proteins of immunological interest", US Public Health Services, NIH Bethesda, Md., Publication No. 91), as applied to VHH domains from Camelids in the article of Riechmann and Muyldermans, J. Immunol. Methods 2000 Jun. 23; 240 (1-2): 185-195; or referred to herein. According to this numbering, FR1 of a Nanobody comprises the amino acid residues at positions 1-30, CDR1 of a Nanobody comprises the amino acid residues at positions 31-35, FR2 of a Nanobody comprises the amino acids at positions 36-49, CDR2 of a Nanobody comprises the amino acid residues at positions 50-65, FR3 of a Nanobody comprises the amino acid residues at positions 66-94, CDR3 of a Nanobody comprises the amino acid residues at positions 95-102, and FR4 of a Nanobody comprises the amino acid residues at positions 103-113. [In this respect, it should be noted that—as is well known in the art for VH domains and for VHH domains—the total number of amino acid residues in each of the CDR's may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence. Generally, however, it can be said that, according to the numbering of Kabat and irrespective of the number of amino acid residues in the CDR's, position 1 according to the Kabat numbering corresponds to the start of FR1 and vice versa, position 36 according to the Kabat numbering corresponds to the start of FR2 and vice versa, position 66 according to the Kabat numbering corresponds to the start of FR3 and vice versa, and position 103 according to the Kabat numbering corresponds to the start of FR4 and vice versa.].

Alternative methods for numbering the amino acid residues of VH domains, which methods can also be applied in an analogous manner to VHH domains from Camelids and to Nanobodies, are the method described by Chothia et al. (Nature 342, 877-883 (1989)), the so-called "AbM definition" and the so-called "contact definition". However, in the present description, aspects and figures, the numbering according to Kabat as applied to VHH domains by Riechmann and Muyldermans will be followed, unless indicated otherwise.

It should also be noted that the Figures, any Sequence Listing and the Experimental Part/Examples are only given to further illustrate the invention and should not be interpreted or construed as limiting the scope of the invention and/or of the appended claims in any way, unless explicitly indicated otherwise herein.

It should further be noted that the present invention is not specifically limited to any causation, explanation, hypothesis or mechanism of/for the protein interference (and/or signals arising in immunoassays) that is observed in, and that may be reduced according to, the present invention. However, it is assumed that the blood or serum (or other biological fluids, such as those mentioned herein) of certain individuals or groups of individuals may contain certain (pre-existing) proteins that under certain circumstances may (aspecifically) bind to ISV's leading to a interfering signal in certain assays that are used to analyze blood or serum samples obtained from such individuals. This is inter alia based on the observation made in establishing the present invention that the aspecific protein interference that is addressed by the present invention not only occurs when assaying samples that have been obtained from subjects to which an ISV has previously been administered, but also when assaying sample that have been obtained from subjects that have not previously received an ISV.

In particular, based on the observations that have been made in establishing the present invention, and although the invention is not limited thereto, it is thought that such (pre-existing) proteins may in particular (be able to) bind to the C-terminal end of such ISV's (which, in full sized conventional 4-chain monoclonal antibody as well as in the "heavy-chain only" antibodies that are found in Camelidae, are linked to the rest of the antibody—i.e. to the CH1 region in conventional monoclonals and to the hinge region in Camelidac heavy chain antibodies, respectively—and thus in such full-sized antibodies may be shielded from such protein interference).

This is confirmed by the findings made by the present inventors in establishing the present invention (which findings are further described herein) that certain (simple) modifications of ISV's at their C-terminal end may substantially reduce or essentially prevent such protein interference. Accordingly, methods for modifying ISV's in this manner as well as ISV's that have been modified in this manner form further aspects of the invention, as further described herein.

The present invention can in particular be used to reduce or avoid protein interference and/or signals due to aspecific binding in immunoassays that are performed on biological samples (such as blood or serum samples) obtained from a subject to whom a (biological) drug has been administered (again, such samples are also referred to herein as the "test sample" or "assay sample"). Some examples of this are immunoassays that are used for characterization of drug disposition and of the formation of antibodies upon administration of a biological drug to a subject, such as those referred to in the "Guideline on the Clinical Investigation of the Pharmacokinetics of Therapeutic Proteins" (document CHMP/EWP/89249/2004 dated Jan. 27, 2007) issued by the Committee for Medicinal Products for Human Use (CHMP) of the European Medicines Agency (EMEA). As stated on pages 4 and 5 of this document:

"Several possible weaknesses have been identified and may result in erroneous characterisation of drug disposition and of the formation of antibodies. The following issues should be considered [ . . . ]:
Immunoassay
Drug assay:
[ . . . ]
(iii) Interference by endogenous substances.
(iv) Interference by plasma components or anti-drug antibodies binding to the analyte and inhibiting the complementary binding to capture antibody."

The invention can in particular be used in order to predict, reduce or avoid this type of interference in immunoassays that are used in analyzing test samples/assay samples of biological fluids taken from subjects to whom ISV's (and in particular Nanobodies; or an ISV-based biological or Nanobody-based biological, as further defined herein) have been administered.

The invention can in particular be used in order to predict, reduce or avoid this type (aspecific) protein interference in immunoassays that are used for characterization of drug disposition and/or for determining the formation of any ADA's (anti-drug) antibodies. In this respect, should be noted that generally in this specification and in the attached claims, when wording like "predicting, reduce or avoiding protein interference" is used, this does not only include predicting, reduce or avoiding such protein interference per se, but also generally predicting, reduce or avoiding the occurrence of aspecific signals in immunoassays (such as those in which (aspecific) signals associated with protein interference may occur, for example in ADA assays), and in particular predicting, reduce or avoiding, in such immunoassays, the occurrence of aspecific signals that, when they are observed in such an assay, are usually attributed to, associated with and/or taken as a sign of (aspecific) protein interference. In this respect, it should generally be noted that, as mentioned herein, the present invention is not specifically limited to any causation, explanation, hypothesis or mechanism.

In one specific but non-limiting aspect, the invention can be used to predict, avoid or reduce such protein interference in "anti-drug antibody" or "ADA" assays that are performed on samples (i.e., "test samples") of biological fluids taken from subjects to whom ISV's (and in particular Nanobodies; or an ISV-based biological or Nanobody-based biological, as further defined herein) have been administered.

In another specific but non-limiting aspect, the invention can be used to predict, avoid or reduce such protein interference (and/or aspecific signals usually associated with the same) in "anti-drug antibody" or "ADA" assays that are used to detect, measure and/or characterize the presence of (any) anti-drug antibodies against one or more ISV's (and in particular against Nanobodies; or an ISV-based biological or Nanobody-based biological, as further defined herein). In particular, the invention can be used to predict, avoid or reduce such protein interference in such "anti-drug antibody" or "ADA" assays that are performed on samples (i.e., "test samples") of biological fluids, and more in particular on samples of biological fluids of that have been obtained from a subject to whom one or more such ISV's or Nanobodies (or an ISV-based biological or Nanobody-based biological, as further defined herein) have been administered. For example, the invention can be used to predict, avoid or reduce such protein interference in such "anti-drug antibody" or "ADA" assays that are used to detect, measure and/or characterize the presence of (any) anti-drug antibodies against the ISV or Nanobody (or an ISV-based biological or Nanobody-based biological, as further defined herein) that has been administered to the subject from which the sample has been obtained (either in the context of a clinical trial and/or in the context of therapy).

Thus, in one specific, but non-limiting aspect, the invention can be used to predict, avoid or reduce such protein interference (and/or aspecific signals usually associated with the same) in biological samples (i.e., "test samples") obtained from a subject to whom one or more such ISV's or Nanobodies (or an ISV-based biological or Nanobody-based biological, as further defined herein) have been administered, wherein said samples as suitable for and/or intended for use in an immunological assay, such as an ADA assay. As mentioned, such a biological sample may be blood (including whole blood, serum or plasma), ocular fluid, bronchoalveolar fluid/BALF, cerebrospinal fluid or any other suitable biological fluid or sample that is suitable for use in an immunoassay, and in particular an ADA assay.

In one specific, but non-limiting aspect, such a test sample may have been obtained from a subject that has been subjected to multiple administrations (for example at least 1 to 3 separate administrations over a period of at least 10 days, such as at least one month or longer) and/or to chronic treatment (i.e. treatment during at least 10 days such as at least one month) with an ISV, Nanobody, an ISV-based biological (as further defined herein) or Nanobody-based biological (as further defined herein). Such an ISV, Nanobody, ISV-based biological or Nanobody-based biological may for example have been administered to said subject in the context of therapy or in the context of a clinical trial.

In one specific, but non-limiting aspect, such a test sample may have been obtained from a subject to which a ISV, Nanobody, ISV-based biological or Nanobody-based biological has been administered that has (and/or has been provided with) an increased half-life (as defined herein, and compared to a monovalent ISV), for example a half-life of at least 1 day, preferably at least 3 days, more preferably at least 7 days, such as at least 10 days in the subject to which the same is/has been administered.

For example and without limitation, such an ISV, Nanobody, ISV-based biological or Nanobody-based biological may have been provided with an increased half-life by functionalization and/or by including in the construct a moiety or binding unit that increases the half-life of the construct. Examples of such functionalization, moieties or binding units will be clear to the skilled person and may for example be as described herein, and for example may include pegylation, fusion to scrum albumin, or fusion to a peptide or binding unit that can bind to a serum protein such as serum albumin. Such a serum-albumin binding peptide or binding domain may be any suitable serum-albumin binding peptide or binding domain capable of increasing the half-life of the construct (compared to the same construct without the serum-albumin binding peptide or binding domain), and may in particular be serum albumin binding peptides as described in WO 2008/068280 by applicant (and in particular WO 2009/127691 and the non-prepublished U.S. application 61/301,819, both by applicant), or a serum-albumin binding ISV (such as a serum-albumin binding Nanobody; for example Alb-1 or a humanized version of Alb-1 such as Alb-8, for which reference is for example made to WO 06/122787).

Thus, in one specific but non-limiting aspect, such a biological sample may have been obtained from a subject to which an ISV, Nanobody, ISV-based biological or Nanobody-based biological has been administered that comprises a (human) serum albumin-binding binding peptide or binding domain.

As already mentioned above, in one non-limiting aspect, the invention generally relates to a method that can be used to predict whether a given ISV or Nanobody (or ISV-based or Nanobody-based drug) will give rise to (or has high or increased tendency to give rise to) protein interference (as further described herein) in an immunoassay (i.e. after said ISV has been administered to a subject, a sample of a biological fluid has been obtained from said subject, and said biological fluid is subjected to an immunoassay as further described herein), said method comprising performing an immunoassay that at least comprises the steps of:
 (i) contacting said ISV or Nanobody (or ISV-based or Nanobody-based drug) with an antibody that has been obtained from a human subject and that has been selected, generated and/or isolated based on its ability to recognize and/or bind to the C-terminal end of an ISV or Nanobody (the "analytical antibody"); and
 (ii) determining whether said ISV or Nanobody (or ISV-based or Nanobody-based drug) is bound by said antibody in said immunoassay.

Again, as mentioned herein, an ISV as described herein may in particular either be a Nanobody or an(other) ISV (i.e. other than a Nanobody) that is a VH domain or that comprises a VH domain; and is preferably a Nanobody.

Also, any protein or polypeptide that comprises an ISV (such as an IS V-based drug) preferably has said (or at least one) such ISV at its C-terminal end. Again, said ISV may in particular either be a Nanobody or an(other) ISV (i.e. other than a Nanobody) that is a VH domain or that comprises a VII domain; and is preferably a Nanobody.

In an alternative embodiment, which is also further described herein, instead of the aforementioned antibody obtained from a human subject, the monoclonal antibody referred to herein as "21-4-3" (or "21-4" for short, see SEQ ID NO's 35 and 36 for the VH and VL sequences) may be used. 21-4 was generated using hybridoma technology starting from a mouse immunized with the Nanobody construct of SEQ ID NO:98 in WO 2006/122825, as further described in Example 7, and a hybridoma cell line (called "ABH0015") expressing 21-4 has been deposited on Jun. 4, 2012 with the BCCM, Ghent, Belgium, under accession number LMBP-9680-CB. Monoclonal 21-4 has been shown to recognize the C-terminus the Nanobody construct of SEQ ID NO:98 in WO 2006/122825, which C-terminal end consists of a Nanobody (humanized $V_{HH}$) raised against Von Willebrand Factor (vWF). 21-4 was originally raised as analytical reagent for use in detecting the protein Nanobodies (n particular, the Nanobody construct of SEQ ID NO:98 in WO 2006/122825) in (scrum) samples; surprisingly, it has now been found that 21-4 can also be used in order to predict whether an ISV has a tendency to undergo aspecific protein interference (more so than some other, comparable (mouse) monoclonals raised against the Nanobody construct of SEQ ID NO:98 in WO 2006/122825 or against other Nanobodies).

In particular, it has been found that if measuring the binding of 21-4 to an ISV (or to protein or polypeptide containing an ISV at its C-terminal end, or similar protein or polypeptide as mentioned herein) gives an RU value of less than 500 (after adjusting the measured RU value for the molecular weight to the protein, according to the formula [RU measured]/[MW of the protein]×$10^6$) when determined according to the protocol set out in Example 9, that said ISV or protein will likely not have a tendency to undergo protein interference (within the confidence provided by the data set out in the Examples below). For the purposes of the above formula, MW may be calculated as the sum of all the MW's of all the amino acid residues present in the ISV.

Accordingly, any ISV, protein or polypeptide described herein preferably has such an RU value for binding by 21-4 of less than 500 (determined according to the protocol set out in Example 9, and after adjusting the measured RU value for the molecular weight of the ISV or protein used according to the formula set out above).

Thus, this aspect of the invention generally relates to a method that can be used to predict whether a given ISV or Nanobody (or ISV-based or Nanobody-based drug) will give rise to (or has high or increased tendency to give rise to) protein interference (as further described herein) in an immunoassay (i.e. after said ISV has been administered to a subject, a sample of a biological fluid has been obtained from said subject, and said biological fluid is subjected to an immunoassay as further described herein), said method comprising performing an immunoassay that at least comprises the steps of:
  (i) contacting said ISV or Nanobody (or ISV-based or Nanobody-based drug) with the monoclonal antibody 21-4 (i.e. used as the "analytical antibody"); and
  (ii) determining whether said ISV or Nanobody (or ISV-based or Nanobody-based drug) is bound by the monoclonal antibody 21-4 in said immunoassay.

Said method may in particular be performed using BiaCore or a similar technique, and more in particular using the protocol set out in Example 9. As mentioned herein, when the binding of the ISV or ISV-based drug in this protocol shows an RU value of less than 500 (after adjusting the measured RU value for the molecular weight to the protein, according to the formula [RU measured]/[MW of the protein]×$10^6$), said ISV or ISV-based protein will likely not be bound by any interference factor(s) present in the blood or serum of a human being and/or will likely not have a tendency to undergo aspecific protein interference in an ADA assay (i.e. within the degrees of confidence set out in the experimental part below).

Again, as mentioned herein, an ISV as described herein may in particular either be a Nanobody or an(other) ISV (i.e. other than a Nanobody) that is a VH domain or that comprises a VH domain; and is preferably a Nanobody.

Also, any protein or polypeptide that comprises an ISV (such as an ISV-based drug) preferably has said (or at least one) such ISV at its C-terminal end. Again, said ISV may in particular either be a Nanobody or an(other) ISV (i.e. other than a Nanobody) that is a VH domain or that comprises a VH domain; and is preferably a Nanobody.

As also mentioned herein, the above method using 21-4 can also be used to determine whether an ISV or protein or polypeptide that comprises a ISV is bound by (or has a tendency to be bound by) interference factor(s) that are present in the blood or serum of a human being.

Also, as mentioned herein, it is envisaged that said method using 21-4 can also be used to predict whether any protein or polypeptide (such as an antibody fragment or ScFv) that has a VH domain at its C-terminal end will bound by (or has a tendency to be bound by) interference factor(s) that are present in the blood or serum of a human being and/or has a tendency to undergo protein interference in an ADA assay.

In addition to 21-4, it is envisaged that an antibody or antibody fragment (such as a suitable Fab fragment) that contains the heavy chain and light chain variable domains of 21-4 (see SEQ ID NO's: 35 and 36, respectively) or even only the CDR sequences of 21-4 (suitably grafted into other suitable VH and VK frameworks) may also be used in the methods described herein.

As further described herein, the invention can in particular be used to predict whether a given ISV or Nanobody (or ISV-based or Nanobody-based drug) will give rise to protein interference (as further described herein) in an immunoassay that is an ADA assay. Said ADA assay may for example be an ADA assay for detecting or measuring ADA's against ISV's generally, and may in particular be an ADA assay for detecting or measuring ADA's against the ISV used in steps (i) and (ii) above.

In one particular preferred but non-limiting aspect, the invention can be used to predict whether a given ISV or Nanobody (or ISV-based or Nanobody-based drug) will give rise to protein interference (as further described herein) in an immunoassay (and in particular, in an ADA assay) that involves the use of such an ISV. Again, said ADA assay may for example be an ADA assay for detecting or measuring ADA's against ISV's generally, and may in particular be an ADA assay for detecting or measuring ADA's against the ISV used in steps (i) and (ii) above.

In an even more particular but non-limiting aspect, the invention can be used to predict whether a given ISV or Nanobody (or ISV-based or Nanobody-based drug) will give rise to protein interference (as further described herein) in an immunoassay (and in particular, in an ADA assay) that involves the use of such an ISV. For example, such an immunoassay may be an ADA assay (i.e. involving the ISV) that is performed to determine or measure whether any ADA's against said ISV are present in the sample that is tested, wherein said sample is a sample of biological fluid (as described herein) that is obtained from a subject to which said ISV has been administered (as further described herein). For example, as further mentioned herein, said sample (i.e., the "test sample") may be a sample of (including whole blood, serum or plasma), ocular fluid, bronchoalveolar fluid/BALF, cerebrospinal fluid or any other suitable biological fluid, and may in particular be a biological sample that is suitable for and/or intended for use in an immunological assay, such as an ADA assay.

As further described herein, in all these aspects (and the further aspects of the invention described herein), the invention can also be used to select ISV's that are not or less prone to such protein interference in such immunoassays or ADA assays; as an assay or test that can be used to test whether certain modification(s) to an ISV will (fully or partially) reduce its tendency to give rise to such interference in such immunoassays or ADA assays; and/or as an assay or test that can be used to guide modification or improvement of an ISV so as to reduce its tendency to give rise to such protein interference in such immunoassays or ADA assays.

As mentioned, step (i) of the method of the invention comprises contacting said ISV or Nanobody (or ISV-based or Nanobody-based drug) with an antibody that has been obtained from a human subject and that has been selected/isolated based on its ability to recognize and/or bind to the C-terminal end of an ISV or Nanobody (as further described herein). In said step (i) of the method described herein, "said ISV or Nanobody (or ISV-based or Nanobody-based drug)" is used as the antigen in the immunoassay (i.e. as the substance to be detected). Also, in said step (i), the "antibody that has been obtained from a human subject and that has been selected/isolated based on its ability to recognize and/or bind to the C-terminal end of an ISV or Nanobody" is used as the analytical reagent (i.e. in the same way as other antibodies are used in immunoassays to detect the presence of an antigen to which they are directed).

As already mentioned, and in order to better understand the invention described herein, it should be noted that, in step (i), the ISV will usually be used as the "antigen" (i.e., as the compound to be detected), and the "analytical antibody" will be used as the analytical agent (i.e., as a means to detect whether a given ISV binds or not, respectively; and thus has a high or increased risk of giving rise to protein interference or not, respectively). For example, when step (i) is performed in an ELISA format, the "antibody/analytical agent" will usually be bound to the carrier (i.e., to the ELISA plate) and the ISV will be (present in) the sample to be tested.

By contrast, it should be noted that in ADA assays for detecting or measuring ADA's against an ISV, the ISV is used as the "analytical agent" (i.e., as the compound used to detect whether any ADA's are present), and the ADA's are the "antigen" (i.e., the compound to be detected). Thus, in these assays, the ISV will usually/often be bound to the carrier (such as the ELISA plate), whereas the ADA's (if any) will be present in the sample that is subjected to the assay.

However, as already mentioned, it should generally be noted that the invention is not limited to assays in which the "analytical antibody" is bound to the carrier. For example, in an alternative way of performing an assay according to the invention (as shown in Example 5), the analytical antibody is instead used as a bridging agent and thus will be in solution rather than bound to the plate (although it is indirectly bound to the plate via the ISV that is coated on the plate). However, also in the specific (bridging) assay described in Example 5 (which is a competitive assay) the analytical antibody is still used as the analytical agent (i.e., to determine whether the ISV of interest binds or not, respectively; and thus has a high or increased risk of giving rise to protein interference or not, respectively). It is also envisaged that, based on the further disclosure herein, the skilled person will be able to design other assay formats in which the analytical antibody can be used as an analytical agent in order to determine whether a given ISV can bind or not, respectively; and thus has a high or increased risk of giving rise to protein interference or not).

The "analytical antibody" used in step (i) may be a polyclonal or monoclonal antibody.

When the analytical antibody is a polyclonal antibody, it may for example be a polyclonal antibody (preparation) that has been obtained/purified/isolated from a biological sample obtained of a human subject (such as blood, plasma, B-cells or another suitable biological sample or fluid from which polyclonal antibodies can be suitably isolated). This may for example be a suitable biological sample that has been obtained of a human subject to which at least one ISV (such as the ISV used in step (i), but this is not required or essential) has been administered, but may also be (and preferably is) a suitable biological sample from a human subject which has never received or been treated with an ISV. What is more important is that the polyclonal antibody has been obtained from said biological sample by a method that involves at least one affinity step using an affinity matrix or column that carries an ISV as the affinity moiety (and one or more further steps for obtaining/purifying/isolating polyclonal antibodies known per se). For example, the polyclonal antibody may have been obtained from such a biological sample by means of affinity chromatography using an affinity column that carries an ISV, as for example described in Example 2. This may for example be performed using well known techniques for immunoaffinity chromatography for isolating antibodies from a biological sample, using an affinity matrix that carries an ISV as the antigen. Such techniques are generally known in the art and suitable examples thereof will be clear to the skilled person based on the disclosure herein.

Such a polyclonal antibody (preparation) may in particular be an IgG (or IgG fraction).

For example, it may be a polyclonal antibody that has been obtained means of a method that involves (immuno) affinity chromatography, performed on a sample of biological fluid obtained from a human subject, using as the antigen bound to the affinity matrix an ISV (and in particular a Nanobody, such as a VHH, humanized and/or sequence-optimized VHH or a camelized VH, such as a camelized human VH) that does not contain a C-terminal tag (i.e., of which the C-terminus ends with the amino acid sequence VTVSS (SEQ ID NO:33)). In particular, the ISV used as the antigen bound to the affinity matrix may be a humanized or sequence-optimized VHH (or alternatively a corresponding camelized human VH) of which the C-terminus ends with the amino acid sequence VTVSS (SEQ ID NO:33). In one specific, but non-limiting aspect, the ISV used as the antigen bound to the affinity matrix may be a humanized or sequence-optimized VHH that, as a result of such humanization or sequence-optimization, comprises a proline (P) residue at position 14 where the corresponding "naïve" VHH comprises an alanine (A) at position 14 (in other words, the ISV used as the antigen is a humanized version of a VHH that naturally comprises an alanine at position 14, which alanine residue, as a result of the humanization and/or sequence optimization, has been replaced with a proline (P) residue). The ISV used as the antigen may also comprise one or more other amino acid substitutions as a result of such humanization or sequence optimization, for example generally described in WO 08/020079 or WO 09/138519.

Some specific examples of ISVs that can be used as the antigen to generate/isolate the "analytical antibody" used in the invention are given in SEQ ID NO's: 1 and 2.

Again, the method used to obtain the polyclonal antibody may, in addition to the (immune)affinity steps, also comprise one or more further steps for isolating/purifying a polyclonal antibody from the biological sample (performed either before or after the affinity steps). Again, such steps and techniques for performing them will be clear to the skilled person.

Thus, in one aspect, the invention comprises a method as further described herein that comprises steps (i) and (ii) described herein, in which the "analytical antibody" (i.e., the antibody that has been obtained from a human subject and that has been selected/isolated based on its ability to recognize and/or bind to the C-terminal end of an ISV or Nanobody) has been obtained from a biological sample obtained from a human subject (wherein said biological sample is a sample that is suitable for use in a method for generating/isolating an antibody from said sample) using a method that comprises at least one affinity step (such as a step of affinity chromatography, such as immunoaffinity chromatography) in which an ISV (and preferably a Nanobody) is used as an antigen, and preferably an ISV is used as an antigen that comprises the amino acid sequence VTVSS (SEQ ID NO:33) as the C-terminal sequence, and more preferably a humanized and/or sequence optimized Nanobody is used as the antigen that comprises the amino acid sequence VTVSS (SEQ ID NO:33) as the C-terminal sequence, and even more preferably a humanized and/or sequence optimized Nanobody is used as the antigen that comprises the amino acid sequence VTVSS (SEQ ID NO:33) as the C-terminal sequence and that comprises a proline residue at position 14, such as a Nanobody that comprises the amino acid sequence VTVSS (SEQ ID NO:33) as the C-terminal sequence and that comprises a proline residue at position 14 that has been introduced into the Nanobody as a result of said humanization and/or sequence-optimization (for example, to replace an alanine residue that naturally occurs at said position in the VHH that has been humanized and/or sequence optimized).

The above ISV's can also be used in methods to isolate monoclonal antibodies (again starting from a suitable biological sample obtained from a human being) that are suitable for use in the invention as the "analytical antibody".

For example, such a monoclonal antibody may be obtained starting from blood. B-cells or another suitable sample or material for isolating antibodies, may be selected based on its ability to recognize and/or bind to (the C-terminal end of) an ISV or Nanobody (in which, again, the ISV(s) used as the antigen during screening and/or selection is preferably as described in the preceding paragraphs, including the preferences stated for such ISV/antigen). Such screening and selection may be performed in any suitable manner, for example by using B-cell selection and/or expansion techniques essentially the same or suitably similar to the B-cell selection techniques described in EP 0 488 470, WO 92/02551, EP 1 633 787, WO 01/55216, WO 02/26829, WO 04/051268, WO 04/102198 or WO 04/106377 or techniques similar to the Nanoclone technique described in WO 06/079372 (but using human B-cells rather than camelid B-cells).

Once one or more B-cells have been identified/isolated that express a suitable antibody, said antibody may be isolated, expressed and/or produced in any suitable manner. For example, said B-cell(s) may be immortalized as hybridomas producing the desired antibody/antibodies (using techniques well known per se for generating hybridomas starting from selected B-cells), and said antibody/antibodies may then be isolated from (the culture supernatant of) said hybridoma(s), again using suitable techniques well established in the art and described in various handbooks and manuals, and also described and/or referred to in the patent publications mentioned in the preceding paragraph.

Alternatively, said B-cell(s) may be expanded using B-cell expansion techniques known per se, and the antibody/antibodies may be isolated from (the culture supernatant of) said expanded B-cell(s). Again, this may be performed using suitable techniques well established in the art and described in various handbooks and manuals, and also described and/or referred to in the patent publications mentioned in the preceding paragraphs.

In yet another alternative. DNA encoding the antibody/antibodies of interest may be obtained (e.g., by amplification) from said B-cell(s) or other suitable cells, either directly (for example using suitable single-cell PCR cloning techniques) or after suitable expansion of the desired B-cell (s). Said DNA may then be suitably expressed in a suitable host cell or host organism to provide the desired antibody/antibodies. Again, this may be performed using suitable techniques well established in the art and described in various handbooks and manuals, and also described and/or referred to in the patent publications mentioned in the preceding paragraphs.

It is also possible to generate monoclonal antibodies that are suitable for use as the "analytical antibody" by a method that involves repertoire cloning (starting from a suitable sample obtained from a human subject) and screening the cloned repertoire for antibodies that bind to the ISV used as antigen (in which, again, the ISV(s) used as the antigen during screening and/or selection is preferably as described in the preceding paragraphs, including the preferences stated for such ISV/antigen). Methods for repertoire cloning and various techniques for displaying cloned repertoires for selection and screening (such as phage display, ribosome display and yeast display) will be clear to the skilled person, and are for example described in EP 0 589877, EP 0 774 511, WO 90/14430 and EP 0368 684) as well as various handbooks on the subject.

Generally, the biological sample that is used as a starting point for obtaining the (polyclonal or monoclonal) analytical antibody may be any suitable sample (i.e. suitable as a starting material for obtaining a polyclonal or monoclonal antibody, respectively) obtained from any suitable human subject. In one specific but non-limiting aspect, such a sample may for example have been obtained from a woman, and in particular a post-menopausal woman. Thus, in one specific but non-limiting aspect, the analytical antibody used in steps (i) and (ii) above has been obtained starting from a biological sample that has been obtained/derived from a post-menopausal woman (or has been derived from an antibody that has been obtained/derived from a post-menopausal woman).

Also, the biological sample that is used as a starting point for obtaining the (polyclonal or monoclonal) analytical antibody may be obtained from a subject to whom an ISV has previously been administered (for example, as part of a clinical trial or therapeutically), but is preferably obtained from a subject to whom no ISV has previously been administered.

However, it should be noted that the invention is not particularly limited to the source of the analytical antibody/antibodies used, and it has proven possible in some cases, using the techniques described herein, to obtain (generate, isolate) other suitable analytical antibodies from other sources, including commercially available human blood or plasma (and even blood, plasma or B-cells from other species of mammals or primates, such as from baboon or cynomolgus monkey).

As mentioned above, the (polyclonal or monoclonal) analytical antibody used in steps (i) and (ii) should be such that it is capable of recognizing or binding to the C-terminal end of an ISV or Nanobody, and is most preferably selected and/or isolated based on this ability to hind to the C-terminal end of an ISV or Nanobody.

As can be seen from FIG. 2, when the ISV is based on or derived from a VH or VHH domain, the C-terminal end of an ISV comprises the amino acid sequence VTVSS (SEQ ID NO:33), and accordingly the analytical antibody should be capable of recognizing any ISV that has the amino acid sequence VTVSS (SEQ ID NO:33) at its C-terminal end. As can be further seen from FIG. 2, (at least some of the amino acid residues in) the sequence VTVSS (SEQ ID NO:33) is part of a putative epitope on the ISV that also includes, among other residues, the amino acid residue at position 14 (and the amino acid residues next/close to the same in the amino acid sequence, such as positions 11, 13 and 15) and may also comprise the amino acid residue at position 83 (and the amino acid residues next/close to the same in the amino acid sequence, such as positions 82, 82a, 82b and 84) and/or the amino acid residue at position 108 (and the amino acid residues next/close to the same in the amino acid sequence, such as positions 107. Position 109 is the first V of the C-terminal VTVSS (SEQ ID NO:33) sequence and it has been shown that for example position 110 may have an influence on protein interference as well). This is also collectively referred to herein as the "C-terminal region", it being understood that this C-terminal region at least comprises the C-terminal sequence VTVSS (SEQ ID NO:33) and the amino acid residue at position 14, and may also comprise the amino acid residues at positions 83 and 108, and possibly also the amino acid residues at positions 13, 15, 82b, 83, 84 and 107.

As already mentioned, and again without being limited to any hypothesis or explanation, in a full-sized 4-chain monoclonal antibody, or in a full-sized heavy chain only antibody such as those present in Camelidae, the C-terminal end of a VH or VHH domain is linked to the rest of the antibody—i.e. to the CH1 region in conventional monoclonals or to the hinge region in Camelidae heavy chain antibodies, respectively—and thus in such full-sized antibodies may be shielded from such protein interference) and/or covered by the VH/VL interaction (in conventional 4-chain antibodies) so that this "C-terminal region" and is therefore usually not solvent-exposed and/or accessible as an interaction site for proteins that are present in the blood, serum or body of a person to which such an ISV is administered. However, if an ISV or Nanobody is used per se (i.e. without being linked to any other part of an antibody), or if an ISV-based drug or Nanobody-based drug is used that carries an ISV or Nanobody at its C-terminal end, this C-terminal epitope is available for (aspecific) interaction with other proteins, and again without being limited to any hypothesis or explanation, it is assumed that this C-terminal region may now be accessible to undergo an (aspecific) protein interaction with one or more proteins that are pre-existing in the "test sample" (for example, one or more IgG's) to be tested and that this may cause protein interference and/or aspecific signals in the immunoassays (and in particular in ADA assays).

As mentioned, the methods described herein can be used to predict, reduce or avoid such protein interaction, and can also be used as a tool to guide modification to the ISV, Nanobody, ISV-based drug or Nanobody-based drug so as to provide the same with a (partially or preferably essentially fully) reduced tendency to give rise to such protein interference.

As will be clear from the preceding paragraph, and again without being limited to any hypothesis or explanation, it is in particular expected (and part of the teaching of the present invention) that (certain) modifications to the "C-terminal region" will alter (and preferably reduce) the tendency of an ISV to undergo such aspecific protein interaction, and this is also what is observed experimentally (see for example the experimental results presented in Examples 1C and 3 below).

Based on this, and again without being limited to any hypothesis or explanation, the present invention also teaches certain modifications that can be introduced for this purpose in the C-terminal region of an ISV, Nanobody, ISV-based drug or Nanobody-based drug (of which the (potential) effectiveness can be tested using the methods described herein). Also, based on the teaching herein, it is envisaged that the skilled person will be able to choose, design or propose other (candidate) modifications to the C-terminal region that could be introduced for this purpose (and of which the (potential) effectiveness can again be tested using the methods described herein).

Returning to the analytical antibody used in the invention, this is preferably a (polyclonal or monoclonal) antibody that recognizes the C-terminal region (as defined above) of an ISV, and in particular but without limitation the C-terminal region of a Nanobody.

For example, in one specific but non-limiting aspect, the "analytical antibody" may be a polyclonal or monoclonal that recognizes (and/or is capable of binding to, and in particular of specific binding to) the C-terminal region of an ISV or Nanobody of which the C-terminal end of the sequence ends with VTVSS (SEQ ID NO:33), but does not recognize (and/or is not capable of specific binding to) the C-terminal region of an ISV or Nanobody (which may be a different ISV but is preferably the same ISV) when there are one or more further amino acid residues (such as 1 to 5 amino acid residues, or alternatively a small peptide sequence or even another polypeptide or protein) linked to the C-terminal VTVSS (SEQ ID NO:33).

In another, more specific but still non-limiting aspect, the "analytical antibody" may be a polyclonal or monoclonal that recognizes (and/or is capable of binding to, and in particular of specific binding to) the C-terminal region of an ISV or Nanobody of which the C-terminal end of the sequence ends with VTVSS (SEQ ID NO:33) and in which position 14 is an amino acid that does not naturally occur at position 14 and/or has been modified compared to the amino acid that naturally occurs at position 14 (for example as a result of humanization, camelization and/or sequence optimization), but that does not recognize (and/or is not capable of specific binding to) the C-terminal region of an ISV or Nanobody (which may be a different ISV but is preferably the same ISV) in which there are one or more further amino acid residues (such as 1 to 5 amino acid residues, or alternatively a small peptide sequence or even another polypeptide or protein) linked to the C-terminal VTVSS (SEQ ID NO:33); and/or in which position 14 is an amino acid that naturally occurs at position 14 (for example alanine or, when the ISV naturally contains a proline at position 14, proline).

For example, the "analytical antibody" may also be a polyclonal or monoclonal that recognizes (and/or is capable of binding to, and in particular of specific binding to) the C-terminal region of an ISV or Nanobody of which the C-terminal end of the sequence ends with VTVSS (SEQ ID NO:33) and in which position 14 is proline (and in particular when position 14 has been modified to proline, for example as a result of humanization, camelization and/or sequence optimization), but does not recognize the C-terminal region of an ISV or Nanobody (which may be a different ISV but is preferably the same ISV) in which there are one or more further amino acid residues (such as 1 to 5 amino acid residues, or alternatively a small peptide sequence or even another polypeptide or protein) linked to the C-terminal VTVSS (SEQ ID NO:33); and/or in which position 14 is alanine.

The "analytical antibody" may also be a polyclonal or monoclonal that recognizes (and/or is capable of binding to, and in particular of specific binding to) the C-terminal region of an ISV or Nanobody of which the C-terminal end of the sequence ends with VTVSS (SEQ ID NO:33) and in which position 14 is proline (in particular where a proline residue naturally occurs at said position in said ISV), but does not recognize the C-terminal region of an ISV or Nanobody (which may be a different ISV but is preferably the same ISV) in which there are one or more further amino acid residues (such as 1 to 5 amino acid residues, or alternatively a small peptide sequence or even another polypeptide or protein) linked to the C-terminal VTVSS (SEQ ID NO:33) in which position 14 is still a (naturally occurring or unmodified) proline.

The "analytical antibody" may also for example be a polyclonal or monoclonal that recognizes (the C-terminal region of) the sequence of the ISV called "Nb 3.4" herein (SEQ ID NO: 5) but does not recognize (the C-terminal region of) the sequence of the ISV called "Nb 3.1" herein (SEQ ID NO: 3) and/or (and preferably and) does not recognize the sequence of the ISV called "Nb 3.2" herein (SEQ ID NO: 4).

For the above purpose, whether an "analytical antibody" does (or does not) recognize an ISV or Nanobody (and/or is or is not capable of (specifically) binding to an ISV or Nanobody) can be determined using any suitable binding assay (such as Biacore), but may also be determined using either the BIACORE assay described in example 3 or an ADA assay such as the ADA bridging/competition assay described in Example 5 (See also FIG. 1A to 1C and in particular FIG. 1B).

Suitable formats/techniques for performing such an assay will be clear to the skilled person based on the disclosure herein, and for example include (without limitation):

A colorimetric assay such as ELISA with analytical antibody coated directly or indirectly to the plate and detection of bound ISV with monoclonal or polyclonal anti-ISV antibody. Other useful alternative technologies for this setup include but are not limited to electrochemiluminescence (the MSD platform), Fluorescence (DELFIA, GYROS), and other methods that rely on secondary detection of the bound ISV.

A Surface Plasmon Resonance (such as BIACORE) or other real-time biosensor method (i.e. other than using SPR) with directly or indirectly immobilized analytical antibody and monitoring the binding of subsequently injected/administered ISV. These methods do not need further detection of the hound ISV. A representative method for performing this type is assay is described in Example 3.

Analyzing the competitive behavior of the ISV in a bridging assay (ADA assay) using the analytical antibody instead of ADA containing biological fluid. For the bridging assay one can make use of different technologies such as ELISA, the MSD platform. Representative methods for performing this type are schematically shown in FIGS. 1A to 1C and one specific example of this kind of assay is also described in Example 5.

Any chromatographic method in which the analytical antibody is immobilized on the chromatographic matrix and specific capturing/isolation of ISV from a solution.

Once a suitable analytical antibody has been obtained using one of the methods described herein or in one of the examples (or a method essentially equivalent to the same), said analytical antibody can be used to determine whether a given ISV or Nanobody (or ISV-based or Nanobody-based drug) will give rise to (or has high or increased tendency to give rise to) protein interference (as defined herein), i.e. by performing steps (i) and (ii) described above. As already described herein, this generally involves contacting said ISV, Nanobody, ISV-based drug or Nanobody-based drug with the analytical antibody and determining whether said ISV, Nanobody, ISV-based drug or Nanobody-based drug is recognized by (and/or is bound by, and in particular specifically bound by) said analytical antibody (and in particular whether the C-terminal region of said ISV or Nanobody or of any ISV or Nanobody that forms the C-terminal end of said ISV-based drug or Nanobody-based drug is recognized by said analytical antibody).

This can generally be performed using any suitable technique for determining whether an antigen (in the case, the ISV, Nanobody, ISV-based drug or Nanobody-based drug) is bound by an antibody, and suitable (immune)assay techniques will be clear to the skilled person. Some non-limiting examples are suitable ELISA techniques (including for example sandwich ELISA's); in which, depending on the ELISA format used (as will be clear to the skilled person), either the analytical antibody or the ISV may be coated on the plate and either the analytical antibody or the ISV may be detectably labeled. Other techniques may for example involve the use of a BIAcore instrument (in which again either the analytical antibody or the ISV may be coated on the chip, see for example Example 3). Another alternative may be a competitive bridging assay (as for example exemplified in Example 5), in which the ability is tested of the ISV to compete with another ISV, Nanobody, ISV-based drug or Nanobody-based drug that is known to be bound by the analytical antibody (or visa versa). These and other suitable techniques for determining whether a given ISV, Nanobody, ISV-based drug or Nanobody-based drug is (specifically) bound or recognized by the analytical antibody will be clear to the skilled person based on the disclosure herein.

It will also be clear, based on the disclosure herein, that the present invention (and in particular the analytical antibody used in the present invention) can be used to determine whether or not a given ISV, Nanobody, ISV-based drug or Nanobody-based drug contains an interaction site (such as an interaction site present at or within the C-terminal region, and/or of which the C-terminal region forms part) that is capable of undergoing an (aspecific) protein interaction with one or more proteins or other components that may be present in a biological sample (i.e., a "test sample") obtained from a subject that is to be subjected to an immunoassay such as an ADA assay (in particular, an ADA assay for determining the presence of any ADA's against the ISV, Nanobody, ISV-based drug or Nanobody-based drug). Thus, when an ISV, Nanobody, ISV-based drug or Nanobody-based drug is recognized by the analytical antibody used in the invention, it is very likely that said ISV, Nanobody, ISV-based drug or Nanobody-based drug contains such an (accessible or exposed) interaction site, and thus will have a tendency to give rise to such protein interference (as defined herein) when it is used in such an immunoassay or ADA assay for testing the test sample. As will be clear to the skilled person, this is something that should preferably be avoided, either by selecting/using another ISV, Nanobody, ISV-based drug or Nanobody-based drug if possible, or by modifying the ISV, Nanobody, ISV-based drug or Nanobody-based such that its tendency to such protein interference will be substantially reduced or essentially removed (again, this can be tested using the method and analytical antibody disclosed herein).

As will also be clear to the skilled person based on the disclosure herein, such a modification may for example comprise making one or more modifications (such as amino acid insertions, additions, deletions or substitutions) to the interaction site on the ISV, Nanobody, ISV-based drug or Nanobody-based drug, such that its ability to undergo an (aspecific) protein interaction with one or more proteins or other components that may be present in a test sample will be reduced or removed. Again, this can be performed by limited trial and error by introducing one or more modifications and then testing whether this ability has been reduced or not, again using the method and analytical antibody disclosed herein. For example, one or more such modifications may be introduced, and then the ability of the modified ISV to bind to the analytical antibody may be compared to that of the original/unmodified ISV. Alternatively, using a competitive bridging format (as for example exemplified in Example 5), or using BIAcore (see for example Example 3), the ability of the modified ISV to (still) compete with the original ISV for binding to the analytical antibody may be determined.

Again, and although the invention is not limited to any hypothesis or explanation, based on the experimental evidence that is set out in the examples below, the inventors have found that this interaction site is likely located at/near the C-terminal region (as defined herein) or that said interaction site forms part of the C-terminal region (or that the C-terminal region forms part of this interaction site). This is for example based at least in part on the observation that, if an ISV has a tendency to give rise to such protein interference and has VTVSS (SEQ ID NO:33) as the amino acid residues at its C-terminal end, that attaching either a limited number of amino acid residues (such as 1 to 10, for example 1 to 5, such as 1, 2, 3, 4 or 5), or alternatively a tag or another peptide, protein or other moiety to this C-terminal end will usually substantially reduce or essentially remove said tendency. In some cases, it has been found that even adding 1, 2 or 3 amino acid residues to the C-terminal VTVSS (SEQ ID NO:33) (which may be any suitable amino acid(s) or combination of amino acids, which may each be independently chosen from any naturally occurring amino acids such as those listed in Table A-2 on page 64 of WO 09/138519, for example and without limitation from alanine, glycine, valine, leucine or isoleucine) may already substantially reduce or essentially remove said tendency. This is also in part based on the observation that in some cases, where a VHH naturally contains an alanine residue at position 14 (which as mentioned forms part of the C-terminal region; see FIG. 2), the naturally occurring VHH often does not have (or has a low) tendency to give rise to such protein interference, whereas a corresponding VHH in which said alanine at position 14 has been replaced with a proline residue (for example, for the purposes of humanization or sequence-optimization) can as a result have an increased tendency to give rise to such protein interference (i.e. compared to the VHH with alanine at position 14).

In one aspect, the invention relates to a VHH, a Nanobody (as defined herein, and in particular a humanized VHH or a camelized VH, such as a camelized human VH) or another ISV (or IS V-based drug or Nanobody-based drug with a VHH, Nanobody or other ISV at its C-terminal end) that has been modified (for example, by introducing one or more amino acid substitutions, additions or deletions), and in particular modified in the C-terminal regions (such as by one or more amino acid substitutions or additions in the C-terminal region), such that (i) it has a substantially reduced tendency (such as at least a statistically relevant reduced tendency) to give rise to protein interference (as defined herein); and/or such that (ii) it has, in the method of the invention described herein (such as in the specific assay described in Example 3 or 5), substantially reduced ability to be bound by an analytical antibody as described herein (such as the polyclonal antibody described in Example 2 and used in Examples 3 and 5), in both cases preferably compared to the same VHH, Nanobody or ISV but without the modifications.

Thus, in one aspect, the invention relates to a VHH, a Nanobody (as defined herein, and in particular a humanized VHH or a camelized VH, such as a camelized human VH) or another ISV (or IS V-based drug or Nanobody-based drug with a VHH. Nanobody or other ISV at its C-terminal end) that is a VHH or VII domain (i.e. an ISV that is a VII domain or derived from a VH domain) and/or that has been based on or has been derived from (the amino acid sequence of) a VHH or VH domain, which VHH, Nanobody or ISV comprises the amino acid sequence VTVSS(X)$_n$ (SEQ ID NO:34) at its C-terminal end, in which n is 1 to 10, preferably 1 to 5, such as 1, 2, 3, 4 or 5 (and preferably 1 or 2, such as 1), and in which each X is an (preferably naturally occurring) amino acid residue that is independently chosen (and preferably independently chosen from the group consisting of alanine (A), glycine (G), valine (V), leucine (L) or isoleucine (I); however, as can be seen from the data presented below, other (preferably naturally occurring) amino acid residues or combinations of the aforementioned preferred amino acid residues with other amino acid residues (such as serine, proline, threonine and/or lysine) may also be used). Preferably, said VHH. Nanobody or ISV with the amino acid sequence VTVSS(X)$_n$ (SEQ ID NO:34) at its C-terminal end is such that (i) it has a substantially reduced tendency (such as at least a statistically relevant reduced tendency) to give rise to protein interference (as defined herein); and/or such that (ii) it has, in the method of the invention described herein (such as in the specific assay described in Example 3 or 5), substantially reduced ability to be bound by an analytical antibody as described herein (such as the polyclonal antibody described in Example 2), in both cases preferably compared to the same VHH, Nanobody or ISV but with the amino acid sequence VTVSS (SEQ ID NO:33) at its C-terminal end. Reference is for example made to the assay and data presented in Example 3.

The aforementioned VHH's, Nanobodies or (other) ISVs are preferably such that they have an RU value for binding by 21-4 of less than 500 (determined according to the protocol set out in Example 9, and after adjusting the measured RU value for the molecule It should also be noted that, any time that reference is made in the description herein or in the claims to any C-terminal sequence VTVSS(X)$_n$ (including any of the aspects (a) to (p) above, that according to one specific aspect of the invention, none of the amino acids X is a cysteine residue.

For example, in some preferred aspects, the C-terminal end of the ISV or ISV-containing construct (when this C-terminal end is a VH-derived ISV, VHH or Nanobody) may be:
(a) VTVSS(X)$_n$, in which n=1 and X=Ala;
(b) VTVSS(X)$_n$, in which n=2 and each X=Ala;
(c) VTVSS(X)$_n$, in which n=3 and each X=Ala;
(d) VTVSS(X)$_n$, in which n=2 and at least one X=Ala (with the remaining amino acid residue(s) X being independently chosen from any naturally occurring amino acid but preferably being independently chosen from Val, Leu and/or Ile);
(e) VTVSS(X)$_n$, in which n=3 and at least one X=Ala (with the remaining amino acid residue(s) X being independently chosen from any naturally occurring amino acid but preferably being independently chosen from Val, Leu and/or Ile);
(f) VTVSS(X)$_n$, in which n=3 and at least two X=Ala (with the remaining amino acid residue(s) X being independently chosen from any naturally occurring amino acid but preferably being independently chosen from Val, Leu and/or Ile);
(g) VTVSS(X)$_n$, in which n=1 and X=Gly;
(h) VTVSS(X)$_n$, in which n=2 and each X=Gly;
(i) VTVSS(X)$_n$, in which n=3 and each X=Gly;
(j) VTVSS(X)$_n$, in which n=2 and at least one X=Gly (with the remaining amino acid residue(s) X being independently chosen from any naturally occurring amino acid but preferably being independently chosen from Val, Leu and/or Ile);
(k) VTVSS(X)$_n$, in which n=3 and at least one X=Gly (with the remaining amino acid residue(s) X being independently chosen from any naturally occurring amino acid but preferably being independently chosen from Val, Leu and/or Ile);
(l) VTVSS(X)$_n$, in which n=3 and at least two X=Gly (with the remaining amino acid residue(s) X being independently chosen from any naturally occurring amino acid but preferably being independently chosen from Val, Leu and/or Ile);
(m) VTVSS(X)$_n$, in which n=2 and each X=Ala or Gly;
(n) VTVSS(X)$_n$, in which n=3 and each X=Ala or Gly;
(o) VTVSS(X)$_n$, in which n=3 and at least one X=Ala or Gly (with the remaining amino acid residue(s) X being independently chosen from any naturally occurring amino acid but preferably being independently chosen from Val, Leu and/or Ile); or
(p) VTVSS(X)$_n$, in which n=3 and at least two X=Ala or Gly (with the remaining amino acid residue(s) X being independently chosen from any naturally occurring amino acid but preferably being independently chosen from Val, Leu and/or Ile);
with aspects (a), (b), (c), (g), (h), (i). (m) and (n) being particularly preferred, with aspects in which n=1 or 2 being preferred and aspects in which n=1 being particularly preferred.

It should also be noted that, any time that reference is made in the description herein or in the claims to any C-terminal sequence VTVSS(X)$_n$, (including any of the aspects (a) to (p) above, that according to one specific aspect of the invention, none of the amino acids X is a cysteine residue.

Thus, in one preferred aspect, the invention relates to an immunoglobulin single variable domain (ISV), which is either a Nanobody or an(other) ISV that comprises a VH sequence or is derived from a VH sequence (with Nanobodies being preferred) which has a C-terminal end of the sequence VTVSS(X)$_n$, in which n=1 and X=Ala (or a protein or polypeptide which contains such an ISV (and preferably such a Nanobody) at its C-terminal end).

In another preferred aspect, the invention relates to an immunoglobulin single variable domain (ISV), which is either a Nanobody or an(other) ISV that comprises a VH sequence or is derived from a VH sequence (with Nanobodies being preferred) which has a C-terminal end of the sequence VTVSS(X)$_n$, in which n=2 and each X=Ala (or a protein or polypeptide which contains such an ISV (and preferably such a Nanobody) at its C-terminal end).

In another preferred aspect, the invention relates to an immunoglobulin single variable domain (ISV), which is either a Nanobody or an(other) ISV that comprises a VH sequence or is derived from a VH sequence (with Nanobodies being preferred) which has a C-terminal end of the sequence VTVSS(X)$_n$, in which n=2 and at least one X=Ala (with the remaining amino acid residue(s) X being independently chosen from any naturally occurring amino acid but preferably being independently chosen from Val, Leu and/or Ile) (or a protein or polypeptide which contains such an ISV (and preferably such a Nanobody) at its C-terminal end).

In another preferred aspect, the invention relates to an immunoglobulin single variable domain (ISV), which is either a Nanobody or an(other) ISV that comprises a VH sequence or is derived from a VH sequence (with Nanobodies being preferred) which has a C-terminal end of the sequence VTVSS(X)$_n$, in which n=3 and at least one X=Ala (with the remaining amino acid residue(s) X being independently chosen from any naturally occurring amino acid but preferably being independently chosen from Val, Leu and/or Ile) (or a protein or polypeptide which contains such an ISV (and preferably such a Nanobody) at its C-terminal end).

In another preferred aspect, the invention relates to an immunoglobulin single variable domain (ISV), which is either a Nanobody or an(other) ISV that comprises a VH sequence or is derived from a VII sequence (with Nanobodies being preferred) which has a C-terminal end of the sequence VTVSS(X)$_n$, in which n=3 and at least two X=Ala (with the remaining amino acid residue(s) X being independently chosen from any naturally occurring amino acid but preferably being independently chosen from Val, Leu and/or Ile) (or a protein or polypeptide which contains such an ISV (and preferably such a Nanobody) at its C-terminal end).

In another preferred aspect, the invention relates to an immunoglobulin single variable domain (ISV), which is either a Nanobody or an(other) ISV that comprises a VH sequence or is derived from a VH sequence (with Nanobodies being preferred) which has a C-terminal end of the sequence VTVSS(X)$_n$, in which n=3 and each X=Ala (or a protein or polypeptide which contains such an ISV (and preferably such a Nanobody) at its C-terminal end).

In another preferred aspect, the invention relates to an immunoglobulin single variable domain (ISV), which is either a Nanobody or an(other) ISV that comprises a VH sequence or is derived from a VH sequence (with Nanobodies being preferred) which has a C-terminal end of the sequence VTVSS(X)$_n$, in which n=1 and X=Gly (or a protein or polypeptide which contains such an ISV (and preferably such a Nanobody) at its C-terminal end).

In another preferred aspect, the invention relates to an immunoglobulin single variable domain (ISV), which is either a Nanobody or an(other) ISV that comprises a VH sequence or is derived from a VH sequence (with Nanobodies being preferred) which has a C-terminal end of the sequence VTVSS(X)$_n$, in which n=2 and each X=Gly (or a protein or polypeptide which contains such an ISV (and preferably such a Nanobody) at its C-terminal end).

In another preferred aspect, the invention relates to an immunoglobulin single variable domain (ISV), which is either a Nanobody or an(other) ISV that comprises a VH sequence or is derived from a VH sequence (with Nanobodies being preferred) which has a C-terminal end of the sequence VTVSS(X)$_n$, in which n=3 and each X=Gly (or a protein or polypeptide which contains such an ISV (and preferably such a Nanobody) at its C-terminal end).

In another preferred aspect, the invention relates to an immunoglobulin single variable domain (ISV), which is either a Nanobody or an(other) ISV that comprises a VH sequence or is derived from a VH sequence (with Nanobodies being preferred) which has a C-terminal end of the sequence VTVSS(X)$_n$, in which n=2 and at least one X=Gly (with the remaining amino acid residue(s) X being independently chosen from any naturally occurring amino acid but preferably being independently chosen from Val, Leu and/or Ile) (or a protein or polypeptide which contains such an ISV (and preferably such a Nanobody) at its C-terminal end).

In another preferred aspect, the invention relates to an immunoglobulin single variable domain (ISV), which is either a Nanobody or an(other) ISV that comprises a VH sequence or is derived from a VH sequence (with Nanobodies being preferred) which has a C-terminal end of the sequence VTVSS(X)$_n$, in which n=3 and at least one X=Gly (with the remaining amino acid residue(s) X being independently chosen from any naturally occurring amino acid but preferably being independently chosen from Val, Leu and/or Ile) (or a protein or polypeptide which contains such an ISV (and preferably such a Nanobody) at its C-terminal end).

In another preferred aspect, the invention relates to an immunoglobulin single variable domain (ISV), which is either a Nanobody or an(other) ISV that comprises a VH sequence or is derived from a VH sequence (with Nanobodies being preferred) which has a C-terminal end of the sequence VTVSS(X)$_n$, in which n=3 and at least two X=Gly (with the remaining amino acid residue(s) X being independently chosen from any naturally occurring amino acid but preferably being independently chosen from Val, Leu and/or Ile) (or a protein or polypeptide which contains such an ISV (and preferably such a Nanobody) at its C-terminal end).

In another preferred aspect, the invention relates to an immunoglobulin single variable domain (ISV), which is either a Nanobody or an(other) ISV that comprises a VH sequence or is derived from a VH sequence (with Nanobodies being preferred) which has a C-terminal end of the sequence VTVSS(X)$_n$, in which n=2 and each X=Ala or Gly (or a protein or polypeptide which contains such an ISV (and preferably such a Nanobody) at its C-terminal end).

In another preferred aspect, the invention relates to an immunoglobulin single variable domain (ISV), which is either a Nanobody or an(other) ISV that comprises a VH sequence or is derived from a VH sequence (with Nanobodies being preferred) which has a C-terminal end of the sequence VTVSS(X)$_n$, in which n=3 and each X=Ala or Gly (or a protein or polypeptide which contains such an ISV (and preferably such a Nanobody) at its C-terminal end).

In another preferred aspect, the invention relates to an immunoglobulin single variable domain (ISV), which is either a Nanobody or an(other) ISV that comprises a VH sequence or is derived from a VH sequence (with Nanobodies being preferred) which has a C-terminal end of the sequence VTVSS(X)$_n$, in which n=3 and at least one X=Ala or Gly (with the remaining amino acid residue(s) X being independently chosen from any naturally occurring amino acid but preferably being independently chosen from Val, Leu and/or Ile) (or a protein or polypeptide which contains such an ISV (and preferably such a Nanobody) at its C-terminal end). or In another preferred aspect, the invention relates to an immunoglobulin single variable domain (ISV), which is either a Nanobody or an(other) ISV that comprises a VH sequence or is derived from a VH sequence (with Nanobodies being preferred) which has a C-terminal end of the sequence VTVSS(X)$_n$, in which n=3 and at least two X=Ala or Gly (with the remaining amino acid residue(s) X being independently chosen from any naturally occurring amino acid but preferably being independently chosen from Val, Leu and/or Ile) (or a protein or polypeptide which contains such an ISV (and preferably such a Nanobody) at its C-terminal end).

In another preferred aspect, the invention relates to an immunoglobulin single variable domain (ISV), which is either a Nanobody or an(other) ISV that comprises a VH sequence or is derived from a VH sequence (with Nanobodies being preferred) which has a C-terminal end of the sequence VTVSS(X)$_n$, in which n=1, 2 or 3 in which each X=Ala or Gly.

In another preferred aspect, the invention relates to an immunoglobulin single variable domain (ISV), which is either a Nanobody or an(other) ISV that comprises a VH sequence or is derived from a VH sequence (with Nanobodies being preferred) which has a C-terminal end of the sequence VTVSS(X)$_n$, in which:
  n=1, 2 or 3 in which each X=Ala or Gly; or
  n=2 or 3 in which all but one X=Ala or Gly (with the remaining amino acid residue X being independently chosen from any naturally occurring amino acid but preferably being independently chosen from Val, Leu and/or Ile)
or a protein or polypeptide which contains such an ISV (and preferably such a Nanobody) at its C-terminal end).

In another preferred aspect, the invention relates to an immunoglobulin single variable domain (ISV), which is either a Nanobody or an(other) ISV that comprises a VH sequence or is derived from a VH sequence (with Nanobodies being preferred) which has a C-terminal end of the sequence VTVSS(X)$_n$, in which:
  n=1, 2 or 3 in which each X=Ala or Gly; or
  n=2 or 3 in which at least one X=Ala or Gly (with the remaining amino acid residue X being independently chosen from any naturally occurring amino acid but preferably being independently chosen from Val, Leu and/or Ile);
  n=2 or 3 in which all but one X=Ala or Gly (with the remaining amino acid residue X being independently chosen from any naturally occurring amino acid but preferably being independently chosen from Val, Leu and/or Ile);
or a protein or polypeptide which contains such an ISV (and preferably such a Nanobody) at its C-terminal end.

In the above aspects, with said (other) "ISV that comprises a VH sequence or is derived from a VH sequence" is meant any ISV that comprises a VH sequence or that is derived from a VH sequence and that is not a Nanobody (i.e. not a VHH, humanized VHH or camelized VH). For example, such (other) ISV may for example be a VH-based (single) domain antibody, VH-based dAb™, or VH-based microbody (see WO 00/29004).

Again, it should be noted that, any time that one of the ISV's referred to herein has a C-terminal sequence VTVSS(X)$_n$, (including without limitation in ISV's referred to in the preceding aspects) that according to one specific aspect of the invention, none of the amino acids X in the sequence VTVSS(X)$_n$ is a cysteine residue.

As further described herein, any such protein or polypeptide may for example be a construct that contains two or more ISV's (such as two or more Nanobodies), optionally linked via one or more suitable linkers. Thus, for example, such a construct may be a bivalent, trivalent, tetravalent or pentavalent construct (such as a bivalent, trivalent, tetravalent or pentavalent Nanobody construct), and may for example be a bivalent, trivalent, tetravalent or pentavalent construct (such as a bivalent, trivalent, tetravalent or pentavalent Nanobody construct) that is bispecific, trispecific or biparatopic construct (including for example monospecific, bispecific or biparatopic constructs that also can bind to serum albumin (preferred) or another serum protein for half-life extension).

Again, the Nanobodies, ISVs and proteins/polypeptides according to each of the aspects described above are preferably such that they have an RU value for binding by 21-4 of less than 500 (determined according to the protocol set out in Example 9, and after adjusting the measured RU value for the molecular weight of the ISV or protein used according to the formula set out above).

As mentioned herein, it is also envisaged that the invention may also be applied to other proteins or polypeptides (and in particular antibody fragments such as Fab fragments or other proteins or polypeptides based on antibody fragments, such as ScFv's) that have a VH-domain at their C-terminal end. Thus, in another aspect, the invention relates to such a protein or polypeptide (such as an ScFv) that has a VH domain at its C-terminal end with the amino acid sequence VTVSS(X)$_n$ (SEQ ID NO:34) at its C-terminal end, in which n is 1 to 10, preferably 1 to 5, such as 1, 2, 3, 4 or 5, and in which each X is an (preferably naturally occurring) amino acid residue that is independently chosen (and preferably independently chosen from the group consisting of alanine (A), glycine (G), valine (V), leucine (L) or isoleucine (I). Again, according to some specific aspects, said C-terminal end may be according to any of (a) to (p) above, and preferably according to one of (a), (b), (c), (g), (h), (i), (m) or (n), with n being 1, 2 or 3 and preferably 1 or 2.

Again, such proteins or polypeptides are preferably such that they have an RU value for binding by 21-4 of less than 500 (determined according to the protocol set out in Example 9, and after adjusting the measured RU value for the molecular weight of the ISV or protein used according to the formula set out above). Also, again, according to one specific aspect of this aspect of the invention, none of the amino acids X in the C-terminal sequence VTVSS(X)$_n$ is a cysteine residue.

The invention further relates to a pharmaceutical composition that comprises an ISV (and preferably a therapeutic ISV) or a protein or polypeptide comprising at least one ISV (and preferably at least one therapeutic ISV), wherein said ISV, protein or polypeptide is as further described herein (i.e. an ISV, protein or polypeptide according to one or more of the aspects described herein, and in particular according to one or more of the aspects described on the preceding pages; and more in particular an ISV, protein or polypeptide that has a C-terminal end/sequence that is according to one or more of the aspects described herein), and at least one suitable carrier, diluent or excipient (i.e. suitable for pharmaceutical use), and optionally one or more further active substances. Such compositions, carriers, diluents or excipients can for example be as described in WO 08/020079 for pharmaceutical compositions that comprise a Nanobody or a protein or polypeptide that comprises at least one Nanobody (and as already mentioned, according to the present invention, the ISV is also preferably a Nanobody).

The invention further relates to an ISV or a protein or polypeptide comprising at least one ISV for use in therapy of a disease in a human being (e.g. a patient in need of such therapy), wherein said ISV, protein or polypeptide is as further described herein (i.e. an ISV, protein or polypeptide according to one or more of the aspects described herein, and in particular according to one or more of the aspects described on the preceding pages; and more in particular an ISV, protein or polypeptide that has a C-terminal end/ sequence that is according to one or more of the aspects described herein).

The invention further relates to the use of an ISV or a protein or polypeptide comprising at least one ISV in the preparation of a pharmaceutical composition, wherein said ISV, protein or polypeptide is as further described herein (i.e. an ISV, protein or polypeptide according to one or more of the aspects described herein, and in particular according to one or more of the aspects described on the preceding pages; and more in particular an ISV, protein or polypeptide that has a C-terminal end/sequence that is according to one or more of the aspects described herein).

The invention further relates to a method of treatment which comprises administering to a human subject (e.g to a patient in need of such treatment) an ISV or a protein or polypeptide comprising at least one ISV in the preparation of a pharmaceutical composition, wherein said ISV, protein or polypeptide is as further described herein (i.e. an ISV, protein or polypeptide according to one or more of the aspects described herein, and in particular according to one or more of the aspects described on the preceding pages; and more in particular an ISV, protein or polypeptide that has a C-terminal end/sequence that is according to one or more of the aspects described herein); or a pharmaceutical composition (as described above) that comprises at least one such ISV, protein or polypeptide.

With respect to the above, it will be clear that the therapeutic use of the ISV's, proteins and polypeptides described herein are a very important aspect of the invention, as such therapeutic use (or the clinical development of such ISV's, proteins and polypeptides for such therapeutic use) may involve the use of ADA assays to determine whether said ISV, protein or polypeptide is immunogenic (i.e. can give rise to ADA's when administered to a human subject). In this respect, it will also be clear that concerns about possible immunogenicity will in particular have to be addressed when a therapeutic is either used for longer periods of time (for during weeks, months or years), and/or has a half-life (preferably expressed as t1/2-beta) in a human subject of at least 3 days, such as at least one week, and up to 10 days or more.

Thus, according to one specific aspect of the invention, a ISV, protein, polypeptide or pharmaceutical composition as described herein is intended for treatment of a chronic disease in a human being, and/or such ISV, protein, polypeptide as described herein is intended to be present in the circulation of the subject (i.e. at pharmacologically active levels) to which it is administered (i.e. at a therapeutically active dose) for at least a period of one week, preferably at least two weeks, such as at least a months; and/or such ISV, protein, polypeptide as described herein is such that it has a half-life (preferably expressed as t1/2-beta) in a human subject of at least 3 days, such as at least one week, and up to 10 days or more; and/or such an ISV, protein, polypeptide or pharmaceutical composition as described herein is intended to be administered to a human being as two or more doses that are administered over a period of at least 3 days, such as at least one week, for example at least two weeks or at least one month, or even longer (i.e. at least 3 months, at least 6 months or at least one year), or even chronically administered.

The invention further relates to a method for (substantially) reducing or essentially removing the tendency of an ISV, a Nanobody or an ISV-based drug or a Nanobody-based drug to give rise to protein interference, said method comprising at least the steps of:

optionally determining the tendency of the ISV, Nanobody, IS V-based drug or Nanobody-based drug to give rise to protein interference, using a method that at least comprises steps (i) and (ii) as referred to herein;

modifying said ISV, Nanobody, ISV-based drug or Nanobody-based drug by introducing one or more one or more amino acid substitutions, additions or deletions in said ISV or Nanobody, or in the C-terminal ISV or Nanobody (if any) of the IS V-based drug or Nanobody-based drug; and in particular by introducing one or more amino acid substitutions or additions in the C-terminal region of said ISV or Nanobody, or in the C-terminal region of the C-terminal ISV or Nanobody (if any) of the ISV-based drug or Nanobody-based drug, for example by adding to the C-terminal end of the sequence 1 to 10, such as 1 to 5, such as 1, 2, 3, 4 or 5 amino acid residues each independently chosen from any naturally occurring amino acids (such as those listed in Table A-2 on page 64 of WO 09/138519, for example and without limitation from alanine, glycine, valine, leucine or isoleucine);

determining the tendency of the so modified ISV, Nanobody, ISV-based drug or Nanobody-based drug to give rise to protein interference, using a method that at least comprises steps (i) and (ii) as referred to herein; optionally in a manner that allows the tendency of the so modified ISV, Nanobody, ISV-based drug or Nanobody-based drug to give rise to protein interference to be compared to the tendency of the original ISV, Nanobody, ISV-based drug or Nanobody-based drug to give rise to protein interference (including, without limitation, comparing them in a competition assay for binding to the analytical antibody as described herein). Alternatively, the method described herein that involves the use of 21-4 may be used.

The invention will now be further described by means of the following non-limiting preferred aspects, examples and figures, in which:

FIG. 1A to 1C schematically show some non-limiting examples of ADA assay formats. Some representative but non-limiting protocols for performing these assays are mentioned in Example 4.

FIG. 2 schematically shows a representative 3D structure of an ISV, such as a Nanobody.

FIG. 9 is a Table showing the sequences used in Example 8 (SEQ ID NO's: 37 to 89) and setting out the corresponding reference sequence.

Figure 1A:
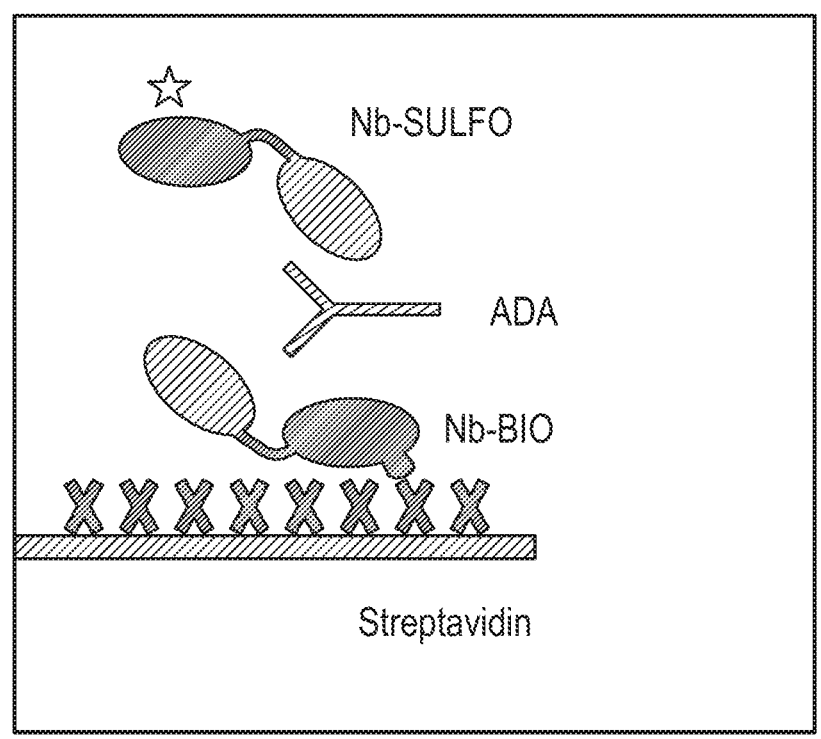

The sequences referred to in the present description and claims are listed in Table A below (SEQ ID NO's: 1 to 37) and in FIG. 9 (SEQ ID NO's: 38 to 89).

TABLE A

| Name | SEQ ID NO: | Sequence |
| --- | --- | --- |
| ISV Ex. 1/2- | 1 | EVQLVESGGGLVQPGGSLRLSCAASGF TFSSYAMSWVRQAPGKGLEWVSGIKSS GDSTRYAGSVKGRFTISRDNAKNTLYL QMNSLRPEDTAVYYCAKSRVSRTGLYT YDNRGQGTLVTVSSGGGGSGGGGSGGG GSGGGGSEVQLVESGGGLVQPGGSLRL SCAASGRTFNNYAMGWFRQAPGKEREF VAAITRSGVRSGVSAIYGDSVKDRFTI SRDNAKNTLYLQMNSLRPEDTAVYYCA ASAIGSGALRRFEYDYSGQGTLVTVSS |
| Alt. ISV | 2 | EVQLVESGGGLVQPGGSLRLSCAASGF TFSSYPMGWFRQAPGKGREFVSSITGS GGSTYYADSVKGRFTISRDNAKNTLYL QMNSLRPEDTAVYYCAAYIRPDTYLSR DYRKYDYWGQGTLVTVSSGGGGSGGGS EVQLVESGGGLVQPGNSLRLSCAASGF TFSSFGMSWVRQAPGKGLEWVSSISGS GSDTLYADSVKGRFTISRDNAKTTLYL QMNSLRPEDTAVYYCTIGGSLSRSSQG TLVTVSSGGGGSGGGSEVQLVESGGGL VQPGGSLRLSCAASGFTFSSYPMGWFR QAPGKGREFVSSITGSGGSTYYADSVK GRFTISRDNAKNTLYLQMNSLRPEDTA VYYCAAYIRPDTYLSRDYRKYDYWGQG TLVTVSS |
| >Nb3.1 | 3 | EVQLVESGGGLVQAGGSLRLSCAASRS IGRLDRMGWYRHRTGEPRELVATITGG SSINYGDFVKGRFTISIDNAKNTVYLQ MNNLKPEDTAVYYCNFNKYVTSRDTWG QGTQVTVSS |
| >Nb3.2 | 4 | EVQLVESGGGLVQAGGSLRLSCAASRS IGRLDRMGWYRHRTGEPRELVATITGG SSINYGDFVKGRFTISIDNAKNTVYLQ MNNLKPEDTAVYYCNFNKYVTSRDTWG QGTQVTVSSAAAEQKLISEEDLNGAAH HHHHH |
| >Nb3.4 | 5 | EVQLVESGGGLVQPGGSLRLSCAASRS IGRLDRMGWYRHRPGEPRELVATITGG SSINYGDSVKGRFTISIDNSKNTVYLQ MNSLRPEDTAVYYCNFNKYVTSRDTWG QGTLVTVSS |
| >Nb3.5 | 6 | HHHHHHEVQLVESGGGLVQPGGSLRLS CAASRSIGRLDRMGWYRHRPGEPRELV ATITGGSSINYGDSVKGRFTISIDNSK NTVYLQMNSLRPEDTAVYYCNFNKYVT SRDTWGQGTLVTVSSAA |
| >Nb3.6 | 7 | HHHHHHEVQLVESGGGLVQPGGSLRLS CAASRSIGRLDRMGWYRHRPGEPRELV ATITGGSSINYGDSVKGRFTISIDNSK NTVYLQMNSLRPEDTAVYYCNFNKYVT SRDTWGQGTLVTVSSA |
| >Nb3.7 | 8 | HHHHHHEVQLVESGGGLVQPGGSLRLS CAASRSIGRLDRMGWYRHRPGEPRELV ATITGGSSINYGDSVKGRFTISIDNSK NTVYLQMNSLRPEDTAVYYCNFNKYVT SRDTWGQGTLVTVSSG |
| >Nb3.8 | 9 | HHHHHHEVQLVESGGGLVQPGGSLRLS CAASRSIGRLDRMGWYRHRPGEPRELV ATITGGSSINYGDSVKGRFTISIDNSK NTVYLQMNSLRPEDTAVYYCNFNKYVT SRDTWGQGTLVTVSSGG |
| >Nb3.9 | 10 | HHHHHHEVQLVESGGGLVQPGGSLRLS CAASRSIGRLDRMGWYRHRPGEPRELV ATITGGSSINYGDSVKGRFTISIDNSK NTVYLQMNSLRPEDTAVYYCNFNKYVT SRDTWGQGTLVTVSSGGG |
| >Nb3.10 | 11 | HHHHHHEVQLVESGGGLVQAGGSLRLS CAASRSIGRLDRMGWYRHRPGEPRELV ATITGGSSINYGDSVKGRFTISIDNSK NTVYLQMNSLRPEDTAVYYCNFNKYVT SRDTWGQGTLVTVSS |

TABLE A-continued

| Name | SEQ ID NO: | Sequence |
|---|---|---|
| >Nb3.11 | 12 | HHHHHHEVQLVESGGGLVQPGGSLRLSCAASRSIGRLDRMGWYRHRPGEPRELVATITGGSSINYGDSVKGRFTISIDNSKNTVYLQMNSLKPEDTAVYYCNFNKYVTSRDTWGQGTLVTVSS |
| >Nb3.12 | 13 | HHHHHHEVQLVESGGGLVQAGGSLRLSCAASRSIGRLDRMGWYRHRPGEPRELVATITGGSSINYGDSVKGRFTISIDNSKNTVYLQMNSLRPEDTAVYYCNFNKYVTSRDTWGQGTQVTVSS |
| >Nb3.13 | 14 | HHHHHHEVQLVESGGGLVQPGGSLRLSCAASRSIGRLDRMGWYRHRPGEPRELVATITGGSSINYGDSVKGRFTISIDNSKNTVYLQMNSLRPEDTAVYYCNFNKYVTSRDTWGQGTQVTVSS |
| >Nb3.14 | 15 | HHHHHHEVQLVESGGGLVQPGGSLRLSCAASRSIGRLDRMGWYRHRPGEPRELVATITGGSSINYGDSVKGRFTISIDNSKNTVYLQMNSLRPEDTAVYYCNFNKYVTSRDTWGQGTLVQVSS |
| >Nb3.15 | 16 | HHHHHHEVQLVESGGGSVQPGGSLRLSCAASRSIGRLDRMGWYRHRPGEPRELVATITGGSSINYGDSVKGRFTISIDNSKNTVYLQMNSLRPEDTAVYYCNFNKYVTSRDTWGQGTLVTVSS |
| >Nb4.1 | 17 | EVQLVESGGGLVQPGGSLRLSCAASGSVFKINVMAWYRQAPGKGRELVAGIISGGSTSYADSVKGRFTISRDNAKNTLYLQMNSLRPEDTAVYYCAFITTESDYDLGRRYWGQGTLVTVSS |
| >Nb4.2 | 18 | EVQLVESGGGLVQPGGSLRLSCAASGSVFKINVMAWYRQAPGKGRELVAGIISGGSTSYADSVKGRFTISRDNAKNTLYLQMNSLRPEDTAVYYCAFITTESDYDLGRRYWGQGTLVTVSSGGGGSGGGSRDWDFDVFGGGTPVGG |
| >Nb6.1 | 19 | EVQLVESGGGLVQPGGSLRLSCIASGLPFSTKSMGWFRQAPGKEREFVARISPGGTSRYYGDFVKGRFAISRDNAKTTWLQMNSLKAEDTAVYYCASGERSTYIGSNYYRTNEYDYWGTGTQVTVSSAAAEQKLISEEDLNGAAHHHHHH |
| >Nb6.2 | 20 | EVQLVESGGGLVQPGGSLRLSCIASGLPFSTKSMGWFRQAPGKEREFVARISPGGTSRYYGDFVKGRFAISRDNAKTTWLQMNSLKAEDTAVYYCASGERSTYIGSNYYRTNEYDYWGTGTQVTVSS |
| >Nb6.4 | 21 | EVQLLESGGGLVQPGGSLRLSCAASGLPFSTKSMGWFRQAPGKGREFVSRISPGGTSRYYGDFVKGRFTISRDNSKNTLYLQMNSLRAEDTAVYYCASGERSTYIGSNYYRTNEYDYWGQGTLVTVSSAAAEQKLISEEDLNGAAHHHHHH |
| >Nb6.5 | 22 | EVQLLESGGGLVQPGGSLRLSCAASGLPFSTKSMGWFRQAPGKGREFVSRISPGGTSRYYGDFVKGRFTISRDNSKNTLYLQMNSLRAEDTAVYYCASGERSTYIGSNYYRTNEYDYWGQGTLVTVSS |
| Example 1C: wildtype | 23 | HHHHHHEVQLVESGGGLVQAGGSLRLSCAASGRTFNNYAMGWFRRAPGKEREFVAAITRSGVRSGVSAIYGDSVKDRFTISRDNAKNTLYLQMNSLKPEDTAVYTCAASAIGSGALRRFEYDYSGQGTQVTVSS |
| Example 1C: (A14P) | 24 | HHHHHHEVQLVESGGGLVQPGGSLRLSCAASGRTFNNYAMGWFRRAPGKEREFVAAITRSGVRSGVSAIYGDSVKDRFTISRDNAKNTLYLQMNSLKPEDTAVYTCAASAIGSGALRRFEYDYSGQGTQVTVSS |
| Example 1C: (K83R) | 25 | HHHHHHEVQLVESGGGLVQAGGSLRLSCAASGRTFNNYAMGWFRRAPGKEREFVAAITRSGVRSGVSAIYGDSVKDRFTISRDNAKNTLYLQMNSLRPEDTAVYTCAASAIGSGALRRFEYDYSGQGTQVTVSS |
| Example 1C: (Q108L) | 26 | HHHHHHEVQLVESGGGLVQAGGSLRLSCAASGRTFNNYAMGWFRRAPGKEREFVAAITRSGVRSGVSAIYGDSVKDRFTISRDNAKNTLYLQMNSLKPEDTAVYTCAASAIGSGALRRFEYDYSGQGTLVTVSS |
| Example 1C: (A14P, K83R, Q108L) | 27 | HHHHHHEVQLVESGGGLVQPGGSLRLSCAASGRTFNNYAMGWFRRAPGKEREFVAAITRSGVRSGVSAIYGDSVKDRFTISRDNAKNTLYLQMNSLRPEDTAVYTCAASAIGSGALRRFEYDYSGQGTLVTVSS |
| Example 1c: (A14P, R39Q, K83R, T91Y, Q108L) | 28 | HHHHHHEVQLVESGGGLVQPGGSLRLSCAASGRTFNNYAMGWFRQAPGKEREFVAAITRSGVRSGVSAIYGDSVKDRFTISRDNAKNTLYLQMNSLRPEDTAVYYCAASAIGSGALRRFEYDYSGQGTLVTVSS |
| Example 1C: (A14P, R39Q, K83R, T91Y, Q108L)-1A | 29 | HHHHHHEVQLVESGGGLVQPGGSLRLSCAASGRTFNNYAMGWFRQAPGKEREFVAAITRSGVRSGVSAIYGDSVKDRFTISRDNAKNTLYLQMNSLRPEDTAVYYCAASAIGSGALRRFEYDYSGQGTLVTVSSA |
| Example 1C: (A14P, R39Q, K83R, T91Y, Q108L)-3A | 30 | HHHHHHEVQLVESGGGLVQPGGSLRLSCAASGRTFNNYAMGWFRQAPGKEREFVAAITRSGVRSGVSAIYGDSVKDRFTISRDNAKNTLYLQMNSLRPEDTAVYYCAASAIGSGALRRFEYDYSGQGTLVTVSSAAA |
| Nb3.16 | 31 | DVQLVESGGGLVQPGGSLRLSCAASRSIGRLDRMGWYRHRPGEPRELVATITGGSSINYGDSVKGRFTISIDNSKNTVYLQMNSLRPEDTAVYYCNFNKYVTSRDTWGQGTLVTVSSGGGGSGGGSEVQLVESGGGLVQPGNSLRLSCAASGFTFSSFGMSWVRQAPGKGLEWVSSISGGSDTLYADSVKGRFTISRDNAKTTLYLQMNSLRPEDTAVYYCTIGGSLSRSSQGTLVTVSSGGGGSGGGSEVQLVESGGGLVQPGGSLRLSCAASRSIGRLDRMGWYRHRPGEPRELVATITGGSSINYGDSVKGRFTISIDNSKNTVYLQMNSLRPEDTAVYYCNFNKYVTSRDTWGQGTLVTVSS |
| Nb3.17 | 32 | DVQLVESGGGLVQPGGSLRLSCAASRSIGRLDRMGWYRHRPGEPRELVATITGGSSINYGDSVKGRFTISIDNSKNTVYLQMNSLRPEDTAVYYCNFNKYVTSRDTWGQGTLVTVSSGGGGSGGGSEVQLVESGGGLVQPGNSLRLSCAASGFTFSSFGMSWVRQAPGKGLEWVSSISGGSDTLYADSVKGRFTISRDNAKTTLYLQMNSLRPEDTAVYYCTIGGSLSRSSQGTLVTVSSGGGGSGGGSEVQLVESGGGLVQPGGSLRLSCAASRSIGRLDRMGWYRHRPGEPRELVATITGGSSINYGDSVKGRFTISIDNSKNTVYLQMNSLRPEDTAVYYCNFNKYVTSRDTWGQGTLVTVSSA |
| C-terminal sequence | 33 | VTVSS |

TABLE A-continued

| Name | SEQ ID NO: | Sequence |
|---|---|---|
| C-terminal sequence | 34 | VTVSS(X)$_n$ |
| 21-4-3, IGH consensus | 35 | QIQLVQSGPELKKPGETVKISCKASGY TFTAYSMHWVKQAPGKGLKWMGWINTV TGEPAYADDFKGRFAFSLETSASTAYL QISSLKNEDTATYFCTRGLIHFYYWGQ GTTLTVSSAKTTPPSVYPLAPGSAAQT NSMVTLGCLVKGYFPEPVTVTWNSGSL SSGVHTFPAVLQSDLYTLSSSVTVPSS TWPSETVTCNVAHPASSTKVDKKIVPR DC |
| 21-4-3-IGK consensus | 36 | DIQMTQTPSSLSASLGGRVTITCKASQ DIHNFISWYQHKPGKVPRLIIHDTSTL QPGIPSRFSGSGSGRDYSFSITNLEPE DIATYYCLHYDNLLRSFGGGTKLEIKR ADAAPTVSIFPPSSEQLTSGGASVVCF LNNFYPKDINVKWKIDGSERQNGVLNS WTDQDSKDSTYSMSSTLTLTKDEYERH NSYTCEATHKTSTSPIVKSFNRNEC |

EXPERIMENTAL PART

Example 1: Generation of a Polyclonal Analytical Antibody

A polyclonal antibody (IgG fraction) that can be used as the "analytical antibody" was generated as follows:

A. Identification of Suitable Plasma Samples for Isolating the Polyclonal Antibody Twenty plasma samples from healthy individuals that were never treated with an ISV were evaluated for presence of antibodies against ISV that can be used as the analytical antibody in the invention.

The ISV that was initially used in this Example was SEQ ID NO: 1. Subsequently, to confirm that the interaction is not specific for this particular ISV, but is an aspecific protein-protein interaction that may occur with a number of ISV's, the assays below were repeated with other ISV's (see paragraph C) below). As an alternative for SEQ ID NO:1, for example SEQ ID NO:2 may also be used.

The assay used was an ECL (Electrochemiluminescence) based bridging assay that used biotinylated ISV (a biotinylated variant of SEQ ID NO:1) to capture and sulfo-tagged ISV to detect anti-drug antibodies. A similar format is also used for performing ADA assays. Biotinylation and sulfo-tagging of the ISV was done using standard coupling chemistry on primary amines using Sulfo-NHS-LC-Biotin (Pierce) and Sulfo-tag NHS-Ester (MSD), respectively according to the manufacturer's instructions. The plasma samples were diluted 1/5 in PBS/0.1% casein and were incubated for 30 minutes at 37° C., 600 RPM in 96 well polypropylene plates. The samples (50 µL) were then diluted 1/3 in 1:1 mixture (100 µL) of 2 µg/ml biotinylated and 2 µg/ml sulfo-tagged ISV (SEQ ID NO:1) and incubated for 1 hour at RT, 600 RPM. MSD MA®96-well Standard Streptavidin plates were blocked with 150 µL/well Superblock® T20 for 1 hour at RT, then washed 3 times with PBS/0.05% Tween20 (=wash buffer). Sample/1:1 mix (biotinylated and sulfo-tagged ISV (SEQ ID NO:1) (50.0 µL) was transferred from the polypropylene plate to the MSD plate and incubated for 1 hour at RT, 600 rpm. Plates were washed three times prior to addition of 2× Read Buffer (MSD) (150 µL/well) and reading the ECL units (ECLU) on an MSD instrument (Sector Imager 2400 reader). Samples were screened as positive or negative using the screening cut-point determined during method validation. The screening cut-point was calculated based on the background values of 118 individual plasma samples from healthy individuals that were never treated with an ISV, using appropriate statistical analysis as recommended by the guidelines for ADA assay development (Shankar, 2008). A non-parametric assessment was used and the cut-off value was calculated based on the 95$^{th}$ percentile, after exclusion of outliers.

Six plasma samples were clearly scored as positive: IHuP #002-001-ABL-01, IHuP #002-001-ABL-08. IHuP #002-001-ABL-10. IHuP #002-001-ABL-15. IHuP #002-001-ABL-19 and IHuP #002-001-ABL-20 (Table I).

These samples were further analyzed in a drug displacement set-up (confirmatory assay) to confirm the specificity of the positive screening outcome (Table II). Therefore, the samples were diluted 1/5 in PBS/0.1% casein containing 12.5 µg/mL ISV (SEQ ID NO:1) and were incubated for 30 minutes at 37° C., 600 RPM in 96 well polypropylene plates. The samples (50 µL) are then diluted 1/3 in 1:1 mixture (100 µL) of 2 µg/ml biotinylated and 2 µg/ml sulfo-tagged ISV (SEQ ID NO:1) and incubated for 1 hour at RT, 600 RPM. Subsequently, sample/1:1 mix (biotinylated and sulfo-tagged ISV) (50.0 µL) was transferred from the polypropylene plate to the blocked MSD MA® 96-well Standard Streptavidin plate as described above for the screening assay and incubated for 1 hour at RT, 600 rpm. Plates were washed three times prior to addition of 2× Read Buffer (MSD) (150 µL/well) and measuring ECL units (ECLU) on an MSD instrument (Sector Imager 2400 reader). Samples were confirmed as true positives using the confirmatory cut-point determined during method validation and was calculated on the ECL response of 118 individual plasma samples from healthy individuals that were never treated with ISV, that were spiked with 50 µg/ml ISV (SEQ ID NO:1) using appropriate statistical analysis as recommended by the guidelines for ADA assay development (Shankar, 2008). A minimal signal reduction of 50% was calculated based on the 99% confidence interval.

Samples that were positive in the ECL based bridging assay and that were confirmed as positive in the drug displacement set-up assay were selected as a source for generating the polyclonal antibody using affinity chromatography.

TABLE I screening results of 20 plasma samples in the ADA ISV assay.

| Sample ID | ECLU screening assay |
|---|---|
| IHuP#002-001-ABL-01 | 13081 |
| IHuP#002-001-ABL-02 | 56 |
| IHuP#002-001-ABL-03 | 272 |
| IHuP#002-001-ABL-04 | 125 |
| IHuP#002-001-ABL-05 | 70 |
| IHuP#002-001-ABL-06 | 99 |
| IHuP#002-001-ABL-07 | 170 |
| IHuP#002-001-ABL-08 | 659358 |
| IHuP#002-001-ABL-09 | 798 |
| IHuP#002-001-ABL-10 | 1101 |
| IHuP#002-001-ABL-11 | 83 |
| IHuP#002-001-ABL-12 | 72 |
| IHuP#002-001-ABL-13 | 403 |
| IHuP#002-001-ABL-14 | 62 |
| IHuP#002-001-ABL-15 | 1141 |
| IHuP#002-001-ABL-16 | 159 |
| IHuP#002-001-ABL-17 | 72 |

TABLE I-continued screening results of 20 plasma samples in the ADA ISV assay.

| Sample ID | ECLU screening assay |
|---|---|
| IHuP#002-001-ABL-18 | 170 |
| IHuP#002-001-ABL-19 | 4503 |
| IHuP#002-001-ABL-20 | 8243 |

TABLE II

Confirmation of positively screened plasma samples in the confirmatory assay. A confirmatory cut-point of 50% was used for evaluation of the results. One sample was not confirmed as a true positive sample

| Plasma sample ID | ECLU screening assay: plasma | ECLU confirmatory assay: plasma | % signal inhibition |
|---|---|---|---|
| IHuP#002-001-ABL-01 | 13081 | 685 | 95 |
| IHuP#002-001-ABL-08 | 659358 | 169410 | 74 |
| IHuP#002-001-ABL-10 | 1101 | 582 | 47 |
| IHuP#002-001-ABL-15 | 1141 | 467 | 59 |
| IHuP#002-001-ABL-19 | 4503 | 1531 | 66 |
| IHuP#002-001-ABL-20 | 8243 | 1450 | 82 |

A further three serum samples from individuals that not have been treated with an ISV were also evaluated using the ECL based bridging assay described above and confirmed using the drug displacement set-up assay.

Two serum samples were clearly scored as positive in the ECL based bridging assay: IHUS #B09032311A3 and IHUS #B09032311A20 (Table III). The 2 positively screened samples were further analyzed in the drug displacement set-up to confirm the specificity of the positive screening outcome.

TABLE III

Screening and confirmatory results of 3 serum samples and corresponding IgG purified fraction

| Serum sample ID | ECL signal screening assay: serum | ECL signal confirmatory assay: serum | % signal inhibition | ECL signal screening assay: IgG | ECL signal confirmatory assay: IgG | % signal inhibition |
|---|---|---|---|---|---|---|
| IHUS#B09032311A3 | 2388 | 286 | 88% | 3716 | 370 | 90% |
| IHUS#B09032311A20 | 19272 | 915 | 95% | 31309 | 1160 | 96% |
| IHUS#B09032311A1 | 62 | | | | | |

B. Generation of Purified Polyclonal IgG Fraction.

A polyclonal IgG was purified from the samples IHUS #B09032311A3 and IHUS #B09032311A20 (see above) using Protein G HP Spin Trap Columns (GE Healthcare) according to the manufacturer's instructions. In short, after removal of the storage solution form the column by centrifugation (30s at 100×g), the column was equilibrated by adding binding buffer (20 mM sodium phosphate, pH 7.0). After centrifugation, the solution containing the desired polyclonal was added (max 1 mg in 600 µl) and column was incubated for 4 min while gently mixing. The column was then centrifuged and washed 2× by successive addition of binding buffer (600 µl) and centrifugation. After addition of 400 µl elution buffer (0.1 M glycine-HCL, pH 2.7) and mixing by inversion, the antibody was eluted by centrifugation in 30 µl neutralization buffer (1M Tris-HCL, pH 9.0).

In order to confirm that the IgG fraction thus obtained was involved in aspecific binding to the ISV(s), the purified IgG antibody was analyzed in the ECL based bridging assay described above and confirmed using the drug displacement set-up assay used under A) above. In both samples (IHUS #B09032311A3 and IHUS #B09032311A20), purified IgG antibody was confirmed to be involved in the aspecific binding leading to a positive signal in the assays (Table III). This confirmed that the purified polyclonal IgG could be used as an "analytical antibody", and it was used as such in (the assays of) Examples 3 and 5.

C. Aspecific Binding to Other ISV's.

In order to determine whether the protein interference observed is specific for a single ISV, and/or is specific for a particular region, epitope or antigenic determinant on ISV's, and/or for certain mutations made to wildtype ISV's (such as one or more humanizing mutations), the ECL based bridging assay and the drug displacement set-up assay (both as described under A) above, with SEQ ID NO: 1 being used as the sulfo-tagged ISV) were repeated using the plasma samples IHUS #B09032311A3, IHUS #B09032311A20 and IHUS #B09032311A1. As these plasma samples contain the polyclonal "analytical" antibody isolated under B) above, this also provides information on the specificity, selectivity and epitope recognition of the polyclonal analytical antibody.

8 ISV's were tested (SEQ ID NO's 23 to 30, respectively—see Table A above), of which one was a wildtype VHH (SEQ ID NO: 23) and the other 7 ISV's were humanized versions of the wildtype sequence with different humanizing substitutions. Two ISV's (SEQ ID NO's: 29 and 30) also contained additional amino acid residues at the C-terminus (1 and 3 additional alanine residues, respectively).

The data are shown in Table IV. Without being limited to any explanation or hypothesis, it can be seen that changes to the C-terminal region (as defined herein) can apparently strongly influence the extent to which the plasma samples used can give rise to protein interference. For example, it can be seen that adding one or three amino acid residues to the C-terminus can strongly reduce the tendency for protein interference to arise (for example, only 18 and 13% reduction in the ECLU assay with sample IHUS #B09032311A3 for SEQ ID NO's: 29 and 30, compared to 90% reduction for SEQ ID NO: 28, the corresponding humanized variant without any amino acid residues added to the C-terminus). Similarly, introducing a proline residue at position 14 of the wildtype sequence can apparently also strongly influence the extent to which the plasma samples used can give rise to protein interference (for example, only 20% reduction in the ECLU assay with sample IHUS #B09032311A3 for the wildtype sequence of SEQ ID NO's: 23, compared to 91% reduction for SEQ ID NO: 24, the wildtype sequence with an A14P substitution). K83R and Q108L, which are also substitutions close to the C-terminal region, also lead to some increase in the tendency to give rise to protein interference, but not as much as the A14P substitution, and the total combined effect of the A14P+K83R+Q108L substitutions can be negated by adding one or more amino acid residues to the C-terminus (compare again the data for SEQ ID NO's: 29 and 30 with the data for the other humanized variants).

Figure 2:
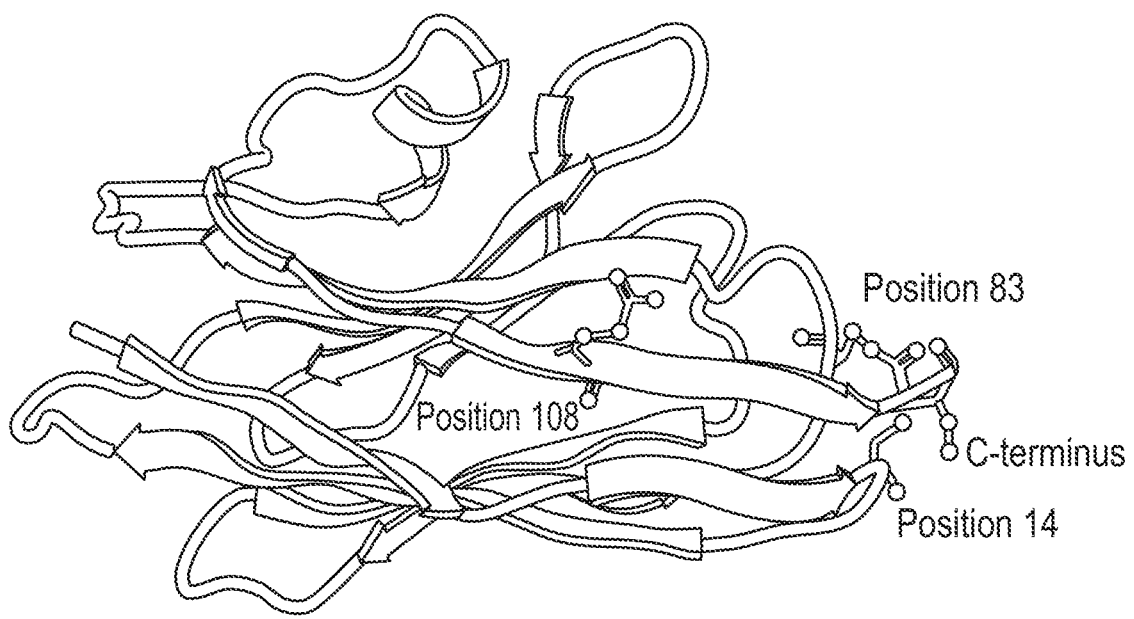

Based on this data, it was also concluded that apparently, the polyclonal analytical antibody recognized the C-terminal region (as defined herein) of ISV's generally. As can be seen from FIG. 2, position 14 (and to a lesser degree positions 83 and 108) also form parts of the C-terminal region of an ISV (when the three-dimensional ternary structure of an ISV is taken into account).

Example 2A: Purification Using Protein a and Affinity Chromatography

In a first step, the IgG antibody fraction was enriched from the serum samples using protein A affinity chromatography. Typical columns that were used for this enrichment included HiTrap MabselectSure and MabSelectXtra (GE Healthcare); PorosMabCapture A (Applied Biosystems). Purification of the IgG antibodies from the serum samples was performed in an automated and similar manner over all experiments. Chromatographic runs were performed on the AKTA purifier systems (GE Healthcare) and logged in real-time using UNICORN protein purification software (GE Healthcare). Briefly, the serum sample was diluted 1:1

TABLE IV

Evaluation of different Nanobody variants as competitor in the ISV ADA assay using the analytical antibody.

| | | Serum sample ID | | | | | |
|---|---|---|---|---|---|---|---|
| | | IHUS#B09032311A3 | | IHUS#B09032311A20 | | IHUS#B09032311A1 | |
| Nanobody Variant (right hand | | ECLU in screening assay (using SEQ ID NO: 1) | | | | | |
| column mentions the humanizing | | 2217 | | 18494 | | 62 | |
| substitutions and C-terminal additions made compared to the wildtype sequence of SEQ ID NO: 23 | | ECLU confirmatory assay | % reduction | ECLU confirmatory assay | % reduction | ECLU confirmatory assay | % reduction |
| SEQ ID NO: 23 | Wildtype VHH | 1778 | 20 | 8682 | 53 | 60 | 4 |
| SEQ ID NO: 24 | Wildtype VHH + A14P | 205 | 91 | 668 | 96 | 56 | 10 |
| SEQ ID NO: 25 | Wildtype VHH + K83R | 1403 | 37 | 6912 | 63 | 62 | 1 |
| SEQ ID NO: 26 | Wildtype VHH + Q108L | 1533 | 31 | 6991 | 62 | 59 | 5 |
| SEQ ID NO: 27 | Wildtype VHH + A14P + K83R + Q108L | 156 | 93 | 628 | 97 | 57 | 8 |
| SEQ ID NO: 28 | Wildtype VHH + A14P + R39Q + K83R + T91Y + Q108L | 228 | 90 | 570 | 97 | 58 | 6 |
| SEQ ID NO: 29 | Wildtype VHH + A14P + R39Q + K83R + T91Y + Q108L + 1 additional A at C-terminus (A114) | 1814 | 18 | 15087 | 18 | 60 | 3 |
| SEQ ID NO: 30 | Wildtype VHH + A14P + R39Q + K83R + T91Y + Q108L + 3 A's at C-terminus (A114 + A115 + A116) | 1933 | 13 | 15244 | 18 | 62 | 0 |

Example 2: Affinity Purification of Analytical Antibody

This Example describes two methods that can be used to isolate from a biological fluid from a human subject an analytical antibody that is able to recognize and/or bind the C-terminal end of an ISV. The antibody is isolated from 4 different serum samples that were characterized in that these induced a positive signal in an ADA assay according to the test as described in Example 1.

Starting from serum samples, each of these protocols provide a purified preparation of interference factor(s) that can be used as the analytical antibody in the methods described herein. These methods can also more generally be used to purify the interference factor(s) for other purposes (for example, the interference factor(s) purified using the protocols below were also used experimentally in Example 8 in order to show that binding to an ISV or ISV-construct by monoclonal 21-4 is predictive for binding of the same ISV or ISV-construct by interference factors, and thus by the tendency of said ISV or ISV-construct to undergo aspecific protein interference in an ADA assay).

with D-PBS (Dulbecco's Phosphate-Buffered Saline) and 0.22 μm filtered before uploading on the column at a fixed flow rate of 0.5 mL/min. The column was washed to remove non-specific binding components over 5 column volumes using D-PBS at a flow rate of 0.5 mL/min. The IgG fraction was eluted by acidic elution, using 100 mM Glycine pH 2.6 buffer, and a flow rate of 0.5 mL/min. After elution, the fractions were neutralized using 1.5 M Tris buffer pH 8.8. SDS-PAGE was run to confirm the isolation of IgG antibodies in the elution.

In a second step, the interfering IgGs were further enriched by applying the protein A purified IgG fraction from the 4 different sera onto ISV coupled affinity columns. More specifically, the interfering IgG were further enriched by binding to a column containing an ISV with sequence of SEQ ID NO: 1. To this, the ISV was covalently linked to Sepharose 4 fast flow (GE Healthcare) using the CNBr (Cyanogen bromide)—coupling method according to the manufacturer's procedure. The affinity purification was performed in an automated and similar manner over all experiments. Chromatographic runs were performed on the AKTA purifier systems and logged in UNICORN. Briefly, the IgG enriched sample (up to 10 mL loading volume) was uploaded on the column at a fixed flow rate of 0.5 mL/min. The column was washed to remove non-specific binding-components over 5 column volumes using D-PBS at a flow rate of 0.5 mL/min. The IS V-binding components were eluted by acidic elution, using 100 mM Glycine pH 2.6 buffer, and a flow rate of 0.5 mL/min. After elution, the fractions were neutralized using 1.5 M Tris buffer pH 8.8. The fractions were analyzed using SDS-PAGE which confirmed the isolation of IgG antibodies in the elution (data not shown).

These fractions were pooled and used for further analyses such as those described in Example 3.

Example 2B: Purification Suing CaptureSelect™ Chromatography

Alternatively, interference factor(s) were recovered from plasma and purified using the commercially available IgA binding affinity resin CaptureSelect hIgA™ (BAC BV), which is based on camelid-derived heavy-chain only variable domains (VHH). The collected 'IgA fraction' containing IgA together with interfering IgG was subsequently loaded onto a protein A column to remove the IgA fraction. The protein A column was processed according to generic IgG purification conditions (running buffer: PBS; elution buffer: 100 mM glycine pH=2.7; post elution neutralization via 1M Tris). The interference factor was recovered from the Prot A elution in >95% yield.

In a variation to this method, another CaptureSelect affinity resin (CaptureSelect Alpha-1 Antitrypsin resin, a VHH based commercially available affinity resin, not targeting any antibody related proteins) was be used. This resin provided a high interference factor binding efficacy and allowed for a selective 2 step elution: antitrypsin via neutral pH elution using 2.0 M MgCl2, followed by the interference factor elution via an acidic step (0.1 M Glycine pH3.0, similar to protein A/G elution conditions; neutralisation using 1.5M Tris). This one step purification yielded up to 15 μg interfering IgG1 per mL high interference plasma, which is approximately 0.3% of the total IgG present. Optionally, the neutralised interference fraction can be desalted and further purified via a Size Exclusion Column equilibrated in D-PBS.

Example 3: Influence of Different ISV Substitutions on the Tendency of ISV to Give Rise to Protein Interference As mentioned in the description above, the present invention makes available certain assays and techniques which make it possible to make an assessment of whether or not a given ISV has a tendency to give rise to protein interference. These include the ECL based bridging assay and the drug displacement set-up assay used in Example 1, as well as the BIACORE assay described in this Example 3 and the bridging/competition ADA assay described in the further Examples below.

As also mentioned in the description above, these assays can also be used to determine whether specific changes (such as amino acid deletions, substitutions or additions) can influence (and preferably reduce) the tendency of a given ISV to give rise to protein interference. Some of these changes will be or become clear to the skilled person based on the disclosure herein and on the experimental data presented in Example 1 and this Example 3.

As already indicated by the data generated in Example 1, it appears that certain mutations in or close to the C-terminal region (as defined herein) of an ISV can (strongly) influence its tendency to give rise to protein interference. For example, adding a few amino acid residues to the C-terminus (such as 1 or 3 alanine residues) appears to strongly reduce the tendency of an ISV to give rise to protein interference, and appears even to be able to negate the presence of other substitutions (for example, in or close to the C-terminal region) which appear to increase the tendency to give rise to protein interference (for example, an A14P substitution).

In this Example 3, both the effect of other substitutions as well as the effect of adding additional amino acids to the C-terminus was investigated by comparing related ISV's with different substitutions, using the analytical polyclonal antibody generated in Example 2. The analysis was done by measuring the kinetics of interaction between each of the ISV's investigated and the analytical polyclonal by means of surface Plasmon resonance (SPR) using the Biacore™ T100 biosensor from GE Healthcare. The ISV tested in this Example 3 were those of SEQ ID NO's 3 to 22 (see Table A above and Table V below).

In a typical experiment, a polyclonal antibody solution was prepared at 10 μg/ml in 10 mM NaOAc pH5.0. This polyclonal antibody was then immobilized on a CM5 sensorchip using amine coupling by the EDC/NHS method (EDC=N-ethyl-N'43-diethylamino-propyl]-carbodiimide; NHS=N-hydroxysuccinimide) according to the manufacturer's procedure. The amount immobilized gave approximately 2700 response units (RU). A fixed concentration of 500 nM of ISV was then injected onto the surface for 120 seconds at a flow rate of 45 μl per minute. Because no efficient regeneration buffer could be identified, the dissociation time was elongated to 2400 seconds. The signal obtained by injecting the ISV onto a blank flow cell was subtracted from the signal obtained by injecting the ISV onto the polyclonal antibody bound flow cell. The blank flow cell was activated/deactivated in a similar way as the flow cell for the polyclonal antibody, but without adding protein. Also, a blank injection (HBS-EP+running buffer (HBS=Hepes Buffered Saline: GE Healthcare) was subtracted to correct for possible baseline drift.

To examine the effect of adding amino acid residues to the C-terminus, the influence of adding 1 or 2 alanines and 1, 2 or 3 glycines was investigated by comparing the binding of ISV with the different additions, using an analytical polyclonal antibody generated as described in example 2. The ISV's generated and tested for this purpose were NB's 3.4 to 3.9 (SEQ ID NO's: 5 to 10).

Figure 3:
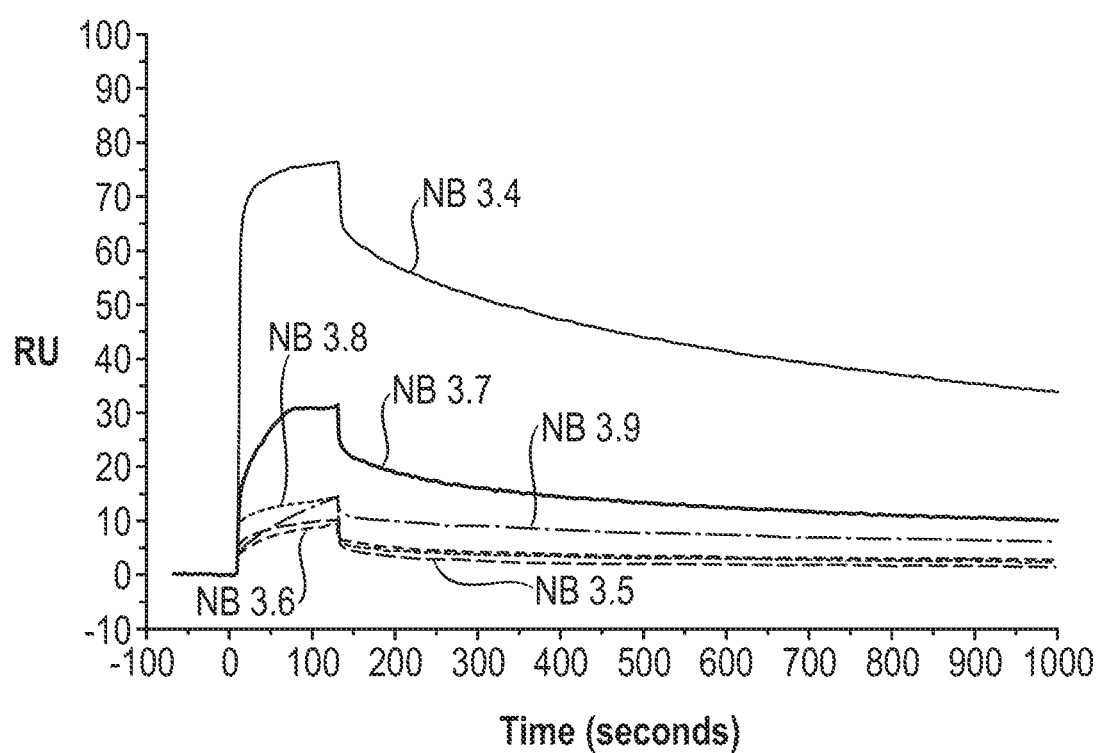
FIG. 3 is a binding curve (obtained using the BIACORE assay described in Example 3) showing the binding of NB's 3.4 to 3.9 (SEQ ID NO's. 5 to 10) to the immobilized polyclonal antibody obtained in Example 2.

As representative examples of the kind of data obtained, FIG. 3 shows the binding of NB's 3.4 to 3.9 to the immobilized polyclonal antibody. Table V summarizes the results obtained.

TABLE V

| Clone ID | SEQ ID NO | Position 113[1] | Position 114[1] | Position 115[1] | Position 116[1] | Binding** (RU) |
|---|---|---|---|---|---|---|
| NB 3.4 | 5 | S | | | | 75 |
| NB 3.5 | 6 | S | A | | | 9 |
| NB 3.6 | 7 | S | A | A | | 8 |
| NB 3.7 | 8 | S | G | | | 31 |
| NB 3.8 | 9 | S | G | G | | 13 |
| NB 3.9 | 10 | S | G | G | G | 13 |

**Binding signal obtained at the end of injection (=maximal RU signal)
[1]In this numbering, position 113 is the last "S" of the C-terminal VTVSS motif, and positions 114, 115 and 116 are the positions immediately following (downstream) of said position 113.

To examine the effect of (other) substitutions in the C-terminal region, the influence of different substitutions was investigated by comparing related ISV's containing these substitutions, using the same analytical polyclonal antibody as described above. The analysis was done as described above.

The ISVs containing said substitutions that were tested were NB's 3.1, 3.2 and 3.4 (SEQ ID NO's 3, 4 and 5); NB's 3.10 to 3.15 (SEQ ID NO's 11 to 16), which were compared with NB 3.4; NB's 4.1 and 4.2 (SEQ ID NO's 17 and 18) and NB's 6.1, 6.2, 6.4 and 6.5 (SEQ ID NO's 19 to 22).

Figure 4:
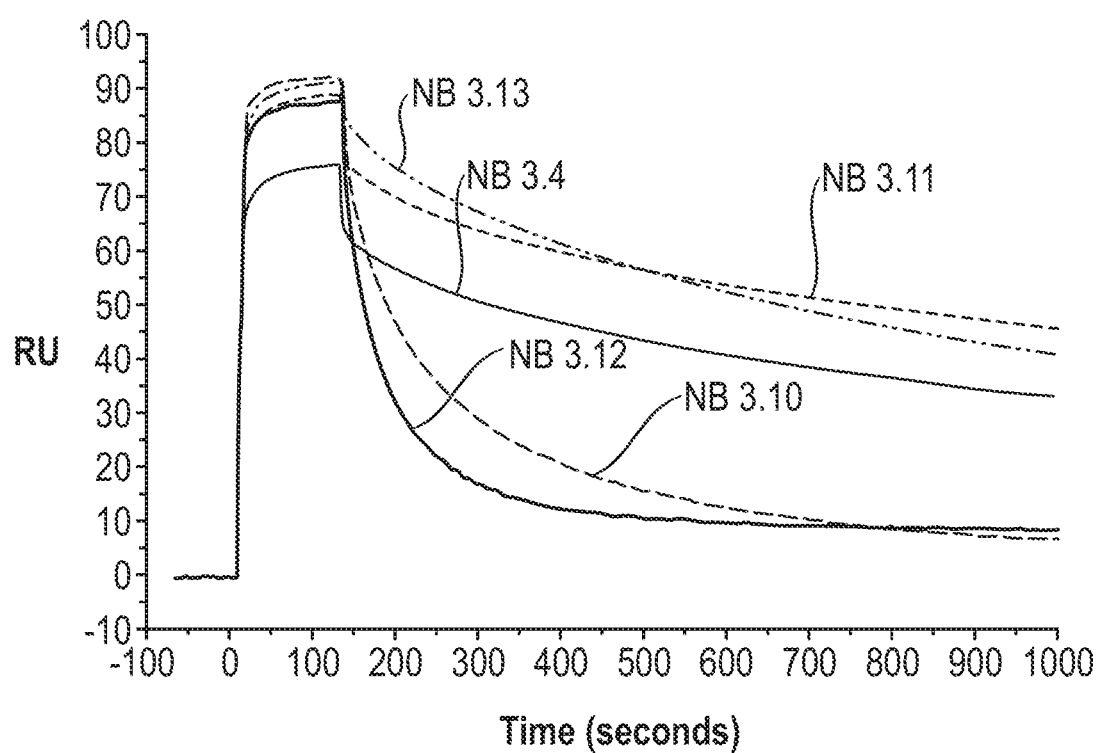
FIG. 4 is a binding curve (obtained using the BIACORE assay described in Example 3) showing the binding of NB's 3.4, 3.11, 3.12 and 3.13 (SEQ ID NO's: 5, 12, 13 and 14) to the immobilized polyclonal antibody obtained in Example 2.
Figure 5:
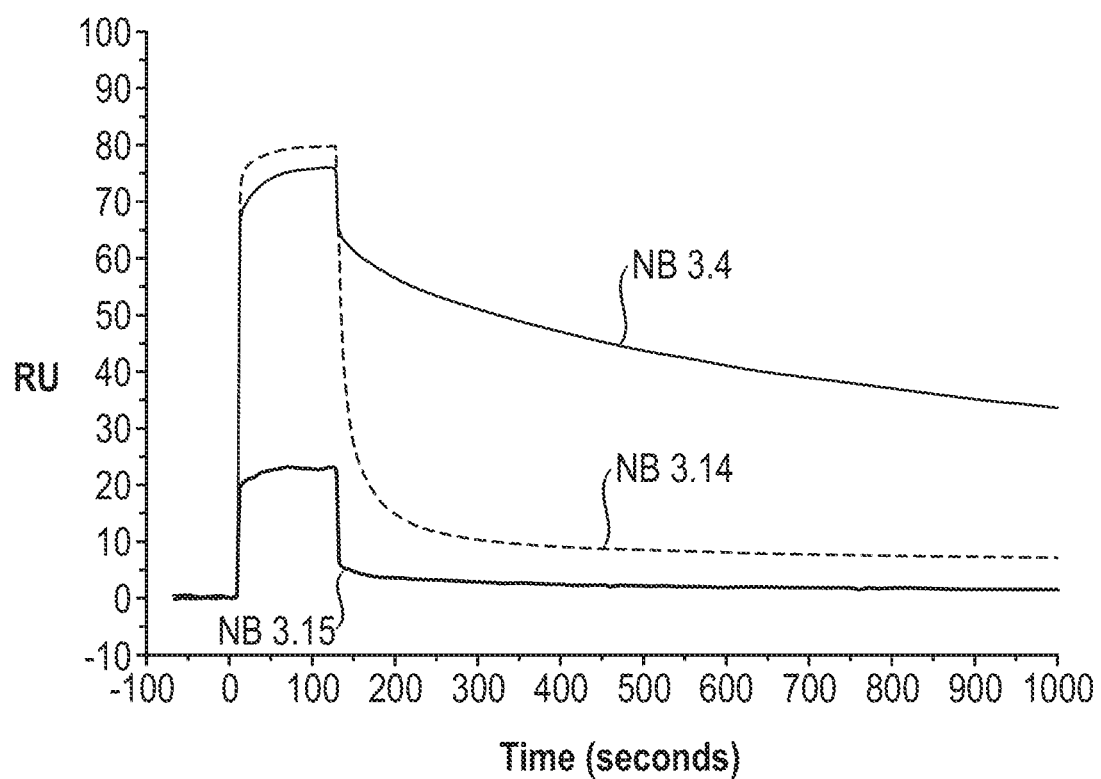
FIG. 5 is a binding curve (obtained using the BIACORE assay described in Example 3) showing the binding of NB's 3.4, 3.14 and 3.15 (SEQ ID NO's: 5, 15 and 16) to the immobilized polyclonal antibody obtained in Example 2.
Figure 6:
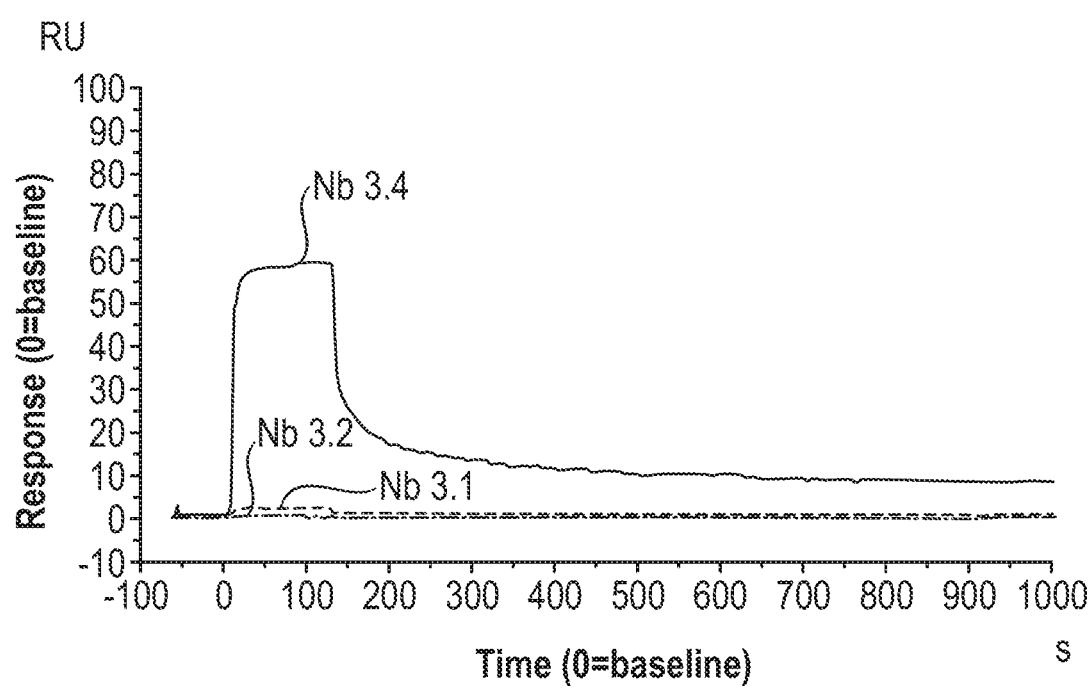
FIG. 6 is a binding curve (obtained using the BIACORE assay described in Example 3) showing the binding of NB's 3.1, 3.2 and 3.4 (SEQ ID NO's: 3, 4 and 5) to the immobilized polyclonal antibody obtained in Example 2.
Figure 7:
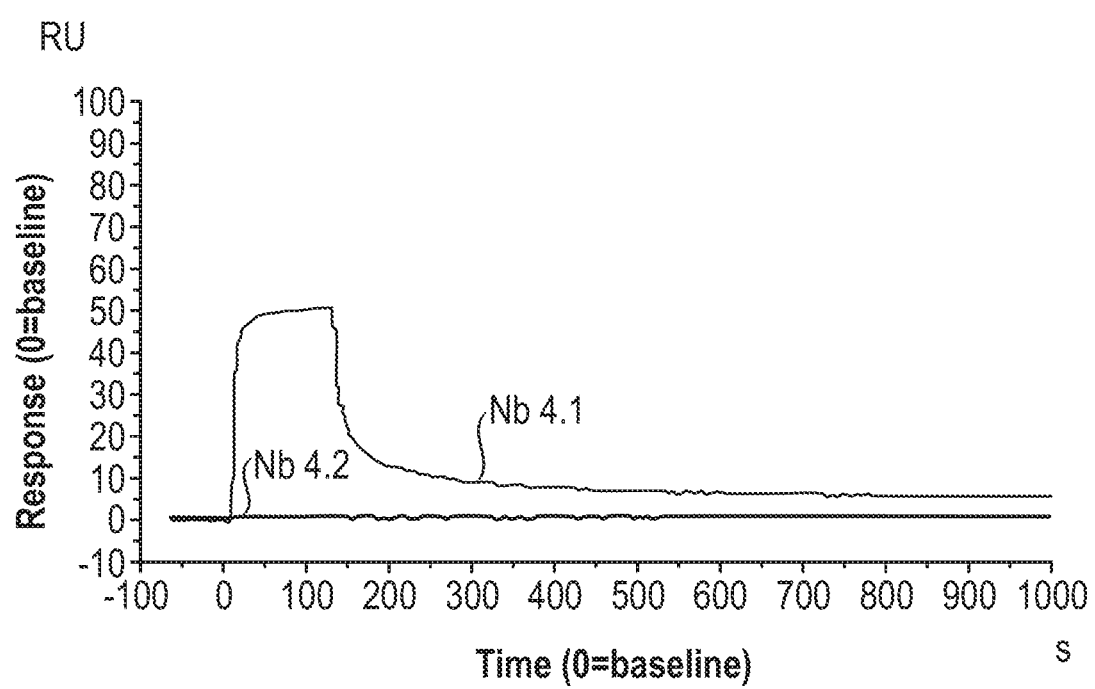
FIG. 7 is a binding curve (obtained using the BIACORE assay described in Example 3) showing the binding of NB's 4.1 and 4.2 (SEQ ID NO's: 17 and 18) to the immobilized polyclonal antibody obtained in Example 2.
Figure 8:
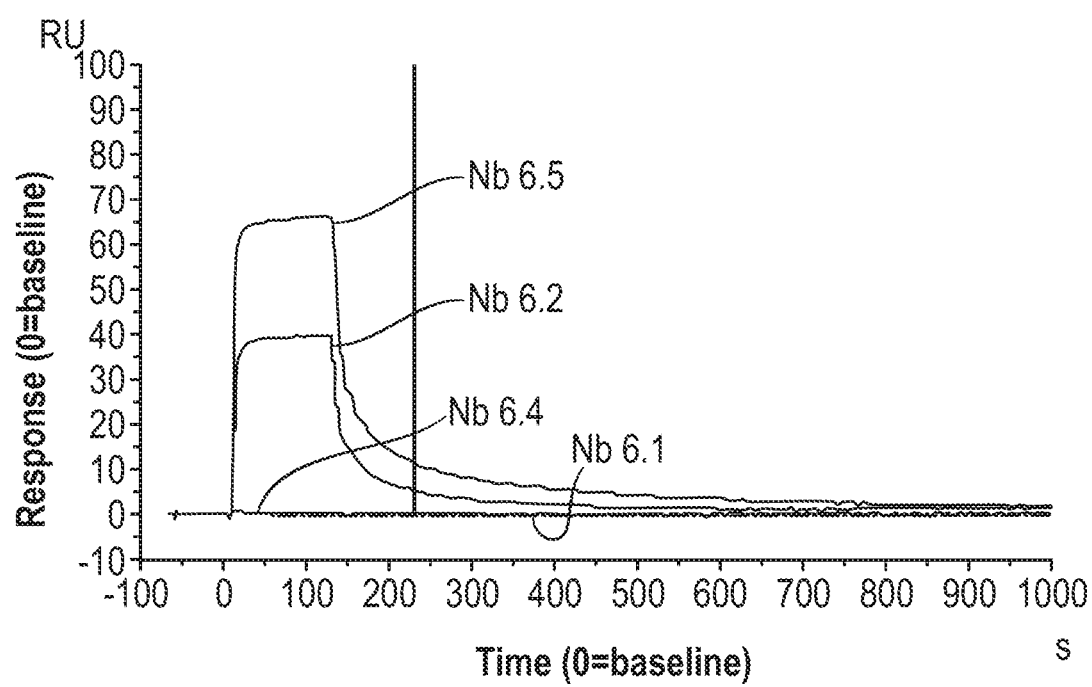
FIG. 8 is a binding curve (obtained using the BIACORE assay described in Example 3) showing the binding of NB's 6.1, 6.2, 6.4 and 6.5 (SEQ ID NO's 19 to 22) to the immobilized polyclonal antibody obtained in Example 2.

As representative examples of the kind of data obtained:

FIG. 4 shows the binding of NB's 3.4, 3.11, 3.12 and 3.13 to the immobilized polyclonal antibody;

FIG. 5 shows the binding of NB's 3.4, 3.14 and 3.15 to the immobilized polyclonal antibody;

FIG. 6 shows the binding of NB's 3.1, 3.2 and 3.4 to the immobilized polyclonal antibody;

FIG. 7 shows the binding of NB's 4.1 and 4.2 to the immobilized polyclonal antibody;

FIG. 8 shows the binding of NB's 6.1, 6.2, 6.4 and 6.5 to the immobilized polyclonal antibody.

Tables VI, VII and VIII summarize the results obtained.

TABLE VI

| Clone ID | SEQ ID NO | Position 14[1] | Position 83[1] | Position 108[1] | Binding** (RU) |
|---|---|---|---|---|---|
| NB 3.4 | 5 | P | R | L | 75 |
| NB 3.10 | 11 | A | R | L | 91 |
| NB 3.11 | 12 | P | K | L | 88 |
| NB 3.12 | 13 | A | R | Q | 86 |
| NB 3.13 | 14 | P | R | Q | 90 |

**Binding signal obtained at the end of injection (=maximal RU signal)
[1]numbering according to Kabat.

TABLE VII

| Clone ID | SEQ ID NO | Position 11[1] | Position 110[1] | Binding** (RU) |
|---|---|---|---|---|
| NB 3.4 | 5 | L | T | 75 |
| NB 3.14 | 15 | L | Q | 79 |
| NB 3.15 | 16 | S | T | 22 |

**Binding signal obtained at the end of injection (=maximal RU signal)
[1]numbering according to Kabat.

TABLE VIII

| Clone ID | SEQ ID NO: | Position 14 | Position 83[1] | Position 108 [2] | Tag* | Binding** (RU) |
|---|---|---|---|---|---|---|
| NB 3.1 | 3 | A | K | Q | − | 2 |
| NB 3.2 | 4 | A | K | Q | + | 0 |
| NB 3.4 | 5 | P | R | L | − | 59 |

| Clone ID | | Position 14 | Position 83 [3] | Position 108 [4] | Tag* | Binding** (RU) |
|---|---|---|---|---|---|---|
| NB 4.1 | 17 | P | R | L | − | 51 |
| NB 4.2 | 18 | P | R | L | + | 0 |

| Clone ID | | Position 14 | Position 83 [5] | Position 108 [6] | Tag* | Binding** (RU) |
|---|---|---|---|---|---|---|
| NB 6.1 | 19 | P | K | Q | + | 0 |
| NB 6.2 | 20 | P | K | Q | − | 39 |
| NB 6.4 | 21 | P | R | L | + | 0 |
| NB 6.5 | 22 | P | R | L | − | 66 |

*if "+", this ISV contains additional amino acids at the C-terminal VTVSS end
**Binding signal obtained at the end of injection (=maximal RU signal)
[1]numbering acc. to Kabat (corresponds to the a.a. at position 87 in SEQ ID NO's 3 to 5).
[2]numbering acc. to Kabat (corresponds to the a.a. at position 123 in SEQ ID NO's 3 to 5).
[3]numbering acc. to Kabat (corresponds to the a.a. at position 86 in SEQ ID NO's 17 and 18).
[4]numbering acc. to Kabat (corresponds to the a.a. at position 116 in SEQ ID NO's 17 and 18).
[5]numbering acc. to Kabat (corresponds to the a.a. at position 86 in SEQ ID NO's 19 to 22).
[6]numbering acc. to Kabat (corresponds to the a.a. at position 112 in SEQ ID NO's 19 to 22).

Again, without being limited to any specific hypothesis or explanation, the data presented above shows that (various) substitutions to the C-terminal region (as defined herein) of an NV can alter/improve its tendency to give rise to protein interference.

Example 4: Representative Protocols for Performing the ADA Assays of FIG. 1

This Example gives some representative but non-limiting conditions that could be used for performing the competitive/bridging ADA assays schematically shown in FIG. 1:

ADA assay of FIG. 1A in solution: Samples 100% matrix, 30', 37° C., Acid treatment using acetic acid in 10 matrix, 5', RT, Preincubation/acid neutralisation sample: ISV-Sulfo (:Tris) 1:1:1 (1:0,9:0,9:0,1), 1h, RT; On plate 1 h, RT; Wash 3×, Readbuffer 4×

Figure 1B:
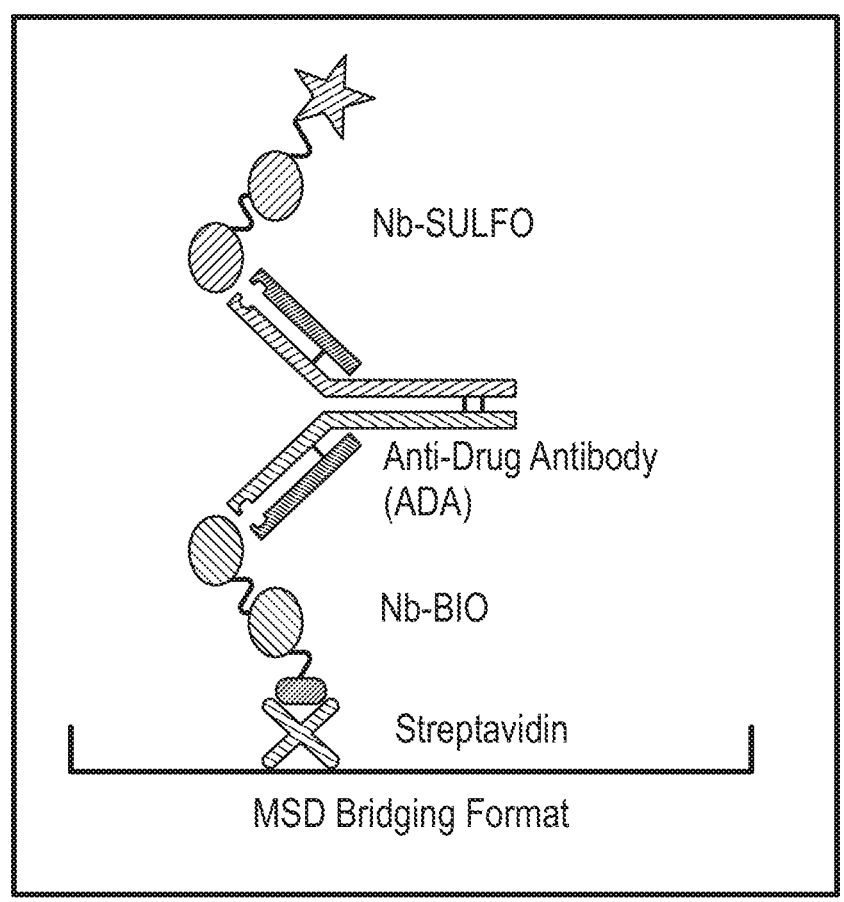

ADA assay of FIG. 1B in solution: Samples 20% matrix, 30', 37° C., Preincubation sample: ISV—Sulfo 1:1:1, 1h, RT, On plate 1 h, RT, Wash 3×, Readbuffer 2×

Figure 1C:
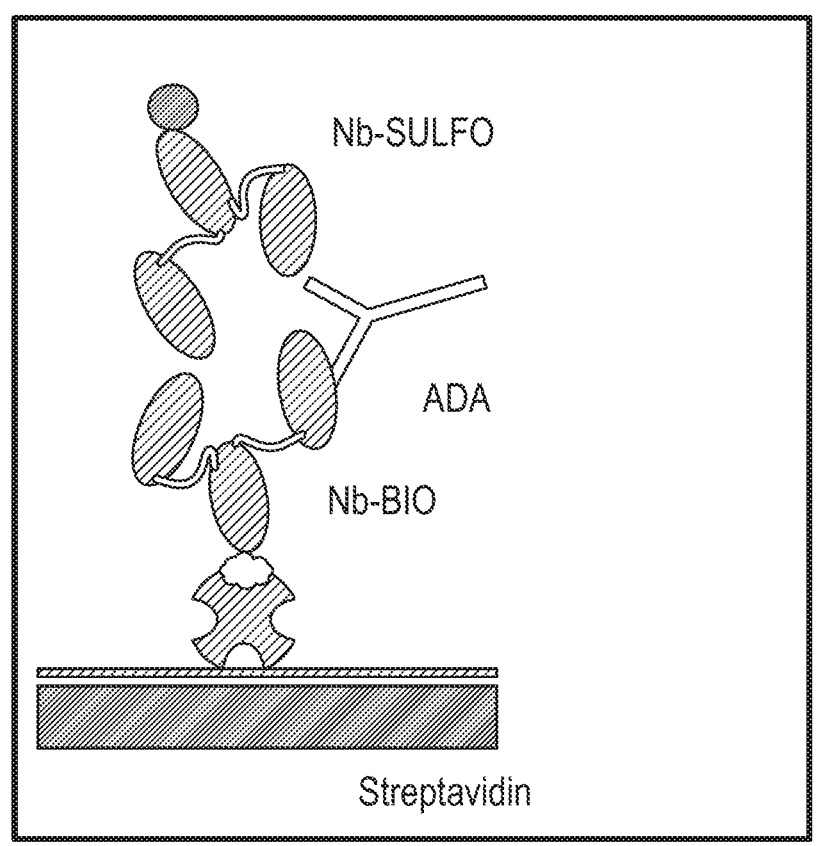

Sequential ADA assay of FIG. 1C: Capture ISV-Bio, 1 h, RT, Wash 3×, Samples 20% matrix, 15', RT, On plate: 2h, RT, Wash 3×, Detection ALX-0141-Sulfo, 1h. RT, Wash 3×, Readbuffer 4×

Example 5: Predicting Sensitivity of the ISV to Aspecific Protein Interference Using the Analytical Antibody This example describes a bridging/competition ADA assay using the analytical antibody that can be used to predict sensitivity of an ISV to aspecific protein interference.

The ISV to be tested is diluted at a concentration of 10 μg/ml and incubated with the analytical antibody at 400 ng/ml, purified according to Example 2, and incubated at 37° C. at 600 rpm in 96 well polypropylene plates. The sample (50 μL) is then diluted 1/3 in 1:1 mixture (100 μL) of 2 μg/ml biotinylated and 2 μg/ml sulfo-tagged ISV and incubated for 1 hour at RT, 600 RPM. MSD MA®96-well Standard Streptavidin plates are blocked with 150 μL/well Superblock® T20 for 1 hour at RT, then washed 3 times with PBS/0.05% Tween20 (=wash buffer). Sample/1:1 mix (biotinylated and sulfo-tagged ISV) (50.0 μL) is transferred from the polypropylene plate to the MSD plate and incubated for 1 hour at RT, 600 rpm. Plates are washed three times prior to addition of 2× Read Buffer (MSD) (150 μL/well) and reading the ECL units (ECLU) on an MSD instrument (Sector Imager 2400 reader).

Using this assay, the ISVs of SEQ ID NO's 23 to 30 were tested and compared. The data are shown in Table IX. These data not only show that the assay described in this Example can be used to predict the tendency of an ISV to give rise to protein interference, but the data generated also confirm the findings from the earlier Examples on the effect of substitutions in the C-terminal region. As can be seen, addition of 3 (and to lesser extent 1) Alanine residues at the C-terminus of the fully humanized ISV abolished its capacity to compete with binding of the analytical antibody. Mutating position 14 on the wild type IS V variant from Alanine to Proline clearly increased its capacity as competitor in the assay, (=making the ISV variant more prone to aspecific protein interference), whereas mutating position 83 and 108 did not clearly influenced the sensitivity of the ISV to aspecific protein interference.

TABLE IX

| | | ID affinity purified antibody IHuP#002-001-ABL-08 ECLU in screening assay (using SEQ ID NO: 1) 2919 | |
|---|---|---|---|
| Nanobody Variant (right hand column mentions the humanizing substitutions and C-terminal additions made compared to the wildtype sequence of SEQ ID NO: 23) | | ECLU confirm-atory assay | % reduc-tion |
| SEQ ID NO: 23 | Wildtype VHH | 2706 | 7.3 |
| SEQ ID NO: 24 | Wildtype VHH + A14P | 268 | 90.8 |
| SEQ ID NO: 25 | Wildtype VHH + K83R | 2460 | 15.71 |
| SEQ ID NO: 26 | Wildtype VHH + Q108L | 2533 | 13.23 |
| SEQ ID NO: 27 | Wildtype VHH + A14P + K83R + Q108L | 319 | 89.1 |
| SEQ ID NO: 28 | Wildtype VHH + A14P + R39Q + K83R + T91Y + Q108L | 251 | 91.4 |
| SEQ ID NO: 29 | Wildtype VHH + A14P + R39Q + K83R + T91Y + Q108L + 1 additional A at C-terminus (A114) | 1207 | 58.64 |
| SEQ ID NO: 30 | Wildtype VHH + A14P + R39Q + K83R + T91Y + Q108L + 3 A's at C-terminus (A114 + A115 + A116) | 3301 | −13.09 |

Example 6: Influence of the Addition of Amino Acids to the C-Terminus of Anti-OX40L Nanobodies on their OX40L Blocking Potency This example demonstrates that the C-terminal extension has no influence on activity or blocking potency of the Nanobodies.

The in vitro potency of the trivalent bispecific sequence optimized anti-OX40L Nanobody Nb 3.16 (SEQ ID NO: 31) was compared with the potency of the corresponding Nanobody containing one additional Ala at its C-terminus Nb 3.17 (SEQ ID NO: 32).

A first assay, the T-cell activation assay, was performed as follows. PBMCs were isolated from buffy coats (Red Cross, Ghent. Belgium) from healthy donors using Ficoll Paque Plus reagent (GE Healthcare) and washed using RPMI 1640 complete medium (RPMI1640+GlutaMAX+25 mM HEPES+10% fetal bovine serum+1 Penicillin/Streptomycin; Invitrogen). The PBMC's ($1\times10^5$ cells/well) were stimulated with phytohaemagglutinin (PHA-L; final concentration 0.6 μg/ml) before the addition to $1\times10^4$ hOX40L expressing CHO cells (irradiated with gamma scintillator at 3000 RAD; UZ Gent, Belgium) and dilution series of anti-OX40L Nanobodies RPMI 1640 complete medium and incubated for 22 hours at 37° C. in CO, incubator. Production of IL2 by the PBMCs was measured in ELISA. Wells of a Maxisorp plate were coaled overnight at 4° C. with anti-human IL2 monoclonal antibody (BD Biosciences). After washing and blocking of the coated wells, a 1/2 dilution of cell supernatant was added. As a standard, 1/2 serial dilutions of recombinant human IL2 (BD Biosciences) starting from 2000 pg/ml were included. Detection was done using biotinylated anti-human IL2 monoclonal antibody (BD Biosciences) and HRP conjugated streptavidin (Thermo Scientific) and esTMB (SDT Reagents). The reaction was stopped with 1N HCl and the OD was read at 450 nm. As expected, the potency of the trivalent bispecific sequence optimized Nanobody Nb 3.17 (IC50=0.13 nM, 95% CI=0.098-0.17 nM) was comparable to that of Nb 3.16 (IC50=0.10 nM, 95% CI=0.071-0.15 nM).

In a second ELISA-based competition assay, a dilution series (from 1.5 μM to 0.083 pM) of the Nanobodies were pre-incubated overnight at room temperature with 100 ng/ml human OX40/Fc (R&D Systems) and 10 ng/mlbiotinylated human OX40L (R&D Systems; in-house biotinylated as described in Example 1) in PBS+0.1% BSA+0.01% Tween-20. Next, the samples were incubated on Maxisorp plates coated with 10 ug/ml anti-human Fc Nanobody (in-house generated) and blocked with PBS+1% BSA+0.1% Tween-20. Bound human OX40/Fc was detected using HRP conjugated streptavidin (Thermo Scientific) and sTMB (SDT Reagents). The reaction was stopped with 1N HCl and the OD was read at 450 nm. In accordance with the cell-based assay, the potency of the trivalent bispecific sequence optimized Nanobodies Nb 3.17 (IC50=0.178 nM, 95% CI=0.152-0.200 nM) was comparable to that of Nb 3.16 (IC50=0.179 nM, 95% CI=0.149-0.215 nM).

Example 7: Generation of Monoclonal Antibody 21-4-3

Two groups of different mice strains (BALB/c and NMRI—three mice each) were intraperitoneally immunized with the Nanobody construct of SEQ ID NO:98 in WO 2006/122825, in a water-in-oil emulsion of equal volumes of antigen and Freund's complete or incomplete adjuvant) over a period of 39 days, with boosting until suitable antiserum titers were obtained.

After asphyxiation of the stimulated mice in CO2, the spleens were aseptically removed and a single cell suspension of pooled spleens was prepared. Spleen cells and myeloma cells were washed several times with DMEM and fused in the presence of 1 ml 50% (w/v) PEG 3350 (ratio spleen cells to SP2/0 3:1). For fusion was used the myeloma cell line SP2/0-Ag14 from German Collection of Microorganisms and Cell Cultures (DSMZ GmbH, Braunschweig). This cell line is a hybrid between BALB/c spleen cells and the myeloma cell line P3×63Ag8. The so produced hybridomas were resuspended in CGM containing 20% FCS and aminopterin (HAT medium) and plated out (140 μl/well) into eight 96-well tissue culture flat-bottom plates (Corning-Costar) containing 140 μl/well CGM (20% FCS) with peritoneal excudate cells as feeder cells. The plates were incubated for 10 days in a complete growth medium (CGM) containing DMEM with supplements 2-mercaptoethanol, L-Glutamin, Stable Glutamin, HT and non essential amino acids (in concentrations recommended by the supplier) and FCS at different concentrations (10%, 15% or 20%). During this period cells were fed two times with HAT medium. The cell culture supernatants from hybridoma cells usually contained 1 to 20 μg/ml antibody, which were tested in a binding ELISA to confirm binding to the Nanobody construct of SEQ ID NO:98 in WO 2006/122825.

Cells from positive IgG producing wells were transferred into wells of 48 well plates and cultivated for 2-4 days (depending on growth characteristic of cells). Binding ELISA's on ALX081 and human/cynomolgus IgG were carried out in order to exclude the unspecific binders. Hybridoma cells expressing binders specific for the Nanobody construct of SEQ ID NO:98 in WO 2006/122825 were twice cloned using limited dilution. After fusion and rescreening 7 primary cultures producing antibodies against ALX-081 were identified. All these primary cultures produced antibodies not cross-reacting with human or cynomolgus IgG. The primary cultures were recloned (twice).

Clone 21-4 (one of the clones that stably produced antibodies against ALX-081 after the second cloning) was given the designation "ABH0015" and was deposited with the Belgian Coordinated Collections of Micro-organisms (BCCM) in Ghent, Belgium on Jun. 4, 2012 under accession number LMBP-9680-CB. The mouse monoclonal produced by ABH0015 was called 21-4-3: isotype determination for 21-4-3 showed an IgG1 heavy chain and a kappa light chain, which were sequenced (see SEQ ID NO's: 35 and 36, respectively). 21-4-3 was shown to bind to the C-terminal region of the Nanobody construct of SEQ ID NO:98 in WO 2006/122825 (data not shown).

Example 8: Binding of 21-4 to an ISV is Predictive of the Tendency of an ISV to Undergo Aspecific Protein Interference This Example together with the following Example 9 demonstrates that binding of the monoclonal 21-4 to an ISV can be used to predict (within the degrees of certainty indicated in this Example) of whether a given ISV will have a tendency to undergo aspecific protein interference (e.g. in an ADA assay).

This Example 8 in particular shows that 21-4 can be used to predict whether certain proposed modifications to a given ISV (such as adding one or more amino acid residues to the C-terminus of an ISV and/or substituting one or more amino acid substitutions within the C-terminal region of an ISV) will lead to a reduction of the tendency of said ISV to undergo aspecific protein interference.

In short, a set of 53 different Nanobodies and Nanobody constructs (see FIG. 9 and SEQ ID NO's: 38 to 89) were tested for binding by monoclonal 21-4-3. The same Nanobodies and Nanobody constructs were also tested for binding by purified preparations of interference factor(s) obtained from three different human donors (referred to herein as "Donor 8", "Donor 19" and "Donor 30"), to see if there was any correlation between binding by 21-4 and by the purified interference factors.

It was established that binding of an ISV by 21-4 can indeed be used to predict binding of the same ISV's by the interference factor(s) (within the overall degree of confidence provided by the data set out herein).

To demonstrate this, as detailed by the experimental data set out below, the binding of the 53 Nanobodies or Nanobody constructs (as listed in FIG. 9; see SEQ ID NO's: 38 to 89) by 21-4 was measured using a Biacore T100 (according to the protocol set out below) and was compared to binding of a reference Nanobody or construct (also listed in FIG. 9), as measured using the same Biacore instrument and the same protocol. The results are shown in Table X below.

TABLE X

| SEQ ID NO: | C-terminal amino acid(s) | mutations to the C-terminal region | reduction in binding of 21-4-3 vs binding of Reference Sequence (= 100%) | reduction of interference in serum from Donor A compared to Reference Sequence (= 100%) | reduction of interference in serum from Donor B compared to Reference Sequence (= 100%) | reduction of interference in serum from Donor C compared to Reference Sequence (= 100%) | More than 70% reduction in binding of Nanobody to 21-4-3 predicts >50% reduction in binding of nanobody to interference | More than 90% reduction in binding of Nanobody to 21-4-3 predicts >50% reduction in binding of nanobody to interference |
|---|---|---|---|---|---|---|---|---|
| 37 | A | none | 7% | 3% | 21% | 31% | ok | ok |
| 38 | A | none | 0% | 9% | 25% | 7% | ok | ok |
| 39 | A | none | 0% | 10% | 43% | 35% | ok | ok |
| 40 | A | none | 1% | 6% | #N/A | #N/A | ok | ok |
| 41 | A | none | 7% | 6% | 9% | #N/A | ok | ok |
| 42 | A | none | 0% | 1% | 4% | #N/A | ok | ok |
| 43 | A | none | 3% | 3% | 20% | #N/A | ok | ok |
| 44 | A | none | 1% | 5% | #N/A | #N/A | ok | ok |
| 45 | none | P14A, P41T, S62F, S74A, S82bN, R83K, L108Q | 22% | 0% | #N/A | #N/A | ok | |
| 46 | AAEQKLI SEEDLN | A14P, T41P, F62S, A74S, | 2% | 0% | #N/A | #N/A | ok | ok |

TABLE X-continued

| SEQ ID NO: | C-terminal amino acid(s) | mutations to the C-terminal region | reduction in binding of 21-4-3 vs binding of Reference Sequence (= 100%) | reduction of interference in serum from Donor A compared to Reference Sequence (= 100%) | reduction of interference in serum from Donor B compared to Reference Sequence (= 100%) | reduction of interference in serum from Donor C compared to Reference Sequence (= 100%) | More than 70% reduction in binding of Nanobody to 21-4-3 predicts >50% reduction in binding of nanobody to interference | More than 90% reduction in binding of Nanobody to 21-4-3 predicts >50% reduction in binding of nanobody to interference |
|---|---|---|---|---|---|---|---|---|
| | GAAHHHHHH | N82bS, K83R, Q108L | | | | | | |
| 47 | GGGGSGGGSRDWDFDVFGGGTPVGG | none | 4% | 1% | #N/A | #N/A | ok | ok |
| 48 | AAEQKLISEEDLNGAAHHHHHH | none | 3% | 0% | #N/A | #N/A | ok | ok |
| 49 | AAEQKLISEEDLNGAAHHHHHH | V5L, I23A, E44G, A49S, A68T, A74S, T78L, W79Y, K83R, T110Q, Q108L | 4% | 0% | #N/A | #N/A | OK | OK |
| 50 | none | L11S | 44% | 77% | 33% | #N/A | (<70% reduction) | (<90% reduction) |
| 51 | none | T110Q | 88% | 85% | 84% | #N/A | (<70% reduction) | (<90% reduction) |
| 52 | none | S112G | 100% | 84% | 58% | #N/A | (<70% reduction) | (<90% reduction) |
| 53 | none | S113G | 13% | 85% | 88% | #N/A | NOK | (<90% reduction) |
| 54 | none | L11S, T110Q, S112G, S113G | 16% | 39% | 16% | #N/A | OK | OK |
| 55 | A | none | 6% | 2% | 21% | 31% | OK | OK |
| 56 | G | S113G | 3% | 2% | 25% | 0% | OK | OK |
| 57 | AS | none | 6% | 1% | 2% | #N/A | OK | OK |
| 58 | AST | none | 6% | 2% | 2% | #N/A | OK | OK |
| 59 | ASTK | none | 6% | 2% | 1% | #N/A | OK | OK |
| 60 | ASP | none | 6% | 2% | 1% | #N/A | OK | OK |
| 61 | AP | none | 6% | 2% | 2% | #N/A | OK | OK |
| 62 | APT | none | 6% | 2% | 1% | #N/A | OK | OK |
| 63 | W | none | 3% | 4% | 8% | #N/A | OK | OK |
| 64 | L | none | 6% | 3% | 4% | #N/A | OK | OK |
| 65 | none | P14A | 23% | 73% | 121% | 64% | NOK | (<90% reduction) |
| 66 | none | L11S | 48% | 81% | 29% | 84% | (<70% reduction) | (<90% reduction) |
| 67 | none | R83K | 101% | 102% | 117% | 96% | (<70% reduction) | (<90% reduction) |

TABLE X-continued

| SEQ ID NO: | C-terminal amino acid(s) | mutations to the C-terminal region | reduction in binding of 21-4-3 vs binding of Reference Sequence (= 100%) | reduction of interference in serum from Donor A compared to Reference Sequence (= 100%) | reduction of interference in serum from Donor B compared to Reference Sequence (= 100%) | reduction of interference in serum from Donor C compared to Reference Sequence ( For each of the 53 Nanobodies or Nanobody constructs tested, the reference was chosen such that compared to the reference, the tested Nanobodies or Nanobody constructs either had one or more additional amino acid residues at the C-terminal end (which were added in order to test the effect of such addition on protein interference, and in particular in order to reduce said interference) and/or one or more mutations within the C-terminal region (for example, as a result of humanization compared to the reference).

The results were expressed as a percentage reduction in binding (measured as RU units) for the given Nanobody versus the binding of the reference (also measured in RU units—for example, if the measured binding level (RU) of the reference Nanobody was 276 and the binding level of the given Nanobody (also in RU) was 9, then the reduction in binding level was to a level of [9 RU/276 RU]×100%=3%), which means a reduction of 97% compared to the reference (100%).

Similarly, binding of the purified interference factor(s) from each of the three donors to each of the 53 Nanobodies or Nanobody constructs was measured using the same Biacore instrument and compared to binding of the purified interference factor(s) to the same reference Nanobody or construct. The results were similarly expressed as a percentage reduction in binding of the interference factor to the given Nanobody or Nanobody construct vs the reference.

It was found that for essentially all Nanobody or Nanobody construct in which one or more amino acid residues had been added to the C-terminal end compared to the reference, that the binding of the interference factor(s) was dramatically reduced. This again confirms that adding one or more amino acid residues to the C-terminal end of an ISV (VTVSS) can reduce aspecific protein interference in an ADA assay. It was also found that in the majority of cases, only making substitutions within the C-terminal region (i.e. without adding one or more amino acid residues to the C-terminus) compared to the reference often did not have a similar dramatic impact on the binding of the interference factor(s).

The data was then further analysed to determine whether a reduction in binding by 21-4 compared to the reference was in any way correlated with a reduction in binding by each of the three different preparations of purified interference factor compared to the reference. Such correlations were found.

For example, it was found that of the 54 Nanobodies or Nanobody constructs tested, 36 showed a reduction in binding by 21-4 of more than 70% compared to their respective reference sequence (with most of these 36 having one or more additional amino acid residues at the C-terminus, in some cases in combination with substitutions within the C-terminal region). Of these 36, 32 also showed reduction in binding by the interference factor(s) compared to the reference of more than 50% (and in a large number of cases, in particular for Nanobodies or Nanobody constructs with one or more amino acid residues added at the C-terminus, the reduction was far greater than 50%, such as more than 70% or even more than 90%, see the data given in the Table X). This demonstrates that in 32 out of 36 cases (i.e. 89%), a reduction in binding by 21-4 of more than 70% (compared to the reference=100%) is predictive for a reduction in binding by the interference factors of more than 50% (compared to the same reference). For clarity, in each case, the reduction was calculated as 100%-[the percentage given in the Tables below for the level of reduction achieved with the Nanobody tested].

Similarly, it was found that of the 53 Nanobodies or Nanobody constructs tested, 33 showed a reduction in binding by 21-4 of more than 90% compared to their respective reference sequence (again, with most of these 33 having one or more additional amino acid residues at the C-terminus, in some cases in combination with substitutions within the C-terminal region). Of these 33, 32 also showed reduction in binding by the interference factor(s) compared to their respective reference sequence of more than 50%. This demonstrates that in 32 out of 33 cases (i.e. 97%), a reduction in binding by 21-4 of more than 90% (compared to the reference) is predictive for a reduction in binding by the interference factors of more than 50% (compared to the same reference).

It should also be noted that such a reduction in binding of the interference factor(s) by more than 50% (as evidenced by a reduction of binding by 21-4 of more than 70%) means that such interference factor(s) essentially no longer interfere(s) with an ADA assay for the ISV in question: experimental confirmation using an ADA assay showed that when the binding by the interference factor(s) is reduced by more than 45%, that no significant influence of the presence of the interference factor(s) on the ADA assay could be observed. In this respect, it will be also clear to the skilled person that this will even more so be the case when the binding by interference factor(s) is reduced to an extent far greater than 50% (such as by more than 70% or even more than 90%), as is observed in some cases (see again the data presented herein).

In fact, it has been found that a reduction of more than 45% of binding by 21-4 is indicative of a reduction of binding by interference factors of more than 45%, which as mentioned means that the interference factor(s) no longer interfere with the ADA assay.

Moreover, the data presented herein on the correlation between (reduction in) binding by 21-4 and (reduction in) binding by interference factor also allowed the present inventors to set an absolute value for the binding by 21-4 below which it can be expected (within the confidence provided by the data set out in this Example 8) that an ISV or ISV-based construct will not be susceptible to binding by interference factor(s) in a way that could interfere with an ADA assay. As set out in the following Example 9, this value is 500 RU (determined and calculated as set out in Example 9).

Monoclonal 21-4 was purified from the culture medium of the hybridoma obtained in Example 7 above, as follows: Hybridoma cells secreting the monoclonal antibody 21-4-3 were cultured in spinner flasks in serum free medium (CD Hybridoma, Gibco, supplemented with 8 mM L-glutamine (Invitrogen) and 1× cholesterol (250× cholersterol lipid concentrate, Gibco)) at a volume of 100 mL or 500 mL. The cleared supernatant was filtered, and the murine IgG1 captured on a ProteinA column (HiTrap MabSelect SuRe, 5 mL, GE Healthcare) at a reduced flow rate of 2 mL/min. Bound antibody was eluted in 0.1M citrate buffer pH3.0, and elution fractions (of 5 mL) directly neutralized with 1 mL of 1M TRIS pH9. Purity of the antibody was verified by reducing and non-reducing SDS-PAGE.

The purified preparations of interference factor(s) from Donors 8 and 19 were obtained from serum samples from said donors by means of affinity purification, essentially as described in Example 2A. The interference factor(s) from Donor 30 were obtained from a serum sample of Donor 30, essentially as described in Example 2B.

To determine the binding of 21-4 to each of the Nanobodies or Nanobody constructs, the protocol described in Example 9 was used.

The binding of the interference factors from the three donors to each of the Nanobodies or Nanobody constructs was determined using a Biacore T100 essentially as described in Example 3, using the interference factor from each of the donors 8, 19 and 30, directly immobilized on a CM5 sensor chip.

Example 9: Protocol for Predicting Whether an ISV Will have a Tendency to Undergo Aspecific Protein Interference (Using Monoclonal 21-4)

Binding measurements were performed using a Biacore T100 using a CM5 T120416 sensor chip, with running buffer HBS-EP+, 25° C. 21-4 was captured via immobilized rabbit anti-mouse IgG, as it was found that directly immobilized mAb 21-4-3 surface could not efficiently be regenerated. The anti-mouse IgG used was a polyclonal rabbit anti-mouse IgG antibodies reacting with all IgG subclasses, IgA and IgM (GE Healthcare; Cat #BR-1008-38; Lot #10056316). Immobilisation of the anti-mouse IgG was performed using manual amine coupling using a 7 minute injection of EDC/NHS for activation and a 7 minute injection of 1M ethanolamine HCl pH 8.5 for deactivation (Biacore, amine coupling kit). Binding conditions are listed in Table XI. Based on the immobilization level and MW of the proteins, the theoretical $R_{max}$ for mAb21-4-3 binding to the immobilized anti-mouse IgG was ~13000RU (when one mAb21-4-3 molecule is binding to one anti-mouse IgG molecule).

TABLE XI

| Protein | Conc. (µg/ml) | Contact time (s) | Flow rate (µl/min) | Immobilization buffer | Immobilization level (RU) |
|---|---|---|---|---|---|
| Anti-mouse IgG | 30 | 420 | 5 | 10 mM acetate pH 5.0 | 13028 |
| Anti-mouse IgG | 30 | 420 24 | 5 | 10 mM acetate pH 5.0 | 13318 |

The conditions used for the binding experiment (Biacore T100) using 21-4 immobilized in the manner are given in Table XII. The anti-mouse IgG surface could successfully be regenerated after capture of mAb21-4-3 and injection of all samples (with a limited increase for baseline level after each regeneration).

TABLE XII

| Capture | |
|---|---|
| Flow path | 4 |
| Flow rate (µl/min) | 10 |
| Contact time (s) | 180 |
| Concentration (µg/ml) | 10 |

TABLE XII-continued

| Binding and dissociation | |
|---|---|
| Flow path | 3, 4 |
| Flow rate (µl/min) | 45 |
| Sample contact time (s) | 120 |
| Sample concentration (nM) | 500 |
| Dissociation time (s) | 600 |
| Regeneration1 | |
| Flow path | 3, 4 |
| Flow rate (µl/min) | 10 |
| Regeneration contact time (s) | 180 |
| Regeneration buffer | 10 mM Glycine-HCl pH 1.7 |
| Stabilization time (s) | 120 |
| If . . . Then . . . Else | If after regeneration1 >20 RU on Fc4 Else exit cycle |
| Regeneration2 | |
| Flow path | 3, 4 |
| Flow rate (µl/min) | 10 |
| Regeneration contact time (s) | 120 |
| Regeneration buffer | 10 mM Glycine-HCl pH 1.7 |
| Stabilization time (s) | 120 |

The above protocol was used to generate the 21-4 binding data set out in Table X. When the absolute values for RU were considered (after adjusting the measured RU value for the molecular weight of the ISV, protein or polypeptide according to the formula ([RU measured]/[MW of the protein]×$10^6$), it was found that the Nanobodies and Nanobody constructs mentioned in Table X that had an added alanine residue and that showed >90% reduction in binding to both 21-4 as well as interference factors, generally provided RU values of between 30RU and 400RU (with the corresponding reference Nanobodies or polypeptides—as listed in FIG. 9—having RU values of more than 1000, usually more than 1500, and often more than 2000).

Based on this, it was considered that an (adjusted) RU value of less than 500 in this assay would be clearly indicative of an ISV(or a protein or polypeptide that comprises as least one IS, as described herein) that will (essentially) not be bound by interference factors in a manner that would interfere with an ADA assay.

The entire contents of all of the references (including literature references, issued patents, published patent applications, and co-pending patent applications) cited throughout this application are hereby expressly incorporated by reference, in particular for the teaching that is referenced herein.

The invention claimed is:

1. A protein or polypeptide comprising an immunoglobulin single variable domain (ISV) at its C-terminal end, wherein said ISV is a VHH, humanized VHH or camelized VH, which ISV has a C-terminal end of the sequence VTVSS(X)$_n$ (SEQ ID NO: 34), in which each X is an amino acid residue that is independently chosen and wherein:
   n=1 or 2 in which each X=Ala or Gly; or
   n=1 or 2 in which each X=Ala; or
   n=1, 2 or 3 in which each X=Gly; or
   n=2 or 3 in which at least one X=Ala or Gly, wherein when n=3, at least one X is not Ala; or
   n=2 or 3 in which all but one X=Ala or Gly,
   and which protein or polypeptide includes a serum albumin binding peptide or serum albumin binding domain linked to the ISV directly or via one or more linkers.

2. The protein or polypeptide according to claim 1, in which the protein or polypeptide comprises a serum albumin binding domain that is a serum albumin binding ISV, wherein said serum albumin binding ISV is a VHH, humanized VHH or camelized VH.

3. The protein or polypeptide according to claim 2, in which said serum albumin binding ISV is a VHH or a humanized VHH that is Alb-1 or a humanized version of Alb-1.

4. The protein or polypeptide according to claim 3, in which said humanized version of Alb-1 is Alb-8.

5. The protein or polypeptide according to claim 1, in which n=1 or n=2.

6. The protein or polypeptide according to claim 1, in which:
   n=2 or 3 and at least one X=Ala or Gly, wherein when n=3, at least X is not Ala; or
   n=2 or 3 and all but one X=Ala or Gly.

7. The protein or polypeptide according to claim 6, in which the remaining amino acid residue X is independently chosen from Val, Leu and/or Ile.

8. The protein or polypeptide according to claim 1, in which:
   n=1 or 2 in which each X=Ala or Gly; or
   n=1 or 2 in which each X=Ala; or
   n=1, 2 or 3 in which each X=Gly.

9. The protein or polypeptide according to claim 1, in which X is not cysteine.

10. A pharmaceutical composition comprising a protein or polypeptide according to claim 1, and at least one suitable carrier, diluent or excipient.

11. A protein or polypeptide comprising an immunoglobulin single variable domain (ISV) at its C-terminal end, wherein said ISV is a VHH, humanized VHH or camelized VH, which ISV has a C-terminal end of the sequence VTVSS(X)$_n$ (SEQ ID NO: 34), in which n is 1, 2, 3, or 5, and in which each X is an amino acid residue that is independently chosen, with the proviso that X is not cysteine, wherein when n=3, at least one amino acid residue X is not alanine, and which protein or polypeptide includes a serum albumin binding peptide or serum albumin binding domain linked to the ISV directly or via one or more linkers.

12. The protein or polypeptide according to claim 11, in which each X is a naturally occurring amino acid.

13. The protein or polypeptide according to claim 11, in which the protein or polypeptide comprises a serum albumin binding domain that is a serum albumin binding ISV, wherein said serum albumin binding ISV is a VHH, humanized VHH or camelized VH.

14. The protein or polypeptide according to claim 13, in which said serum albumin binding ISV is a VHH or a humanized VHH that is Alb-1 or a humanized version of Alb-1.

15. The protein or polypeptide according to claim 14, in which said humanized version of Alb-1 is Alb-8.

16. A pharmaceutical composition comprising a protein or polypeptide according to claim 11, and at least one suitable carrier, diluent or excipient.

17. A protein or polypeptide comprising an immunoglobulin single variable domain (ISV) at its C-terminal end, wherein said ISV is a VHH, humanized VHH or camelized VH, which ISV has a C-terminal end of the sequence VTVSS(X)$_n$ (SEQ ID NO: 34), in which n is 1 to 5, in which each X is independently chosen from the group consisting of alanine (A), glycine (G), valine (V), leucine (L) or isoleucine (I), wherein when n=3, at least one amino acid residue X is not alanine, and which protein or polypeptide includes a serum albumin binding peptide or serum albumin binding domain linked to the ISV directly or via one or more linkers.

18. The protein or polypeptide according to claim 17, in which the protein or polypeptide comprises a serum albumin binding domain that is a serum albumin binding ISV, wherein said serum albumin binding ISV is a VHH, humanized VHH or camelized VH.

19. The protein or polypeptide according to claim 18, in which said serum albumin binding ISV is a VHH or a humanized VHH that is Alb-1 or a humanized version of Alb-1.

20. The protein or polypeptide according to claim 19, in which said humanized version of Alb-1 is Alb-8.

21. A pharmaceutical composition, comprising a protein or polypeptide according to claim 17, and at least one suitable carrier, diluent or excipient.

22. A protein or polypeptide comprising an immunoglobulin single variable domain (ISV) at its C-terminal end that binds a therapeutic target, wherein said ISV is a VHH, humanized VHH or camelized VH, which ISV has a C-terminal end of the sequence VTVSS(X)$_n$ (SEQ ID NO: 34), in which each X is an amino acid residue that is independently chosen and wherein:
   n=1, 2 or 3 in which each X=Ala or Gly; or
   n=1, 2 or 3 in which each X=Ala; or
   n=1, 2 or 3 in which each X=Gly; or
   n=2 or 3 in which at least one X=Ala or Gly; or
   n=2 or 3 in which all but one X=Ala or Gly,
   and which protein or polypeptide includes a serum albumin binding peptide or serum albumin binding domain linked to the ISV directly or via one or more linkers.

23. The protein or polypeptide according to claim 22, in which the remaining amino acid residue X is independently chosen from Val, Leu and/or Ile.

24. The protein or polypeptide according to claim 22, in which X is not cysteine.

25. The protein or polypeptide according to claim 22, in which the protein or polypeptide comprises a serum albumin binding domain that is a serum albumin binding ISV, wherein said serum albumin binding ISV is a VHH, humanized VHH or camelized VH.

26. The protein or polypeptide according to claim 25, in which said serum albumin binding ISV is a VHH or a humanized VHH that is Alb-1 or a humanized version of Alb-1.

27. The protein or polypeptide according to claim 26, in which said humanized version of Alb-1 is Alb-8.

28. A pharmaceutical composition comprising a protein or polypeptide according to claim 22, and at least one suitable carrier, diluent or excipient.

29. A protein or polypeptide comprising an immunoglobulin single variable domain (ISV) at its C-terminal end that binds a therapeutic target, wherein said ISV is a VHH, humanized VHH or camelized VH, which ISV has a C-terminal end of the sequence VTVSS(X)$_n$ (SEQ ID NO: 34), in which n is 1 to 5, and in which each X is an amino acid residue that is independently chosen, with the proviso that X is not cysteine, and which protein or polypeptide includes a serum albumin binding peptide or serum albumin binding domain linked to the ISV directly or via one or more linkers.

30. The protein or polypeptide according to claim 29, in which each X is a naturally occurring amino acid.

31. The protein or polypeptide according to claim 29, in which each X is chosen from the group consisting of alanine (A), glycine (G), valine (V), leucine (L) or isoleucine (I).

32. The protein or polypeptide according to claim 29, in which the protein or polypeptide comprises a serum albumin binding domain that is a serum albumin binding ISV, wherein said serum albumin binding ISV is a VHH, humanized VHH or camelized VH.

33. The protein or polypeptide according to claim 32, in which said serum albumin binding ISV is a VHH or a humanized VHH that is Alb-1 or a humanized version of Alb-1.

34. The protein or polypeptide according to claim 33, in which said humanized version of Alb-1 is Alb-8.

35. A pharmaceutical composition comprising a protein or polypeptide according to claim 29, and at least one suitable carrier, diluent or excipient.

* * * * *

SEQUENCE LISTING

<160> NUMBER OF SEQ ID NOS: 89

<210> SEQ ID NO 1
<211> LENGTH: 270
<212> TYPE: PRT
<213> ORGANISM: Artificial sequence
<220> FEATURE:
<223> OTHER INFORMATION: immunoglobulin single variable domain

<400> SEQUENCE: 1

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

```
Ser Gly Ile Lys Ser Ser Gly Asp Ser Thr Arg Tyr Ala Gly Ser Val
    50              55                  60
Lys Gly Arg Phe Thr Ile Ser Arg Asp Asn Ala Lys Asn Thr Leu Tyr
65              70                  75                  80
Leu Gln Met Asn Ser Leu Arg Pro Glu Asp Thr Ala Val Tyr Tyr Cys
            85                  90                  95
Ala Lys Ser Arg Val Ser Arg Thr Gly Leu Tyr Thr Tyr Asp Asn Arg
            100                 105                 110
Gly Gln Gly Thr Leu Val Thr Val Ser Ser Gly Gly Gly Gly Ser Gly
            115                 120                 125
Gly Gly Ser Gly Gly Gly Ser Gly Gly Gly Ser Glu Val
            130                 135                 140
Gln Leu Val Glu Ser Gly Gly Gly Leu Val Gln Pro Gly Gly Ser Leu
145             150                 155                 160
Arg Leu Ser Cys Ala Ala Ser Gly Arg Thr Phe Asn Asn Tyr Ala Met
            165                 170                 175
Gly Trp Phe Arg Gln Ala Pro Gly Lys Glu Arg Glu Phe Val Ala Ala
            180                 185                 190
Ile Thr Arg Ser Gly Val Arg Ser Gly Val Ser Ala Ile Tyr Gly Asp
            195                 200                 205
Ser Val Lys Asp Arg Phe Thr Ile Ser Arg Asp Asn Ala Lys Asn Thr
            210                 215                 220
Leu Tyr Leu Gln Met Asn Ser Leu Arg Pro Glu Asp Thr Ala Val Tyr
225             230                 235                 240
Tyr Cys Ala Ala Ser Ala Ile Gly Ser Gly Ala Leu Arg Arg Phe Glu
            245                 250                 255
Tyr Asp Tyr Ser Gly Gln Gly Thr Leu Val Thr Val Ser Ser
            260                 265                 270

<210> SEQ ID NO 2
<211> LENGTH: 385
<212> TYPE: PRT
<213> ORGANISM: Artificial sequence
<220> FEATURE:
<223> OTHER INFORMATION: immunoglobulin single variable domain

<400> SEQUENCE: 2

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Pro Met Gly Trp Phe Arg Gln Ala Pro Gly Lys Gly Arg Glu Phe Val
            35                  40                  45
Ser Ser Ile Thr Gly Ser Gly Ser Thr Tyr Tyr Ala Asp Ser Val
    50              55                  60
Lys Gly Arg Phe Thr Ile Ser Arg Asp Asn Ala Lys Asn Thr Leu Tyr
65              70                  75                  80
Leu Gln Met Asn Ser Leu Arg Pro Glu Asp Thr Ala Val Tyr Tyr Cys
            85                  90                  95
Ala Ala Tyr Ile Arg Pro Asp Thr Tyr Leu Ser Arg Asp Tyr Arg Lys
            100                 105                 110
Tyr Asp Tyr Trp Gly Gln Gly Thr Leu Val Thr Val Ser Ser Gly Gly
            115                 120                 125
Gly Gly Ser Gly Gly Gly Ser Glu Val Gln Leu Val Glu Ser Gly Gly
            130                 135                 140
```

```
Gly Leu Val Gln Pro Gly Asn Ser Leu Arg Leu Ser Cys Ala Ala Ser
145                 150                 155                 160

Gly Phe Thr Phe Ser Ser Phe Gly Met Ser Trp Val Arg Gln Ala Pro
                165                 170                 175

Gly Lys Gly Leu Glu Trp Val Ser Ser Ile Ser Gly Ser Gly Ser Asp
            180                 185                 190

Thr Leu Tyr Ala Asp Ser Val Lys Gly Arg Phe Thr Ile Ser Arg Asp
        195                 200                 205

Asn Ala Lys Thr Thr Leu Tyr Leu Gln Met Asn Ser Leu Arg Pro Glu
    210                 215                 220

Asp Thr Ala Val Tyr Tyr Cys Thr Ile Gly Gly Ser Leu Ser Arg Ser
225                 230                 235                 240

Ser Gln Gly Thr Leu Val Thr Val Ser Ser Gly Gly Gly Gly Ser Gly
                245                 250                 255

Gly Gly Ser Glu Val Gln Leu Val Glu Ser Gly Gly Gly Leu Val Gln
            260                 265                 270

Pro Gly Gly Ser Leu Arg Leu Ser Cys Ala Ala Ser Gly Phe Thr Phe
        275                 280                 285

Ser Ser Tyr Pro Met Gly Trp Phe Arg Gln Ala Pro Gly Lys Gly Arg
    290                 295                 300

Glu Phe Val Ser Ser Ile Thr Gly Ser Gly Gly Ser Thr Tyr Tyr Ala
305                 310                 315                 320

Asp Ser Val Lys Gly Arg Phe Thr Ile Ser Arg Asp Asn Ala Lys Asn
                325                 330                 335

Thr Leu Tyr Leu Gln Met Asn Ser Leu Arg Pro Glu Asp Thr Ala Val
            340                 345                 350

Tyr Tyr Cys Ala Ala Tyr Ile Arg Pro Asp Thr Tyr Leu Ser Arg Asp
        355                 360                 365

Tyr Arg Lys Tyr Asp Tyr Trp Gly Gln Gly Thr Leu Val Thr Val Ser
    370                 375                 380

Ser
385

<210> SEQ ID NO 3
<211> LENGTH: 117
<212> TYPE: PRT
<213> ORGANISM: Artificial sequence
<220> FEATURE:
<223> OTHER INFORMATION: Nanobody

<400> SEQUENCE: 3

Glu Val Gln Leu Val Glu Ser Gly Gly Gly Leu Val Gln Ala Gly Gly
1               5                   10                  15

Ser Leu Arg Leu Ser Cys Ala Ala Ser Arg Ser Ile Gly Arg Leu Asp
            20                  25                  30

Arg Met Gly Trp Tyr Arg His Arg Thr Gly Glu Pro Arg Glu Leu Val
        35                  40                  45

Ala Thr Ile Thr Gly Gly Ser Ser Ile Asn Tyr Gly Asp Phe Val Lys
    50                  55                  60

Gly Arg Phe Thr Ile Ser Ile Asp Asn Ala Lys Asn Thr Val Tyr Leu
65                  70                  75                  80

Gln Met Asn Asn Leu Lys Pro Glu Asp Thr Ala Val Tyr Tyr Cys Asn
                85                  90                  95

Phe Asn Lys Tyr Val Thr Ser Arg Asp Thr Trp Gly Gln Gly Thr Gln
            100                 105                 110
```

```
Val Thr Val Ser Ser
        115

<210> SEQ ID NO 4
<211> LENGTH: 140
<212> TYPE: PRT
<213> ORGANISM: Artificial sequence
<220> FEATURE:
<223> OTHER INFORMATION: Nanobody

<400> SEQUENCE: 4

Glu Val Gln Leu Val Glu Ser Gly Gly Gly Leu Val Gln Ala Gly Gly
1               5                   10                  15

Ser Leu Arg Leu Ser Cys Ala Ala Ser Arg Ser Ile Gly Arg Leu Asp
            20                  25                  30

Arg Met Gly Trp Tyr Arg His Arg Thr Gly Glu Pro Arg Glu Leu Val
        35                  40                  45

Ala Thr Ile Thr Gly Gly Ser Ser Ile Asn Tyr Gly Asp Phe Val Lys
    50                  55                  60

Gly Arg Phe Thr Ile Ser Ile Asp Asn Ala Lys Asn Thr Val Tyr Leu
65                  70                  75                  80

Gln Met Asn Asn Leu Lys Pro Glu Asp Thr Ala Val Tyr Tyr Cys Asn
                85                  90                  95

Phe Asn Lys Tyr Val Thr Ser Arg Asp Thr Trp Gly Gln Gly Thr Gln
            100                 105                 110

Val Thr Val Ser Ser Ala Ala Ala Glu Gln Lys Leu Ile Ser Glu Glu
        115                 120                 125

Asp Leu Asn Gly Ala Ala His His His His His
    130                 135                 140

<210> SEQ ID NO 5
<211> LENGTH: 117
<212> TYPE: PRT
<213> ORGANISM: Artificial sequence
<220> FEATURE:
<223> OTHER INFORMATION: Nanobody

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Arg Ser Ile Gly Arg Leu Asp
            20                  25                  30

Arg Met Gly Trp Tyr Arg His Arg Pro Gly Glu Pro Arg Glu Leu Val
        35                  40                  45

Ala Thr Ile Thr Gly Gly Ser Ser Ile Asn Tyr Gly Asp Ser Val Lys
    50                  55                  60

Gly Arg Phe Thr Ile Ser Ile Asp Asn Ser Lys Asn Thr Val Tyr Leu
65                  70                  75                  80

Gln Met Asn Ser Leu Arg Pro Glu Asp Thr Ala Val Tyr Tyr Cys Asn
                85                  90                  95

Phe Asn Lys Tyr Val Thr Ser Arg Asp Thr Trp Gly Gln Gly Thr Leu
            100                 105                 110

Val Thr Val Ser Ser
        115

<210> SEQ ID NO 6
<211> LENGTH: 125
<212> TYPE: PRT
<213> ORGANISM: Artificial sequence
```

<220> FEATURE:
<223> OTHER INFORMATION: Nanobody

<400> SEQUENCE: 6

His His His His His His Glu Val Gln Leu Val Glu Ser Gly Gly Gly
1               5                   10                  15

Leu Val Gln Pro Gly Gly Ser Leu Arg Leu Ser Cys Ala Ala Ser Arg
            20                  25                  30

Ser Ile Gly Arg Leu Asp Arg Met Gly Trp Tyr Arg His Arg Pro Gly
        35                  40                  45

Glu Pro Arg Glu Leu Val Ala Thr Ile Thr Gly Gly Ser Ser Ile Asn
    50                  55                  60

Tyr Gly Asp Ser Val Lys Gly Arg Phe Thr Ile Ser Ile Asp Asn Ser
65                  70                  75                  80

Lys Asn Thr Val Tyr Leu Gln Met Asn Ser Leu Arg Pro Glu Asp Thr
                85                  90                  95

Ala Val Tyr Tyr Cys Asn Phe Asn Lys Tyr Val Thr Ser Arg Asp Thr
            100                 105                 110

Trp Gly Gln Gly Thr Leu Val Thr Val Ser Ser Ala Ala
        115                 120                 125

<210> SEQ ID NO 7
<211> LENGTH: 124
<212> TYPE: PRT
<213> ORGANISM: Artificial sequence
<220> FEATURE:
<223> OTHER INFORMATION: Nanobody

<400> SEQUENCE: 7

His His His His His His Glu Val Gln Leu Val Glu Ser Gly Gly Gly
1               5                   10                  15

Leu Val Gln Pro Gly Gly Ser Leu Arg Leu Ser Cys Ala Ala Ser Arg
            20                  25                  30

Ser Ile Gly Arg Leu Asp Arg Met Gly Trp Tyr Arg His Arg Pro Gly
        35                  40                  45

Glu Pro Arg Glu Leu Val Ala Thr Ile Thr Gly Gly Ser Ser Ile Asn
    50                  55                  60

Tyr Gly Asp Ser Val Lys Gly Arg Phe Thr Ile Ser Ile Asp Asn Ser
65                  70                  75                  80

Lys Asn Thr Val Tyr Leu Gln Met Asn Ser Leu Arg Pro Glu Asp Thr
                85                  90                  95

Ala Val Tyr Tyr Cys Asn Phe Asn Lys Tyr Val Thr Ser Arg Asp Thr
            100                 105                 110

Trp Gly Gln Gly Thr Leu Val Thr Val Ser Ser Ala
        115                 120

<210> SEQ ID NO 8
<211> LENGTH: 124
<212> TYPE: PRT
<213> ORGANISM: Artificial sequence
<220> FEATURE:
<223> OTHER INFORMATION: Nanobody

<400> SEQUENCE: 8

His His His His His His Glu Val Gln Leu Val Glu Ser Gly Gly Gly
1               5                   10                  15

Leu Val Gln Pro Gly Gly Ser Leu Arg Leu Ser Cys Ala Ala Ser Arg
            20                  25                  30

```
Ser Ile Gly Arg Leu Asp Arg Met Gly Trp Tyr Arg His Arg Pro Gly
            35                  40                  45

Glu Pro Arg Glu Leu Val Ala Thr Ile Thr Gly Gly Ser Ser Ile Asn
 50                      55                  60

Tyr Gly Asp Ser Val Lys Gly Arg Phe Thr Ile Ser Ile Asp Asn Ser
 65                  70                  75                  80

Lys Asn Thr Val Tyr Leu Gln Met Asn Ser Leu Arg Pro Glu Asp Thr
                 85                  90                  95

Ala Val Tyr Tyr Cys Asn Phe Asn Lys Tyr Val Thr Ser Arg Asp Thr
                100                 105                 110

Trp Gly Gln Gly Thr Leu Val Thr Val Ser Ser Gly
            115                 120
```

<210> SEQ ID NO 9
<211> LENGTH: 125
<212> TYPE: PRT
<213> ORGANISM: Artificial sequence
<220> FEATURE:
<223> OTHER INFORMATION: Nanobody

<400> SEQUENCE: 9

```
His His His His His His Glu Val Gln Leu Val Glu Ser Gly Gly Gly
 1               5                  10                  15

Leu Val Gln Pro Gly Gly Ser Leu Arg Leu Ser Cys Ala Ala Ser Arg
             20                  25                  30

Ser Ile Gly Arg Leu Asp Arg Met Gly Trp Tyr Arg His Arg Pro Gly
            35                  40                  45

Glu Pro Arg Glu Leu Val Ala Thr Ile Thr Gly Gly Ser Ser Ile Asn
 50                      55                  60

Tyr Gly Asp Ser Val Lys Gly Arg Phe Thr Ile Ser Ile Asp Asn Ser
 65                  70                  75                  80

Lys Asn Thr Val Tyr Leu Gln Met Asn Ser Leu Arg Pro Glu Asp Thr
                 85                  90                  95

Ala Val Tyr Tyr Cys Asn Phe Asn Lys Tyr Val Thr Ser Arg Asp Thr
                100                 105                 110

Trp Gly Gln Gly Thr Leu Val Thr Val Ser Ser Gly Gly
            115                 120                 125
```

<210> SEQ ID NO 10
<211> LENGTH: 126
<212> TYPE: PRT
<213> ORGANISM: Artificial sequence
<220> FEATURE:
<223> OTHER INFORMATION: Nanobody

<400> SEQUENCE: 10

```
His His His His His His Glu Val Gln Leu Val Glu Ser Gly Gly Gly
 1               5                  10                  15

Leu Val Gln Pro Gly Gly Ser Leu Arg Leu Ser Cys Ala Ala Ser Arg
             20                  25                  30

Ser Ile Gly Arg Leu Asp Arg Met Gly Trp Tyr Arg His Arg Pro Gly
            35                  40                  45

Glu Pro Arg Glu Leu Val Ala Thr Ile Thr Gly Gly Ser Ser Ile Asn
 50                      55                  60

Tyr Gly Asp Ser Val Lys Gly Arg Phe Thr Ile Ser Ile Asp Asn Ser
 65                  70                  75                  80

Lys Asn Thr Val Tyr Leu Gln Met Asn Ser Leu Arg Pro Glu Asp Thr
                 85                  90                  95
```

Ala Val Tyr Tyr Cys Asn Phe Asn Lys Tyr Val Thr Ser Arg Asp Thr
            100                 105                 110

Trp Gly Gln Gly Thr Leu Val Thr Val Ser Ser Gly Gly Gly
        115                 120                 125

<210> SEQ ID NO 11
<211> LENGTH: 123
<212> TYPE: PRT
<213> ORGANISM: Artificial sequence
<220> FEATURE:
<223> OTHER INFORMATION: Nanobody

<400> SEQUENCE: 11

His His His His His His Glu Val Gln Leu Val Glu Ser Gly Gly Gly
1               5                   10                  15

Leu Val Gln Ala Gly Gly Ser Leu Arg Leu Ser Cys Ala Ala Ser Arg
            20                  25                  30

Ser Ile Gly Arg Leu Asp Arg Met Gly Trp Tyr Arg His Arg Pro Gly
        35                  40                  45

Glu Pro Arg Glu Leu Val Ala Thr Ile Thr Gly Gly Ser Ser Ile Asn
    50                  55                  60

Tyr Gly Asp Ser Val Lys Gly Arg Phe Thr Ile Ser Ile Asp Asn Ser
65                  70                  75                  80

Lys Asn Thr Val Tyr Leu Gln Met Asn Ser Leu Arg Pro Glu Asp Thr
                85                  90                  95

Ala Val Tyr Tyr Cys Asn Phe Asn Lys Tyr Val Thr Ser Arg Asp Thr
            100                 105                 110

Trp Gly Gln Gly Thr Leu Val Thr Val Ser Ser
        115                 120

<210> SEQ ID NO 12
<211> LENGTH: 123
<212> TYPE: PRT
<213> ORGANISM: Artificial sequence
<220> FEATURE:
<223> OTHER INFORMATION: Nanobody

<400> SEQUENCE: 12

His His His His His His Glu Val Gln Leu Val Glu Ser Gly Gly Gly
1               5                   10                  15

Leu Val Gln Pro Gly Gly Ser Leu Arg Leu Ser Cys Ala Ala Ser Arg
            20                  25                  30

Ser Ile Gly Arg Leu Asp Arg Met Gly Trp Tyr Arg His Arg Pro Gly
        35                  40                  45

Glu Pro Arg Glu Leu Val Ala Thr Ile Thr Gly Gly Ser Ser Ile Asn
    50                  55                  60

Tyr Gly Asp Ser Val Lys Gly Arg Phe Thr Ile Ser Ile Asp Asn Ser
65                  70                  75                  80

Lys Asn Thr Val Tyr Leu Gln Met Asn Ser Leu Lys Pro Glu Asp Thr
                85                  90                  95

Ala Val Tyr Tyr Cys Asn Phe Asn Lys Tyr Val Thr Ser Arg Asp Thr
            100                 105                 110

Trp Gly Gln Gly Thr Leu Val Thr Val Ser Ser
        115                 120

<210> SEQ ID NO 13
<211> LENGTH: 123
<212> TYPE: PRT

<213> ORGANISM: Artificial sequence
<220> FEATURE:
<223> OTHER INFORMATION: Nanobody

<400> SEQUENCE: 13

```
His His His His His His Glu Val Gln Leu Val Glu Ser Gly Gly Gly
1               5                   10                  15

Leu Val Gln Ala Gly Gly Ser Leu Arg Leu Ser Cys Ala Ala Ser Arg
            20                  25                  30

Ser Ile Gly Arg Leu Asp Arg Met Gly Trp Tyr Arg His Arg Pro Gly
        35                  40                  45

Glu Pro Arg Glu Leu Val Ala Thr Ile Thr Gly Gly Ser Ser Ile Asn
    50                  55                  60

Tyr Gly Asp Ser Val Lys Gly Arg Phe Thr Ile Ser Ile Asp Asn Ser
65                  70                  75                  80

Lys Asn Thr Val Tyr Leu Gln Met Asn Ser Leu Arg Pro Glu Asp Thr
                85                  90                  95

Ala Val Tyr Tyr Cys Asn Phe Asn Lys Tyr Val Thr Ser Arg Asp Thr
            100                 105                 110

Trp Gly Gln Gly Thr Gln Val Thr Val Ser Ser
        115                 120
```

<210> SEQ ID NO 14
<211> LENGTH: 123
<212> TYPE: PRT
<213> ORGANISM: Artificial sequence
<220> FEATURE:
<223> OTHER INFORMATION: Nanobody

<400> SEQUENCE: 14

```
His His His His His His Glu Val Gln Leu Val Glu Ser Gly Gly Gly
1               5                   10                  15

Leu Val Gln Pro Gly Gly Ser Leu Arg Leu Ser Cys Ala Ala Ser Arg
            20                  25                  30

Ser Ile Gly Arg Leu Asp Arg Met Gly Trp Tyr Arg His Arg Pro Gly
        35                  40                  45

Glu Pro Arg Glu Leu Val Ala Thr Ile Thr Gly Gly Ser Ser Ile Asn
    50                  55                  60

Tyr Gly Asp Ser Val Lys Gly Arg Phe Thr Ile Ser Ile Asp Asn Ser
65                  70                  75                  80

Lys Asn Thr Val Tyr Leu Gln Met Asn Ser Leu Arg Pro Glu Asp Thr
                85                  90                  95

Ala Val Tyr Tyr Cys Asn Phe Asn Lys Tyr Val Thr Ser Arg Asp Thr
            100                 105                 110

Trp Gly Gln Gly Thr Gln Val Thr Val Ser Ser
        115                 120
```

<210> SEQ ID NO 15
<211> LENGTH: 123
<212> TYPE: PRT
<213> ORGANISM: Artificial sequence
<220> FEATURE:
<223> OTHER INFORMATION: Nanobody

<400> SEQUENCE: 15

```
His His His His His His Glu Val Gln Leu Val Glu Ser Gly Gly Gly
1               5                   10                  15

Leu Val Gln Pro Gly Gly Ser Leu Arg Leu Ser Cys Ala Ala Ser Arg
            20                  25                  30
```

Ser Ile Gly Arg Leu Asp Arg Met Gly Trp Tyr Arg His Arg Pro Gly
            35                  40                  45

Glu Pro Arg Glu Leu Val Ala Thr Ile Thr Gly Ser Ser Ile Asn
 50                  55                  60

Tyr Gly Asp Ser Val Lys Gly Arg Phe Thr Ile Ser Ile Asp Asn Ser
 65                  70                  75                  80

Lys Asn Thr Val Tyr Leu Gln Met Asn Ser Leu Arg Pro Glu Asp Thr
                85                  90                  95

Ala Val Tyr Tyr Cys Asn Phe Asn Lys Tyr Val Thr Ser Arg Asp Thr
                100                 105                 110

Trp Gly Gln Gly Thr Leu Val Gln Val Ser Ser
            115                 120

<210> SEQ ID NO 16
<211> LENGTH: 123
<212> TYPE: PRT
<213> ORGANISM: Artificial sequence
<220> FEATURE:
<223> OTHER INFORMATION: Nanobody

<400> SEQUENCE: 16

His His His His His His Glu Val Gln Leu Val Glu Ser Gly Gly Gly
 1               5                  10                  15

Ser Val Gln Pro Gly Gly Ser Leu Arg Leu Ser Cys Ala Ala Ser Arg
                20                  25                  30

Ser Ile Gly Arg Leu Asp Arg Met Gly Trp Tyr Arg His Arg Pro Gly
            35                  40                  45

Glu Pro Arg Glu Leu Val Ala Thr Ile Thr Gly Ser Ser Ile Asn
 50                  55                  60

Tyr Gly Asp Ser Val Lys Gly Arg Phe Thr Ile Ser Ile Asp Asn Ser
 65                  70                  75                  80

Lys Asn Thr Val Tyr Leu Gln Met Asn Ser Leu Arg Pro Glu Asp Thr
                85                  90                  95

Ala Val Tyr Tyr Cys Asn Phe Asn Lys Tyr Val Thr Ser Arg Asp Thr
                100                 105                 110

Trp Gly Gln Gly Thr Leu Val Thr Val Ser Ser
            115                 120

<210> SEQ ID NO 17
<211> LENGTH: 121
<212> TYPE: PRT
<213> ORGANISM: Artificial sequence
<220> FEATURE:
<223> OTHER INFORMATION: Nanobody

<400> SEQUENCE: 17

Glu Val Gln Leu Val Glu Ser Gly Gly Gly Leu Val Gln Pro Gly Gly
 1               5                  10                  15

Ser Leu Arg Leu Ser Cys Ala Ala Ser Gly Ser Val Phe Lys Ile Asn
                20                  25                  30

Val Met Ala Trp Tyr Arg Gln Ala Pro Gly Lys Gly Arg Glu Leu Val
            35                  40                  45

Ala Gly Ile Ile Ser Gly Gly Ser Thr Ser Tyr Ala Asp Ser Val Lys
 50                  55                  60

Gly Arg Phe Thr Ile Ser Arg Asp Asn Ala Lys Asn Thr Leu Tyr Leu
 65                  70                  75                  80

Gln Met Asn Ser Leu Arg Pro Glu Asp Thr Ala Val Tyr Tyr Cys Ala

```
                        85                  90                  95

Phe Ile Thr Thr Glu Ser Asp Tyr Asp Leu Gly Arg Arg Tyr Trp Gly
                       100                 105                 110

Gln Gly Thr Leu Val Thr Val Ser Ser
                115                 120

<210> SEQ ID NO 18
<211> LENGTH: 146
<212> TYPE: PRT
<213> ORGANISM: Artificial sequence
<220> FEATURE:
<223> OTHER INFORMATION: Nanobody

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Val Phe Lys Ile Asn
                20                  25                  30

Val Met Ala Trp Tyr Arg Gln Ala Pro Gly Lys Gly Arg Glu Leu Val
            35                  40                  45

Ala Gly Ile Ile Ser Gly Gly Ser Thr Ser Tyr Ala Asp Ser Val Lys
        50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Ile Thr Thr Glu Ser Asp Tyr Asp Leu Gly Arg Arg Tyr Trp Gly
                       100                 105                 110

Gln Gly Thr Leu Val Thr Val Ser Ser Gly Gly Gly Gly Ser Gly Gly
                115                 120                 125

Gly Ser Arg Asp Trp Asp Phe Asp Val Phe Gly Gly Thr Pro Val
        130                 135                 140

Gly Gly
145

<210> SEQ ID NO 19
<211> LENGTH: 151
<212> TYPE: PRT
<213> ORGANISM: Artificial sequence
<220> FEATURE:
<223> OTHER INFORMATION: Nanobody

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ile Ala Ser Gly Leu Pro Phe Ser Thr Lys
                20                  25                  30

Ser Met Gly Trp Phe Arg Gln Ala Pro Gly Lys Glu Arg Glu Phe Val
            35                  40                  45

Ala Arg Ile Ser Pro Gly Gly Thr Ser Arg Tyr Tyr Gly Asp Phe Val
        50                  55                  60

Lys Gly Arg Phe Ala Ile Ser Arg Asp Asn Ala Lys Asn Thr Thr Trp
65                  70                  75                  80

Leu Gln Met Asn Ser Leu Lys Ala Glu Asp Thr Ala Val Tyr Tyr Cys
                85                  90                  95

Ala Ser Gly Glu Arg Ser Thr Tyr Ile Gly Ser Asn Tyr Tyr Arg Thr
                       100                 105                 110
```

Asn Glu Tyr Asp Tyr Trp Gly Thr Gly Thr Gln Val Thr Val Ser Ser
            115                 120                 125

Ala Ala Ala Glu Gln Lys Leu Ile Ser Glu Glu Asp Leu Asn Gly Ala
    130                 135                 140

Ala His His His His His His
145                 150

<210> SEQ ID NO 20
<211> LENGTH: 128
<212> TYPE: PRT
<213> ORGANISM: Artificial sequence
<220> FEATURE:
<223> OTHER INFORMATION: Nanobody

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ile Ala Ser Gly Leu Pro Phe Ser Thr Lys
            20                  25                  30

Ser Met Gly Trp Phe Arg Gln Ala Pro Gly Lys Glu Arg Glu Phe Val
        35                  40                  45

Ala Arg Ile Ser Pro Gly Gly Thr Ser Arg Tyr Tyr Gly Asp Phe Val
    50                  55                  60

Lys Gly Arg Phe Ala Ile Ser Arg Asp Asn Ala Lys Asn Thr Thr Trp
65                  70                  75                  80

Leu Gln Met Asn Ser Leu Lys Ala Glu Asp Thr Ala Val Tyr Tyr Cys
                85                  90                  95

Ala Ser Gly Glu Arg Ser Thr Tyr Ile Gly Ser Asn Tyr Arg Thr
            100                 105                 110

Asn Glu Tyr Asp Tyr Trp Gly Thr Gly Thr Gln Val Thr Val Ser Ser
            115                 120                 125

<210> SEQ ID NO 21
<211> LENGTH: 151
<212> TYPE: PRT
<213> ORGANISM: Artificial sequence
<220> FEATURE:
<223> OTHER INFORMATION: Nanobody

<400> SEQUENCE: 21

Glu Val Gln Leu Leu Glu Ser Gly Gly Gly Leu Val Gln Pro Gly Gly
1               5                   10                  15

Ser Leu Arg Leu Ser Cys Ala Ala Ser Gly Leu Pro Phe Ser Thr Lys
            20                  25                  30

Ser Met Gly Trp Phe Arg Gln Ala Pro Gly Lys Gly Arg Glu Phe Val
        35                  40                  45

Ser Arg Ile Ser Pro Gly Gly Thr Ser Arg Tyr Tyr Gly Asp Phe Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Gly Glu Arg Ser Thr Tyr Ile Gly Ser Asn Tyr Arg Thr
            100                 105                 110

Asn Glu Tyr Asp Tyr Trp Gly Gln Gly Thr Leu Val Thr Val Ser Ser
            115                 120                 125

Ala Ala Ala Glu Gln Lys Leu Ile Ser Glu Glu Asp Leu Asn Gly Ala
    130                 135                 140

Ala His His His His His
145                 150

<210> SEQ ID NO 22
<211> LENGTH: 128
<212> TYPE: PRT
<213> ORGANISM: Artificial sequence
<220> FEATURE:
<223> OTHER INFORMATION: Nanobody

<400> SEQUENCE: 22

Glu Val Gln Leu Leu Glu Ser Gly Gly Gly Leu Val Gln Pro Gly Gly
1               5                   10                  15

Ser Leu Arg Leu Ser Cys Ala Ala Ser Gly Leu Pro Phe Ser Thr Lys
            20                  25                  30

Ser Met Gly Trp Phe Arg Gln Ala Pro Gly Lys Gly Arg Glu Phe Val
        35                  40                  45

Ser Arg Ile Ser Pro Gly Gly Thr Ser Arg Tyr Tyr Gly Asp Phe Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Gly Glu Arg Ser Thr Tyr Ile Gly Ser Asn Tyr Tyr Arg Thr
            100                 105                 110

Asn Glu Tyr Asp Tyr Trp Gly Gln Gly Thr Leu Val Thr Val Ser Ser
        115                 120                 125

<210> SEQ ID NO 23
<211> LENGTH: 134
<212> TYPE: PRT
<213> ORGANISM: Artificial sequence
<220> FEATURE:
<223> OTHER INFORMATION: Nanobody

<400> SEQUENCE: 23

His His His His His His Glu Val Gln Leu Val Glu Ser Gly Gly Gly
1               5                   10                  15

Leu Val Gln Ala Gly Gly Ser Leu Arg Leu Ser Cys Ala Ala Ser Gly
            20                  25                  30

Arg Thr Phe Asn Asn Tyr Ala Met Gly Trp Phe Arg Arg Ala Pro Gly
        35                  40                  45

Lys Glu Arg Glu Phe Val Ala Ala Ile Thr Arg Ser Gly Val Arg Ser
    50                  55                  60

Gly Val Ser Ala Ile Tyr Gly Asp Ser Val Lys Asp Arg Phe Thr Ile
65                  70                  75                  80

Ser Arg Asp Asn Ala Lys Asn Thr Leu Tyr Leu Gln Met Asn Ser Leu
                85                  90                  95

Lys Pro Glu Asp Thr Ala Val Tyr Thr Cys Ala Ala Ser Ala Ile Gly
            100                 105                 110

Ser Gly Ala Leu Arg Arg Phe Glu Tyr Asp Tyr Ser Gly Gln Gly Thr
        115                 120                 125

Gln Val Thr Val Ser Ser
    130

<210> SEQ ID NO 24
<211> LENGTH: 134
<212> TYPE: PRT

<213> ORGANISM: Artificial sequence
<220> FEATURE:
<223> OTHER INFORMATION: Nanobody

<400> SEQUENCE: 24

His His His His His His Glu Val Gln Leu Val Glu Ser Gly Gly Gly
1               5                   10                  15

Leu Val Gln Pro Gly Gly Ser Leu Arg Leu Ser Cys Ala Ala Ser Gly
            20                  25                  30

Arg Thr Phe Asn Asn Tyr Ala Met Gly Trp Phe Arg Ala Pro Gly
            35                  40                  45

Lys Glu Arg Glu Phe Val Ala Ala Ile Thr Arg Ser Gly Val Arg Ser
50                  55                  60

Gly Val Ser Ala Ile Tyr Gly Asp Ser Val Lys Asp Arg Phe Thr Ile
65                  70                  75                  80

Ser Arg Asp Asn Ala Lys Asn Thr Leu Tyr Leu Gln Met Asn Ser Leu
                85                  90                  95

Lys Pro Glu Asp Thr Ala Val Tyr Thr Cys Ala Ala Ser Ala Ile Gly
            100                 105                 110

Ser Gly Ala Leu Arg Arg Phe Glu Tyr Asp Tyr Ser Gly Gln Gly Thr
        115                 120                 125

Gln Val Thr Val Ser Ser
    130

<210> SEQ ID NO 25
<211> LENGTH: 134
<212> TYPE: PRT
<213> ORGANISM: Artificial sequence
<220> FEATURE:
<223> OTHER INFORMATION: Nanobody

<400> SEQUENCE: 25

His His His His His His Glu Val Gln Leu Val Glu Ser Gly Gly Gly
1               5                   10                  15

Leu Val Gln Ala Gly Gly Ser Leu Arg Leu Ser Cys Ala Ala Ser Gly
            20                  25                  30

Arg Thr Phe Asn Asn Tyr Ala Met Gly Trp Phe Arg Ala Pro Gly
            35                  40                  45

Lys Glu Arg Glu Phe Val Ala Ala Ile Thr Arg Ser Gly Val Arg Ser
50                  55                  60

Gly Val Ser Ala Ile Tyr Gly Asp Ser Val Lys Asp Arg Phe Thr Ile
65                  70                  75                  80

Ser Arg Asp Asn Ala Lys Asn Thr Leu Tyr Leu Gln Met Asn Ser Leu
                85                  90                  95

Arg Pro Glu Asp Thr Ala Val Tyr Thr Cys Ala Ala Ser Ala Ile Gly
            100                 105                 110

Ser Gly Ala Leu Arg Arg Phe Glu Tyr Asp Tyr Ser Gly Gln Gly Thr
        115                 120                 125

Gln Val Thr Val Ser Ser
    130

<210> SEQ ID NO 26
<211> LENGTH: 134
<212> TYPE: PRT
<213> ORGANISM: Artificial sequence
<220> FEATURE:
<223> OTHER INFORMATION: Nanobody

<400> SEQUENCE: 26

```
His His His His His His Glu Val Gln Leu Val Glu Ser Gly Gly Gly
1               5                   10                  15

Leu Val Gln Ala Gly Gly Ser Leu Arg Leu Ser Cys Ala Ala Ser Gly
            20                  25                  30

Arg Thr Phe Asn Asn Tyr Ala Met Gly Trp Phe Arg Arg Ala Pro Gly
        35                  40                  45

Lys Glu Arg Glu Phe Val Ala Ala Ile Thr Arg Ser Gly Val Arg Ser
    50                  55                  60

Gly Val Ser Ala Ile Tyr Gly Asp Ser Val Lys Asp Arg Phe Thr Ile
65                  70                  75                  80

Ser Arg Asp Asn Ala Lys Asn Thr Leu Tyr Leu Gln Met Asn Ser Leu
                85                  90                  95

Lys Pro Glu Asp Thr Ala Val Tyr Thr Cys Ala Ala Ser Ala Ile Gly
            100                 105                 110

Ser Gly Ala Leu Arg Arg Phe Glu Tyr Asp Tyr Ser Gly Gln Gly Thr
            115                 120                 125

Leu Val Thr Val Ser Ser
    130
```

<210> SEQ ID NO 27
<211> LENGTH: 134
<212> TYPE: PRT
<213> ORGANISM: Artificial sequence
<220> FEATURE:
<223> OTHER INFORMATION: Nanobody

<400> SEQUENCE: 27

```
His His His His His His Glu Val Gln Leu Val Glu Ser Gly Gly Gly
1               5                   10                  15

Leu Val Gln Pro Gly Gly Ser Leu Arg Leu Ser Cys Ala Ala Ser Gly
            20                  25                  30

Arg Thr Phe Asn Asn Tyr Ala Met Gly Trp Phe Arg Arg Ala Pro Gly
        35                  40                  45

Lys Glu Arg Glu Phe Val Ala Ala Ile Thr Arg Ser Gly Val Arg Ser
    50                  55                  60

Gly Val Ser Ala Ile Tyr Gly Asp Ser Val Lys Asp Arg Phe Thr Ile
65                  70                  75                  80

Ser Arg Asp Asn Ala Lys Asn Thr Leu Tyr Leu Gln Met Asn Ser Leu
                85                  90                  95

Arg Pro Glu Asp Thr Ala Val Tyr Thr Cys Ala Ala Ser Ala Ile Gly
            100                 105                 110

Ser Gly Ala Leu Arg Arg Phe Glu Tyr Asp Tyr Ser Gly Gln Gly Thr
            115                 120                 125

Leu Val Thr Val Ser Ser
    130
```

<210> SEQ ID NO 28
<211> LENGTH: 134
<212> TYPE: PRT
<213> ORGANISM: Artificial sequence
<220> FEATURE:
<223> OTHER INFORMATION: Nanobody

<400> SEQUENCE: 28

```
His His His His His His Glu Val Gln Leu Val Glu Ser Gly Gly Gly
1               5                   10                  15

Leu Val Gln Pro Gly Gly Ser Leu Arg Leu Ser Cys Ala Ala Ser Gly
```

```
                    20                  25                  30
Arg Thr Phe Asn Asn Tyr Ala Met Gly Trp Phe Arg Gln Ala Pro Gly
            35                  40                  45

Lys Glu Arg Glu Phe Val Ala Ala Ile Thr Arg Ser Gly Val Arg Ser
        50                  55                  60

Gly Val Ser Ala Ile Tyr Gly Asp Ser Val Lys Asp Arg Phe Thr Ile
 65                  70                  75                  80

Ser Arg Asp Asn Ala Lys Asn Thr Leu Tyr Leu Gln Met Asn Ser Leu
                85                  90                  95

Arg Pro Glu Asp Thr Ala Val Tyr Tyr Cys Ala Ala Ser Ala Ile Gly
            100                 105                 110

Ser Gly Ala Leu Arg Arg Phe Glu Tyr Asp Tyr Ser Gly Gln Gly Thr
                115                 120                 125

Leu Val Thr Val Ser Ser
            130

<210> SEQ ID NO 29
<211> LENGTH: 137
<212> TYPE: PRT
<213> ORGANISM: Artificial sequence
<220> FEATURE:
<223> OTHER INFORMATION: Nanobody

<400> SEQUENCE: 29

His His His His His His Glu Val Gln Leu Val Glu Ser Gly Gly Gly
 1               5                  10                  15

Leu Val Gln Pro Gly Gly Ser Leu Arg Leu Ser Cys Ala Ala Ser Gly
            20                  25                  30

Arg Thr Phe Asn Asn Tyr Ala Met Gly Trp Phe Arg Gln Ala Pro Gly
            35                  40                  45

Lys Glu Arg Glu Phe Val Ala Ala Ile Thr Arg Ser Gly Val Arg Ser
        50                  55                  60

Gly Val Ser Ala Ile Tyr Gly Asp Ser Val Lys Asp Arg Phe Thr Ile
 65                  70                  75                  80

Ser Arg Asp Asn Ala Lys Asn Thr Leu Tyr Leu Gln Met Asn Ser Leu
                85                  90                  95

Arg Pro Glu Asp Thr Ala Val Tyr Tyr Cys Ala Ala Ser Ala Ile Gly
            100                 105                 110

Ser Gly Ala Leu Arg Arg Phe Glu Tyr Asp Tyr Ser Gly Gln Gly Thr
                115                 120                 125

Leu Val Thr Val Ser Ser Ala Ala Ala
            130                 135

<210> SEQ ID NO 30
<211> LENGTH: 137
<212> TYPE: PRT
<213> ORGANISM: Artificial sequence
<220> FEATURE:
<223> OTHER INFORMATION: Nanobody

<400> SEQUENCE: 30

His His His His His His Glu Val Gln Leu Val Glu Ser Gly Gly Gly
 1               5                  10                  15

Leu Val Gln Pro Gly Gly Ser Leu Arg Leu Ser Cys Ala Ala Ser Gly
            20                  25                  30

Arg Thr Phe Asn Asn Tyr Ala Met Gly Trp Phe Arg Gln Ala Pro Gly
            35                  40                  45
```

```
Lys Glu Arg Glu Phe Val Ala Ile Thr Arg Ser Gly Val Arg Ser
 50                  55                  60

Gly Val Ser Ala Ile Tyr Gly Asp Ser Val Lys Asp Arg Phe Thr Ile
 65                  70                  75                  80

Ser Arg Asp Asn Ala Lys Asn Thr Leu Tyr Leu Gln Met Asn Ser Leu
                 85                  90                  95

Arg Pro Glu Asp Thr Ala Val Tyr Tyr Cys Ala Ala Ser Ala Ile Gly
            100                 105                 110

Ser Gly Ala Leu Arg Arg Phe Glu Tyr Asp Tyr Ser Gly Gln Gly Thr
            115                 120                 125

Leu Val Thr Val Ser Ser Ala Ala Ala
            130                 135
```

<210> SEQ ID NO 31
<211> LENGTH: 367
<212> TYPE: PRT
<213> ORGANISM: Artificial sequence
<220> FEATURE:
<223> OTHER INFORMATION: Nanobody

<400> SEQUENCE: 31

```
Asp Val Gln Leu Val Glu Ser Gly Gly Gly Leu Val Gln Pro Gly Gly
 1               5                  10                  15

Ser Leu Arg Leu Ser Cys Ala Ala Ser Arg Ser Ile Gly Arg Leu Asp
                 20                  25                  30

Arg Met Gly Trp Tyr Arg His Arg Pro Gly Glu Pro Arg Glu Leu Val
             35                  40                  45

Ala Thr Ile Thr Gly Gly Ser Ser Ile Asn Tyr Gly Asp Ser Val Lys
 50                  55                  60

Gly Arg Phe Thr Ile Ser Ile Asp Asn Ser Lys Asn Thr Val Tyr Leu
 65                  70                  75                  80

Gln Met Asn Ser Leu Arg Pro Glu Asp Thr Ala Val Tyr Tyr Cys Asn
                 85                  90                  95

Phe Asn Lys Tyr Val Thr Ser Arg Asp Thr Trp Gly Gln Gly Thr Leu
            100                 105                 110

Val Thr Val Ser Ser Gly Gly Gly Gly Ser Gly Gly Gly Ser Glu Val
            115                 120                 125

Gln Leu Val Glu Ser Gly Gly Gly Leu Val Gln Pro Gly Asn Ser Leu
            130                 135                 140

Arg Leu Ser Cys Ala Ala Ser Gly Phe Thr Phe Ser Ser Phe Gly Met
145                 150                 155                 160

Ser Trp Val Arg Gln Ala Pro Gly Lys Gly Leu Glu Trp Val Ser Ser
                165                 170                 175

Ile Ser Gly Ser Gly Ser Asp Thr Leu Tyr Ala Asp Ser Val Lys Gly
            180                 185                 190

Arg Phe Thr Ile Ser Arg Asp Asn Ala Lys Thr Thr Leu Tyr Leu Gln
            195                 200                 205

Met Asn Ser Leu Arg Pro Glu Asp Thr Ala Val Tyr Tyr Cys Thr Ile
            210                 215                 220

Gly Gly Ser Leu Ser Arg Ser Gln Gly Thr Leu Val Thr Val Ser
225                 230                 235                 240

Ser Gly Gly Gly Gly Ser Gly Gly Ser Glu Val Gln Leu Val Glu
                245                 250                 255

Ser Gly Gly Gly Leu Val Gln Pro Gly Gly Ser Leu Arg Leu Ser Cys
            260                 265                 270
```

```
Ala Ala Ser Arg Ser Ile Gly Arg Leu Asp Arg Met Gly Trp Tyr Arg
            275                 280                 285

His Arg Pro Gly Glu Pro Arg Glu Leu Val Ala Thr Ile Thr Gly Gly
290                 295                 300

Ser Ser Ile Asn Tyr Gly Asp Ser Val Lys Gly Arg Phe Thr Ile Ser
305                 310                 315                 320

Ile Asp Asn Ser Lys Asn Thr Val Tyr Leu Gln Met Asn Ser Leu Arg
                325                 330                 335

Pro Glu Asp Thr Ala Val Tyr Tyr Cys Asn Phe Asn Lys Tyr Val Thr
            340                 345                 350

Ser Arg Asp Thr Trp Gly Gln Gly Thr Leu Val Thr Val Ser Ser
355                 360                 365
```

<210> SEQ ID NO 32
<211> LENGTH: 368
<212> TYPE: PRT
<213> ORGANISM: Artificial sequence
<220> FEATURE:
<223> OTHER INFORMATION: Nanobody

<400> SEQUENCE: 32

```
Asp Val Gln Leu Val Glu Ser Gly Gly Gly Leu Val Gln Pro Gly Gly
1               5                   10                  15

Ser Leu Arg Leu Ser Cys Ala Ala Ser Arg Ser Ile Gly Arg Leu Asp
            20                  25                  30

Arg Met Gly Trp Tyr Arg His Arg Pro Gly Glu Pro Arg Glu Leu Val
        35                  40                  45

Ala Thr Ile Thr Gly Gly Ser Ser Ile Asn Tyr Gly Asp Ser Val Lys
    50                  55                  60

Gly Arg Phe Thr Ile Ser Ile Asp Asn Ser Lys Asn Thr Val Tyr Leu
65                  70                  75                  80

Gln Met Asn Ser Leu Arg Pro Glu Asp Thr Ala Val Tyr Tyr Cys Asn
                85                  90                  95

Phe Asn Lys Tyr Val Thr Ser Arg Asp Thr Trp Gly Gln Gly Thr Leu
            100                 105                 110

Val Thr Val Ser Ser Gly Gly Gly Gly Ser Gly Gly Gly Ser Glu Val
        115                 120                 125

Gln Leu Val Glu Ser Gly Gly Gly Leu Val Gln Pro Gly Asn Ser Leu
    130                 135                 140

Arg Leu Ser Cys Ala Ala Ser Gly Phe Thr Phe Ser Ser Phe Gly Met
145                 150                 155                 160

Ser Trp Val Arg Gln Ala Pro Gly Lys Gly Leu Glu Trp Val Ser Ser
                165                 170                 175

Ile Ser Gly Ser Gly Ser Asp Thr Leu Tyr Ala Asp Ser Val Lys Gly
            180                 185                 190

Arg Phe Thr Ile Ser Arg Asp Asn Ala Lys Thr Thr Leu Tyr Leu Gln
        195                 200                 205

Met Asn Ser Leu Arg Pro Glu Asp Thr Ala Val Tyr Tyr Cys Thr Ile
    210                 215                 220

Gly Gly Ser Leu Ser Arg Ser Ser Gln Gly Thr Leu Val Thr Val Ser
225                 230                 235                 240

Ser Gly Gly Gly Gly Ser Gly Gly Gly Ser Glu Val Gln Leu Val Glu
                245                 250                 255

Ser Gly Gly Gly Leu Val Gln Pro Gly Gly Ser Leu Arg Leu Ser Cys
            260                 265                 270
```

```
Ala Ala Ser Arg Ser Ile Gly Arg Leu Asp Arg Met Gly Trp Tyr Arg
            275                 280                 285

His Arg Pro Gly Glu Pro Arg Glu Leu Val Ala Thr Ile Thr Gly Gly
        290                 295                 300

Ser Ser Ile Asn Tyr Gly Asp Ser Val Lys Gly Arg Phe Thr Ile Ser
305                 310                 315                 320

Ile Asp Asn Ser Lys Asn Thr Val Tyr Leu Gln Met Asn Ser Leu Arg
                325                 330                 335

Pro Glu Asp Thr Ala Val Tyr Tyr Cys Asn Phe Asn Lys Tyr Val Thr
            340                 345                 350

Ser Arg Asp Thr Trp Gly Gln Gly Thr Leu Val Thr Val Ser Ser Ala
            355                 360                 365

<210> SEQ ID NO 33
<211> LENGTH: 5
<212> TYPE: PRT
<213> ORGANISM: Artificial sequence
<220> FEATURE:
<223> OTHER INFORMATION: C-terminal sequence

<400> SEQUENCE: 33

Val Thr Val Ser Ser
1               5

<210> SEQ ID NO 34
<211> LENGTH: 6
<212> TYPE: PRT
<213> ORGANISM: Artificial sequence
<220> FEATURE:
<223> OTHER INFORMATION: C-terminal sequence
<220> FEATURE:
<221> NAME/KEY: MISC_FEATURE
<222> LOCATION: (6)..(6)
<223> OTHER INFORMATION: X = a group (X)n, in which N = 1-10, preferably
      1-5 and X is any amino acid.

<400> SEQUENCE: 34

Val Thr Val Ser Ser Xaa
1               5

<210> SEQ ID NO 35
<211> LENGTH: 218
<212> TYPE: PRT
<213> ORGANISM: Mus musculus

<400> SEQUENCE: 35

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Ala Tyr
            20                  25                  30

Ser Met His Trp Val Lys Gln Ala Pro Gly Lys Gly Leu Lys Trp Met
        35                  40                  45

Gly Trp Ile Asn Thr Val Thr Gly Glu Pro Ala Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Ser Ser Leu Lys Asn Glu Asp Thr Ala Thr Tyr Phe Cys
                85                  90                  95

Thr Arg Gly Leu Ile His Phe Tyr Tyr Trp Gly Gln Gly Thr Thr Leu
            100                 105                 110

Thr Val Ser Ser Ala Lys Thr Thr Pro Pro Ser Val Tyr Pro Leu Ala
```

```
            115                 120                 125
Pro Gly Ser Ala Ala Gln Thr Asn Ser Met Val Thr Leu Gly Cys Leu
        130                 135                 140

Val Lys Gly Tyr Phe Pro Glu Pro Val Thr Val Thr Trp Asn Ser Gly
145                 150                 155                 160

Ser Leu Ser Ser Gly Val His Thr Phe Pro Ala Val Leu Gln Ser Asp
                165                 170                 175

Leu Tyr Thr Leu Ser Ser Val Thr Val Pro Ser Ser Thr Trp Pro
                180                 185                 190

Ser Glu Thr Val Thr Cys Asn Val Ala His Pro Ala Ser Ser Thr Lys
                195                 200                 205

Val Asp Lys Lys Ile Val Pro Arg Asp Cys
210                 215

<210> SEQ ID NO 36
<211> LENGTH: 214
<212> TYPE: PRT
<213> ORGANISM: Mus musculus

<400> SEQUENCE: 36

Asp Ile Gln Met Thr Gln Thr Pro Ser Ser Leu Ser Ala Ser Leu Gly
1               5                   10                  15

Gly Arg Val Thr Ile Thr Cys Lys Ala Ser Gln Asp Ile His Asn Phe
                20                  25                  30

Ile Ser Trp Tyr Gln His Lys Pro Gly Lys Val Pro Arg Leu Ile Ile
            35                  40                  45

His Asp Thr Ser Thr Leu Gln Pro Gly Ile Pro Ser Arg Phe Ser Gly
        50                  55                  60

Ser Gly Ser Gly Arg Asp Tyr Ser Phe Ser Ile Thr Asn Leu Glu Pro
65                  70                  75                  80

Glu Asp Ile Ala Thr Tyr Tyr Cys Leu His Tyr Asp Asn Leu Leu Arg
                85                  90                  95

Ser Phe Gly Gly Gly Thr Lys Leu Glu Ile Lys Arg Ala Asp Ala Ala
                100                 105                 110

Pro Thr Val Ser Ile Phe Pro Pro Ser Ser Glu Gln Leu Thr Ser Gly
            115                 120                 125

Gly Ala Ser Val Val Cys Phe Leu Asn Asn Phe Tyr Pro Lys Asp Ile
        130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
                180                 185                 190

Thr Cys Glu Ala Thr His Lys Thr Ser Thr Ser Pro Ile Val Lys Ser
                195                 200                 205

Phe Asn Arg Asn Glu Cys
            210

<210> SEQ ID NO 37
<211> LENGTH: 122
<212> TYPE: PRT
<213> ORGANISM: Artificial sequence
<220> FEATURE:
<223> OTHER INFORMATION: Nanobody or Nanobody construct

<400> SEQUENCE: 37
```

```
His His His His His Glu Val Gln Leu Val Ser Gly Gly Gly
1               5                  10                 15

Leu Val Gln Pro Gly Asn Ser Leu Arg Leu Ser Cys Ala Ala Ser Gly
            20                  25                  30

Phe Thr Phe Ser Ser Phe Gly Met Ser Trp Val Arg Gln Ala Pro Gly
            35                  40                  45

Lys Gly Leu Glu Trp Val Ser Ser Ile Ser Gly Ser Gly Ser Asp Thr
50                  55                  60

Leu Tyr Ala Asp Ser Val Lys Gly Arg Phe Thr Ile Ser Arg Asp Asn
65                  70                  75                  80

Ala Lys Thr Thr Leu Tyr Leu Gln Met Asn Ser Leu Arg Pro Glu Asp
            85                  90                  95

Thr Ala Val Tyr Tyr Cys Thr Ile Gly Gly Ser Leu Ser Arg Ser Ser
            100                 105                 110

Gln Gly Thr Leu Val Thr Val Ser Ser Ala
            115                 120
```

<210> SEQ ID NO 38
<211> LENGTH: 271
<212> TYPE: PRT
<213> ORGANISM: Artificial sequence
<220> FEATURE:
<223> OTHER INFORMATION: Nanobody or Nanobody construct

<400> SEQUENCE: 38

```
Glu Val Gln Leu Val Glu Ser Gly Gly Gly Leu Val Gln Pro Gly Gly
1               5                  10                 15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Gly Ile Lys Ser Ser Gly Asp Ser Thr Arg Tyr Ala Gly Ser Val
50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
            85                  90                  95

Ala Lys Ser Arg Val Ser Arg Thr Gly Leu Tyr Thr Tyr Asp Asn Arg
            100                 105                 110

Gly Gln Gly Thr Leu Val Thr Val Ser Ser Gly Gly Gly Gly Ser Gly
            115                 120                 125

Gly Gly Ser Gly Gly Gly Ser Gly Gly Gly Ser Glu Val
            130                 135                 140

Gln Leu Val Glu Ser Gly Gly Gly Leu Val Gln Pro Gly Gly Ser Leu
145                 150                 155                 160

Arg Leu Ser Cys Ala Ala Ser Gly Arg Thr Phe Asn Asn Tyr Ala Met
            165                 170                 175

Gly Trp Phe Arg Gln Ala Pro Gly Lys Glu Arg Glu Phe Val Ala Ala
            180                 185                 190

Ile Thr Arg Ser Gly Val Arg Ser Gly Val Ser Ala Ile Tyr Gly Asp
            195                 200                 205

Ser Val Lys Asp Arg Phe Thr Ile Ser Arg Asp Asn Ala Lys Asn Thr
            210                 215                 220

Leu Tyr Leu Gln Met Asn Ser Leu Arg Pro Glu Asp Thr Ala Val Tyr
225                 230                 235                 240
```

```
Tyr Cys Ala Ala Ser Ala Ile Gly Ser Gly Ala Leu Arg Arg Phe Glu
                245                 250                 255

Tyr Asp Tyr Ser Gly Gln Gly Thr Leu Val Thr Val Ser Ser Ala
            260                 265                 270

<210> SEQ ID NO 39
<211> LENGTH: 386
<212> TYPE: PRT
<213> ORGANISM: Artificial Sequence
<220> FEATURE:
<223> OTHER INFORMATION: Nanobody or Nanobody construct

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Pro Met Gly Trp Phe Arg Gln Ala Pro Gly Lys Gly Arg Glu Phe Val
        35                  40                  45

Ser Ser Ile Thr Gly Ser Gly Gly Ser Thr Tyr Tyr Ala Asp Ser Val
50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
            85                  90                  95

Ala Ala Tyr Ile Arg Pro Asp Thr Tyr Leu Ser Arg Asp Tyr Arg Lys
        100                 105                 110

Tyr Asp Tyr Trp Gly Gln Gly Thr Leu Val Thr Val Ser Ser Gly Gly
    115                 120                 125

Gly Gly Ser Gly Gly Gly Ser Glu Val Gln Leu Val Glu Ser Gly Gly
130                 135                 140

Gly Leu Val Gln Pro Gly Asn Ser Leu Arg Leu Ser Cys Ala Ala Ser
145                 150                 155                 160

Gly Phe Thr Phe Ser Ser Phe Gly Met Ser Trp Val Arg Gln Ala Pro
                165                 170                 175

Gly Lys Gly Leu Glu Trp Val Ser Ser Ile Ser Gly Ser Gly Ser Asp
            180                 185                 190

Thr Leu Tyr Ala Asp Ser Val Lys Gly Arg Phe Thr Ile Ser Arg Asp
        195                 200                 205

Asn Ala Lys Thr Thr Leu Tyr Leu Gln Met Asn Ser Leu Arg Pro Glu
    210                 215                 220

Asp Thr Ala Val Tyr Tyr Cys Thr Ile Gly Gly Ser Leu Ser Arg Ser
225                 230                 235                 240

Ser Gln Gly Thr Leu Val Thr Val Ser Ser Gly Gly Gly Gly Ser Gly
                245                 250                 255

Gly Gly Ser Glu Val Gln Leu Val Glu Ser Gly Gly Gly Leu Val Gln
            260                 265                 270

Pro Gly Gly Ser Leu Arg Leu Ser Cys Ala Ala Ser Gly Phe Thr Phe
        275                 280                 285

Ser Ser Tyr Pro Met Gly Trp Phe Arg Gln Ala Pro Gly Lys Gly Arg
    290                 295                 300

Glu Phe Val Ser Ser Ile Thr Gly Ser Gly Gly Ser Thr Tyr Tyr Ala
305                 310                 315                 320

Asp Ser Val Lys Gly Arg Phe Thr Ile Ser Arg Asp Asn Ala Lys Asn
                325                 330                 335
```

```
Thr Leu Tyr Leu Gln Met Asn Ser Leu Arg Pro Glu Asp Thr Ala Val
            340                 345                 350

Tyr Tyr Cys Ala Ala Tyr Ile Arg Pro Asp Thr Tyr Leu Ser Arg Asp
            355                 360                 365

Tyr Arg Lys Tyr Asp Tyr Trp Gly Gln Gly Thr Leu Val Thr Val Ser
370                 375                 380

Ser Ala
385

<210> SEQ ID NO 40
<211> LENGTH: 364
<212> TYPE: PRT
<213> ORGANISM: Artificial Sequence
<220> FEATURE:
<223> OTHER INFORMATION: Nanobody or Nanobody construct

<400> SEQUENCE: 40

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Tyr Trp Val Arg Gln Ala Pro Gly Lys Gly Leu Glu Trp Val
        35                  40                  45

Ser Glu Ile Asn Thr Asn Gly Leu Ile Thr Lys Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Arg Ser Pro Ser Gly Phe Asn Arg Gly Gln Gly Thr Leu Val Thr
            100                 105                 110

Val Ser Ser Gly Gly Gly Gly Ser Gly Gly Gly Ser Glu Val Gln Leu
        115                 120                 125

Val Glu Ser Gly Gly Gly Leu Val Gln Pro Gly Asn Ser Leu Arg Leu
    130                 135                 140

Ser Cys Ala Ala Ser Gly Phe Thr Phe Ser Ser Phe Gly Met Ser Trp
145                 150                 155                 160

Val Arg Gln Ala Pro Gly Lys Gly Leu Glu Trp Val Ser Ser Ile Ser
                165                 170                 175

Gly Ser Gly Ser Asp Thr Leu Tyr Ala Asp Ser Val Lys Gly Arg Phe
            180                 185                 190

Thr Ile Ser Arg Asp Asn Ala Lys Thr Thr Leu Tyr Leu Gln Met Asn
        195                 200                 205

Ser Leu Arg Pro Glu Asp Thr Ala Val Tyr Tyr Cys Thr Ile Gly Gly
    210                 215                 220

Ser Leu Ser Arg Ser Ser Gln Gly Thr Leu Val Thr Val Ser Ser Gly
225                 230                 235                 240

Gly Gly Gly Ser Gly Gly Gly Ser Glu Val Gln Leu Val Glu Ser Gly
                245                 250                 255

Gly Gly Leu Val Gln Pro Gly Gly Ser Leu Arg Leu Ser Cys Ala Ala
            260                 265                 270

Ser Gly Phe Thr Phe Ser Asp Tyr Trp Met Tyr Trp Val Arg Gln Ala
        275                 280                 285

Pro Gly Lys Gly Leu Glu Trp Val Ser Glu Ile Asn Thr Asn Gly Leu
    290                 295                 300
```

```
Ile Thr Lys Tyr Pro Asp Ser Val Lys Gly Arg Phe Thr Ile Ser Arg
305                 310                 315                 320

Asp Asn Ala Lys Asn Thr Leu Tyr Leu Gln Met Asn Ser Leu Arg Pro
            325                 330                 335

Glu Asp Thr Ala Val Tyr Tyr Cys Ala Arg Ser Pro Ser Gly Phe Asn
            340                 345                 350

Arg Gly Gln Gly Thr Leu Val Thr Val Ser Ser Ala
        355                 360
```

<210> SEQ ID NO 41
<211> LENGTH: 246
<212> TYPE: PRT
<213> ORGANISM: Artificial Sequence
<220> FEATURE:
<223> OTHER INFORMATION: Nanobody or Nanobody construct

<400> SEQUENCE: 41

```
Glu Val Gln Leu Val Glu Ser Gly Gly Leu Val Gln Pro Gly Gly
1               5                   10                  15

Ser Leu Arg Leu Ser Cys Ala Ala Ser Gly Ser Val Phe Lys Ile Asn
            20                  25                  30

Val Met Ala Trp Tyr Arg Gln Ala Pro Gly Lys Gly Arg Glu Leu Val
        35                  40                  45

Ala Gly Ile Ile Ser Gly Gly Ser Thr Ser Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Ile Thr Thr Glu Ser Asp Tyr Asp Leu Gly Arg Arg Tyr Trp Gly
            100                 105                 110

Gln Gly Thr Leu Val Thr Val Ser Ser Gly Gly Gly Gly Ser Gly Gly
        115                 120                 125

Gly Ser Glu Val Gln Leu Val Glu Ser Gly Gly Gly Leu Val Gln Pro
    130                 135                 140

Gly Asn Ser Leu Arg Leu Ser Cys Ala Ala Ser Gly Phe Thr Phe Ser
145                 150                 155                 160

Ser Phe Gly Met Ser Trp Val Arg Gln Ala Pro Gly Lys Gly Leu Glu
                165                 170                 175

Trp Val Ser Ser Ile Ser Gly Ser Gly Ser Asp Thr Leu Tyr Ala Asp
            180                 185                 190

Ser Val Lys Gly Arg Phe Thr Ile Ser Arg Asp Asn Ala Lys Thr Thr
        195                 200                 205

Leu Tyr Leu Gln Met Asn Ser Leu Arg Pro Glu Asp Thr Ala Val Tyr
    210                 215                 220

Tyr Cys Thr Ile Gly Gly Ser Leu Ser Arg Ser Ser Gln Gly Thr Leu
225                 230                 235                 240

Val Thr Val Ser Ser Ala
                245
```

<210> SEQ ID NO 42
<211> LENGTH: 260
<212> TYPE: PRT
<213> ORGANISM: Artificial Sequence
<220> FEATURE:
<223> OTHER INFORMATION: Nanobody or Nanobody construct

```
<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Tyr Asn
            20                  25                  30

Pro Met Gly Trp Phe Arg Gln Ala Pro Gly Lys Gly Arg Glu Leu Val
        35                  40                  45

Ala Ala Ile Ser Arg Thr Gly Gly Ser Thr Tyr Tyr Pro Asp Ser Val
    50                  55                  60

Glu Gly Arg Phe Thr Ile Ser Arg Asp Asn Ala Lys Arg Met Val Tyr
65                  70                  75                  80

Leu Gln Met Asn Ser Leu Arg Ala Glu Asp Thr Ala Val Tyr Tyr Cys
                85                  90                  95

Ala Ala Ala Gly Val Arg Ala Glu Asp Gly Arg Val Arg Thr Leu Pro
            100                 105                 110

Ser Glu Tyr Thr Phe Trp Gly Gln Gly Thr Gln Val Thr Val Ser Ser
        115                 120                 125

Ala Ala Ala Glu Val Gln Leu Val Glu Ser Gly Gly Gly Leu Val Gln
    130                 135                 140

Pro Gly Gly Ser Leu Arg Leu Ser Cys Ala Ala Ser Gly Arg Thr Phe
145                 150                 155                 160

Ser Tyr Asn Pro Met Gly Trp Phe Arg Gln Ala Pro Gly Lys Gly Arg
                165                 170                 175

Glu Leu Val Ala Ala Ile Ser Arg Thr Gly Gly Ser Thr Tyr Tyr Pro
            180                 185                 190

Asp Ser Val Glu Gly Arg Phe Thr Ile Ser Arg Asp Asn Ala Lys Arg
        195                 200                 205

Met Val Tyr Leu Gln Met Asn Ser Leu Arg Ala Glu Asp Thr Ala Val
    210                 215                 220

Tyr Tyr Cys Ala Ala Ala Gly Val Arg Ala Glu Asp Gly Arg Val Arg
225                 230                 235                 240

Thr Leu Pro Ser Glu Tyr Thr Phe Trp Gly Gln Gly Thr Gln Val Thr
                245                 250                 255

Val Ser Ser Ala
            260

<210> SEQ ID NO 43
<211> LENGTH: 250
<212> TYPE: PRT
<213> ORGANISM: Artificial Sequence
<220> FEATURE:
<223> OTHER INFORMATION: Nanobody or Nanobody construct

<400> SEQUENCE: 43

Asp Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Leu Asp Tyr Tyr
            20                  25                  30

Ala Ile Gly Trp Phe Arg Gln Ala Pro Gly Lys Glu Arg Glu Gly Val
        35                  40                  45

Leu Cys Ile Asp Ala Ser Asp Ile Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
```

```
                    85                  90                  95
Ala Thr Pro Ile Gly Leu Ser Ser Cys Leu Leu Glu Tyr Asp Tyr
            100                 105                 110

Asp Tyr Trp Gly Gln Gly Thr Leu Val Thr Val Ser Gly Gly Gly
        115                 120                 125

Gly Ser Gly Gly Gly Ser Glu Val Gln Leu Leu Glu Ser Gly Gly
    130                 135                 140

Leu Val Gln Pro Gly Gly Ser Leu Arg Leu Ser Cys Ala Ala Ser Gly
145                 150                 155                 160

Phe Thr Phe Arg Ser Phe Gly Met Ser Trp Val Arg Gln Ala Pro Gly
                165                 170                 175

Lys Gly Pro Glu Trp Val Ser Ser Ile Ser Gly Ser Gly Ser Asp Thr
            180                 185                 190

Leu Tyr Ala Asp Ser Val Lys Gly Arg Phe Thr Ile Ser Arg Asp Asn
        195                 200                 205

Ser Lys Asn Thr Leu Tyr Leu Gln Met Asn Ser Leu Arg Pro Glu Asp
    210                 215                 220

Thr Ala Val Tyr Tyr Cys Thr Ile Gly Gly Ser Leu Ser Arg Ser Ser
225                 230                 235                 240

Gln Gly Thr Leu Val Thr Val Ser Ser Ala
                245                 250

<210> SEQ ID NO 44
<211> LENGTH: 368
<212> TYPE: PRT
<213> ORGANISM: Artificial Sequence
<220> FEATURE:
<223> OTHER INFORMATION: Nanobody or Nanobody construct

<400> SEQUENCE: 44

Asp Val Gln Leu Val Glu Ser Gly Gly Gly Leu Val Gln Pro Gly Gly
1               5                   10                  15

Ser Leu Arg Leu Ser Cys Ala Ala Ser Arg Ser Ile Gly Arg Leu Asp
            20                  25                  30

Arg Met Gly Trp Tyr Arg His Arg Pro Gly Glu Pro Arg Glu Leu Val
        35                  40                  45

Ala Thr Ile Thr Gly Gly Ser Ser Ile Asn Tyr Gly Asp Ser Val Lys
    50                  55                  60

Gly Arg Phe Thr Ile Ser Ile Asp Asn Ser Lys Asn Thr Val Tyr Leu
65                  70                  75                  80

Gln Met Asn Ser Leu Arg Pro Glu Asp Thr Ala Val Tyr Tyr Cys Asn
                85                  90                  95

Phe Asn Lys Tyr Val Thr Ser Arg Asp Thr Trp Gly Gln Gly Thr Leu
            100                 105                 110

Val Thr Val Ser Ser Gly Gly Gly Gly Ser Gly Gly Gly Ser Glu Val
        115                 120                 125

Gln Leu Val Glu Ser Gly Gly Gly Leu Val Gln Pro Gly Asn Ser Leu
    130                 135                 140

Arg Leu Ser Cys Ala Ala Ser Gly Phe Thr Phe Ser Ser Phe Gly Met
145                 150                 155                 160

Ser Trp Val Arg Gln Ala Pro Gly Lys Gly Leu Glu Trp Val Ser Ser
                165                 170                 175

Ile Ser Gly Ser Gly Ser Asp Thr Leu Tyr Ala Asp Ser Val Lys Gly
            180                 185                 190

Arg Phe Thr Ile Ser Arg Asp Asn Ala Lys Thr Thr Leu Tyr Leu Gln
```

```
                195                 200                 205
Met Asn Ser Leu Arg Pro Glu Asp Thr Ala Val Tyr Tyr Cys Thr Ile
        210                 215                 220
Gly Gly Ser Leu Ser Arg Ser Ser Gln Gly Thr Leu Val Thr Val Ser
225                 230                 235                 240
Ser Gly Gly Gly Ser Gly Gly Gly Ser Glu Val Gln Leu Val Glu
                245                 250                 255
Ser Gly Gly Gly Leu Val Gln Pro Gly Gly Ser Leu Arg Leu Ser Cys
                260                 265                 270
Ala Ala Ser Arg Ser Ile Gly Arg Leu Asp Arg Met Gly Trp Tyr Arg
                275                 280                 285
His Arg Pro Gly Glu Pro Arg Glu Leu Val Ala Thr Ile Thr Gly Gly
        290                 295                 300
Ser Ser Ile Asn Tyr Gly Asp Ser Val Lys Gly Arg Phe Thr Ile Ser
305                 310                 315                 320
Ile Asp Asn Ser Lys Asn Thr Val Tyr Leu Gln Met Asn Ser Leu Arg
                325                 330                 335
Pro Glu Asp Thr Ala Val Tyr Tyr Cys Asn Phe Asn Lys Tyr Val Thr
                340                 345                 350
Ser Arg Asp Thr Trp Gly Gln Gly Thr Leu Val Thr Val Ser Ser Ala
        355                 360                 365

<210> SEQ ID NO 45
<211> LENGTH: 117
<212> TYPE: PRT
<213> ORGANISM: Artificial Sequence
<220> FEATURE:
<223> OTHER INFORMATION: Nanobody or Nanobody construct

<400> SEQUENCE: 45

Glu Val Gln Leu Val Glu Ser Gly Gly Gly Leu Val Gln Ala Gly Gly
1               5                   10                  15
Ser Leu Arg Leu Ser Cys Ala Ala Ser Arg Ser Ile Gly Arg Leu Asp
                20                  25                  30
Arg Met Gly Trp Tyr Arg His Arg Thr Gly Glu Pro Arg Glu Leu Val
        35                  40                  45
Ala Thr Ile Thr Gly Gly Ser Ser Ile Asn Tyr Gly Asp Phe Val Lys
    50                  55                  60
Gly Arg Phe Thr Ile Ser Ile Asp Asn Ala Lys Asn Thr Val Tyr Leu
65                  70                  75                  80
Gln Met Asn Asn Leu Lys Pro Glu Asp Thr Ala Val Tyr Tyr Cys Asn
                85                  90                  95
Phe Asn Lys Tyr Val Thr Ser Arg Asp Thr Trp Gly Gln Gly Thr Gln
                100                 105                 110
Val Thr Val Ser Ser
        115

<210> SEQ ID NO 46
<211> LENGTH: 143
<212> TYPE: PRT
<213> ORGANISM: Artificial Sequence
<220> FEATURE:
<223> OTHER INFORMATION: Nanobody or Nanobody construct

<400> SEQUENCE: 46

Glu Val Gln Leu Val Glu Ser Gly Gly Gly Leu Val Gln Ala Gly Gly
1               5                   10                  15
```

```
Ser Leu Arg Leu Ser Cys Ala Ala Ser Arg Ser Ile Gly Arg Leu Asp
            20                  25                  30

Arg Met Gly Trp Tyr Arg His Arg Thr Gly Glu Pro Arg Glu Leu Val
        35                  40                  45

Ala Thr Ile Thr Gly Gly Ser Ser Ile Asn Tyr Gly Asp Phe Val Lys
    50                  55                  60

Gly Arg Phe Thr Ile Ser Ile Asp Asn Ala Lys Asn Thr Val Tyr Leu
65              70                  75                  80

Gln Met Asn Asn Leu Lys Pro Glu Asp Thr Ala Val Tyr Tyr Cys Asn
                85                  90                  95

Phe Asn Lys Tyr Val Thr Ser Arg Asp Thr Trp Gly Gln Gly Thr Gln
            100                 105                 110

Val Thr Val Ser Ser Ala Ala Ala His His His His His His Gly Ala
        115                 120                 125

Ala Glu Gln Lys Leu Ile Ser Glu Glu Asp Leu Asn Gly Ala Ala
    130                 135                 140
```

<210> SEQ ID NO 47
<211> LENGTH: 146
<212> TYPE: PRT
<213> ORGANISM: Artificial Sequence
<220> FEATURE:
<223> OTHER INFORMATION: Nanobody or Nanobody construct

<400> SEQUENCE: 47

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Val Phe Lys Ile Asn
            20                  25                  30

Val Met Ala Trp Tyr Arg Gln Ala Pro Gly Lys Gly Arg Glu Leu Val
        35                  40                  45

Ala Gly Ile Ile Ser Gly Gly Ser Thr Ser Tyr Ala Asp Ser Val Lys
    50                  55                  60

Gly Arg Phe Thr Ile Ser Arg Asp Asn Ala Lys Asn Thr Leu Tyr Leu
65              70                  75                  80

Gln Met Asn Ser Leu Arg Pro Glu Asp Thr Ala Val Tyr Tyr Cys Ala
                85                  90                  95

Phe Ile Thr Thr Glu Ser Asp Tyr Asp Leu Gly Arg Arg Tyr Trp Gly
            100                 105                 110

Gln Gly Thr Leu Val Thr Val Ser Ser Gly Gly Gly Ser Gly Gly
            115                 120                 125

Gly Ser Arg Asp Trp Asp Phe Asp Val Phe Gly Gly Thr Pro Val
130                 135                 140

Gly Gly
145
```

<210> SEQ ID NO 48
<211> LENGTH: 151
<212> TYPE: PRT
<213> ORGANISM: Artificial Sequence
<220> FEATURE:
<223> OTHER INFORMATION: Nanobody or Nanobody construct

<400> SEQUENCE: 48

```
Glu Val Gln Leu Val Glu Ser Gly Gly Gly Leu Val Gln Pro Gly Gly
1               5                   10                  15

Ser Leu Arg Leu Ser Cys Ile Ala Ser Gly Leu Pro Phe Ser Thr Lys
            20                  25                  30
```

```
Ser Met Gly Trp Phe Arg Gln Ala Pro Gly Lys Glu Arg Glu Phe Val
        35                  40                  45

Ala Arg Ile Ser Pro Gly Gly Thr Ser Arg Tyr Tyr Gly Asp Phe Val
    50                  55                  60

Lys Gly Arg Phe Ala Ile Ser Arg Asp Asn Ala Lys Asn Thr Thr Trp
65                  70                  75                  80

Leu Gln Met Asn Ser Leu Lys Ala Glu Asp Thr Ala Val Tyr Tyr Cys
                85                  90                  95

Ala Ser Gly Glu Arg Ser Thr Tyr Ile Gly Ser Asn Tyr Tyr Arg Thr
                100                 105                 110

Asn Glu Tyr Asp Tyr Trp Gly Thr Gly Thr Gln Val Thr Val Ser Ser
                115                 120                 125

Ala Ala Ala Glu Gln Lys Leu Ile Ser Glu Glu Asp Leu Asn Gly Ala
            130                 135                 140

Ala His His His His His His
145                 150

<210> SEQ ID NO 49
<211> LENGTH: 151
<212> TYPE: PRT
<213> ORGANISM: Artificial Sequence
<220> FEATURE:
<223> OTHER INFORMATION: Nanobody or Nanobody construct

<400> SEQUENCE: 49

Glu Val Gln Leu Leu Glu Ser Gly Gly Gly Leu Val Gln Pro Gly Gly
1               5                   10                  15

Ser Leu Arg Leu Ser Cys Ala Ala Ser Gly Leu Pro Phe Ser Thr Lys
            20                  25                  30

Ser Met Gly Trp Phe Arg Gln Ala Pro Gly Lys Gly Arg Glu Phe Val
        35                  40                  45

Ser Arg Ile Ser Pro Gly Gly Thr Ser Arg Tyr Tyr Gly Asp Phe Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Gly Glu Arg Ser Thr Tyr Ile Gly Ser Asn Tyr Tyr Arg Thr
                100                 105                 110

Asn Glu Tyr Asp Tyr Trp Gly Gln Gly Thr Leu Val Thr Val Ser Ser
                115                 120                 125

Ala Ala Ala Glu Gln Lys Leu Ile Ser Glu Glu Asp Leu Asn Gly Ala
            130                 135                 140

Ala His His His His His His
145                 150

<210> SEQ ID NO 50
<211> LENGTH: 121
<212> TYPE: PRT
<213> ORGANISM: Artificial Sequence
<220> FEATURE:
<223> OTHER INFORMATION: Nanobody or Nanobody construct

<400> SEQUENCE: 50

His His His His His His Glu Val Gln Leu Val Glu Ser Gly Gly Gly
1               5                   10                  15

Ser Val Gln Pro Gly Asn Ser Leu Arg Leu Ser Cys Ala Ala Ser Gly
```

```
                    20                  25                  30
Phe Thr Phe Ser Ser Phe Gly Met Ser Trp Val Arg Gln Ala Pro Gly
            35                  40                  45
Lys Gly Leu Glu Trp Val Ser Ser Ile Ser Gly Ser Gly Ser Asp Thr
        50                  55                  60
Leu Tyr Ala Asp Ser Val Lys Gly Arg Phe Thr Ile Ser Arg Asp Asn
65                  70                  75                  80
Ala Lys Thr Thr Leu Tyr Leu Gln Met Asn Ser Leu Arg Pro Glu Asp
                85                  90                  95
Thr Ala Val Tyr Tyr Cys Thr Ile Gly Gly Ser Leu Ser Arg Ser Ser
            100                 105                 110
Gln Gly Thr Leu Val Thr Val Ser Ser
        115                 120
```

<210> SEQ ID NO 51
<211> LENGTH: 121
<212> TYPE: PRT
<213> ORGANISM: Artificial Sequence
<220> FEATURE:
<223> OTHER INFORMATION: Nanobody or Nanobody construct

<400> SEQUENCE: 51

```
His His His His His His Glu Val Gln Leu Val Glu Ser Gly Gly Gly
1               5                   10                  15
Leu Val Gln Pro Gly Asn Ser Leu Arg Leu Ser Cys Ala Ala Ser Gly
            20                  25                  30
Phe Thr Phe Ser Ser Phe Gly Met Ser Trp Val Arg Gln Ala Pro Gly
        35                  40                  45
Lys Gly Leu Glu Trp Val Ser Ser Ile Ser Gly Ser Gly Ser Asp Thr
    50                  55                  60
Leu Tyr Ala Asp Ser Val Lys Gly Arg Phe Thr Ile Ser Arg Asp Asn
65                  70                  75                  80
Ala Lys Thr Thr Leu Tyr Leu Gln Met Asn Ser Leu Arg Pro Glu Asp
                85                  90                  95
Thr Ala Val Tyr Tyr Cys Thr Ile Gly Gly Ser Leu Ser Arg Ser Ser
            100                 105                 110
Gln Gly Thr Leu Val Gln Val Ser Ser
        115                 120
```

<210> SEQ ID NO 52
<211> LENGTH: 121
<212> TYPE: PRT
<213> ORGANISM: Artificial Sequence
<220> FEATURE:
<223> OTHER INFORMATION: Nanobody or Nanobody construct

<400> SEQUENCE: 52

```
His His His His His His Glu Val Gln Leu Val Glu Ser Gly Gly Gly
1               5                   10                  15
Leu Val Gln Pro Gly Asn Ser Leu Arg Leu Ser Cys Ala Ala Ser Gly
            20                  25                  30
Phe Thr Phe Ser Ser Phe Gly Met Ser Trp Val Arg Gln Ala Pro Gly
        35                  40                  45
Lys Gly Leu Glu Trp Val Ser Ser Ile Ser Gly Ser Gly Ser Asp Thr
    50                  55                  60
Leu Tyr Ala Asp Ser Val Lys Gly Arg Phe Thr Ile Ser Arg Asp Asn
65                  70                  75                  80
```

```
Ala Lys Thr Thr Leu Tyr Leu Gln Met Asn Ser Leu Arg Pro Glu Asp
                85                  90                  95

Thr Ala Val Tyr Tyr Cys Thr Ile Gly Gly Ser Leu Ser Arg Ser Ser
            100                 105                 110

Gln Gly Thr Leu Val Thr Val Gly Ser
        115                 120

<210> SEQ ID NO 53
<211> LENGTH: 121
<212> TYPE: PRT
<213> ORGANISM: Artificial Sequence
<220> FEATURE:
<223> OTHER INFORMATION: Nanobody or Nanobody construct

<400> SEQUENCE: 53

His His His His His His Glu Val Gln Leu Val Glu Ser Gly Gly Gly
1               5                   10                  15

Leu Val Gln Pro Gly Asn Ser Leu Arg Leu Ser Cys Ala Ala Ser Gly
            20                  25                  30

Phe Thr Phe Ser Ser Phe Gly Met Ser Trp Val Arg Gln Ala Pro Gly
        35                  40                  45

Lys Gly Leu Glu Trp Val Ser Ile Ser Gly Ser Gly Ser Asp Thr
    50                  55                  60

Leu Tyr Ala Asp Ser Val Lys Gly Arg Phe Thr Ile Ser Arg Asp Asn
65                  70                  75                  80

Ala Lys Thr Thr Leu Tyr Leu Gln Met Asn Ser Leu Arg Pro Glu Asp
                85                  90                  95

Thr Ala Val Tyr Tyr Cys Thr Ile Gly Gly Ser Leu Ser Arg Ser Ser
            100                 105                 110

Gln Gly Thr Leu Val Thr Val Ser Gly
        115                 120

<210> SEQ ID NO 54
<211> LENGTH: 121
<212> TYPE: PRT
<213> ORGANISM: Artificial Sequence
<220> FEATURE:
<223> OTHER INFORMATION: Nanobody or Nanobody construct

<400> SEQUENCE: 54

His His His His His His Glu Val Gln Leu Val Glu Ser Gly Gly Gly
1               5                   10                  15

Ser Val Gln Pro Gly Asn Ser Leu Arg Leu Ser Cys Ala Ala Ser Gly
            20                  25                  30

Phe Thr Phe Ser Ser Phe Gly Met Ser Trp Val Arg Gln Ala Pro Gly
        35                  40                  45

Lys Gly Leu Glu Trp Val Ser Ser Ile Ser Gly Ser Gly Ser Asp Thr
    50                  55                  60

Leu Tyr Ala Asp Ser Val Lys Gly Arg Phe Thr Ile Ser Arg Asp Asn
65                  70                  75                  80

Ala Lys Thr Thr Leu Tyr Leu Gln Met Asn Ser Leu Arg Pro Glu Asp
                85                  90                  95

Thr Ala Val Tyr Tyr Cys Thr Ile Gly Gly Ser Leu Ser Arg Ser Ser
            100                 105                 110

Gln Gly Thr Leu Val Gln Val Gly Gly
        115                 120

<210> SEQ ID NO 55
```

```
<211> LENGTH: 122
<212> TYPE: PRT
<213> ORGANISM: Artificial Sequence
<220> FEATURE:
<223> OTHER INFORMATION: Nanobody or Nanobody construct

<400> SEQUENCE: 55
```

His His His His His His Glu Val Gln Leu Val Glu Ser Gly Gly Gly
1               5                   10                  15

Leu Val Gln Pro Gly Asn Ser Leu Arg Leu Ser Cys Ala Ala Ser Gly
            20                  25                  30

Phe Thr Phe Ser Ser Phe Gly Met Ser Trp Val Arg Gln Ala Pro Gly
        35                  40                  45

Lys Gly Leu Glu Trp Val Ser Ser Ile Ser Gly Ser Gly Ser Asp Thr
    50                  55                  60

Leu Tyr Ala Asp Ser Val Lys Gly Arg Phe Thr Ile Ser Arg Asp Asn
65                  70                  75                  80

Ala Lys Thr Thr Leu Tyr Leu Gln Met Asn Ser Leu Arg Pro Glu Asp
                85                  90                  95

Thr Ala Val Tyr Tyr Cys Thr Ile Gly Gly Ser Leu Ser Arg Ser Ser
            100                 105                 110

Gln Gly Thr Leu Val Thr Val Ser Ser Ala
        115                 120

```
<210> SEQ ID NO 56
<211> LENGTH: 123
<212> TYPE: PRT
<213> ORGANISM: Artificial Sequence
<220> FEATURE:
<223> OTHER INFORMATION: Nanobody or Nanobody construct

<400> SEQUENCE: 56
```

His His His His His His Glu Val Gln Leu Val Glu Ser Gly Gly Gly
1               5                   10                  15

Leu Val Gln Pro Gly Asn Ser Leu Arg Leu Ser Cys Ala Ala Ser Gly
            20                  25                  30

Phe Thr Phe Ser Ser Phe Gly Met Ser Trp Val Arg Gln Ala Pro Gly
        35                  40                  45

Lys Gly Leu Glu Trp Val Ser Ser Ile Ser Gly Ser Gly Ser Asp Thr
    50                  55                  60

Leu Tyr Ala Asp Ser Val Lys Gly Arg Phe Thr Ile Ser Arg Asp Asn
65                  70                  75                  80

Ala Lys Thr Thr Leu Tyr Leu Gln Met Asn Ser Leu Arg Pro Glu Asp
                85                  90                  95

Thr Ala Val Tyr Tyr Cys Thr Ile Gly Gly Ser Leu Ser Arg Ser Ser
            100                 105                 110

Gln Gly Thr Leu Val Thr Val Ser Ser Gly Gly
        115                 120

```
<210> SEQ ID NO 57
<211> LENGTH: 123
<212> TYPE: PRT
<213> ORGANISM: Artificial Sequence
<220> FEATURE:
<223> OTHER INFORMATION: Nanobody or Nanobody construct

<400> SEQUENCE: 57
```

His His His His His His Glu Val Gln Leu Val Glu Ser Gly Gly Gly
1               5                   10                  15

```
Leu Val Gln Pro Gly Asn Ser Leu Arg Leu Ser Cys Ala Ala Ser Gly
            20                  25                  30

Phe Thr Phe Ser Ser Phe Gly Met Ser Trp Val Arg Gln Ala Pro Gly
        35                  40                  45

Lys Gly Leu Glu Trp Val Ser Ser Ile Ser Gly Ser Gly Ser Asp Thr
    50                  55                  60

Leu Tyr Ala Asp Ser Val Lys Gly Arg Phe Thr Ile Ser Arg Asp Asn
65                  70                  75                  80

Ala Lys Thr Thr Leu Tyr Leu Gln Met Asn Ser Leu Arg Pro Glu Asp
                85                  90                  95

Thr Ala Val Tyr Tyr Cys Thr Ile Gly Gly Ser Leu Ser Arg Ser Ser
            100                 105                 110

Gln Gly Thr Leu Val Thr Val Ser Ser Ala Ser
        115                 120

<210> SEQ ID NO 58
<211> LENGTH: 124
<212> TYPE: PRT
<213> ORGANISM: Artificial Sequence
<220> FEATURE:
<223> OTHER INFORMATION: Nanobody or Nanobody construct

<400> SEQUENCE: 58

His His His His His His Glu Val Gln Leu Val Glu Ser Gly Gly Gly
1               5                   10                  15

Leu Val Gln Pro Gly Asn Ser Leu Arg Leu Ser Cys Ala Ala Ser Gly
            20                  25                  30

Phe Thr Phe Ser Ser Phe Gly Met Ser Trp Val Arg Gln Ala Pro Gly
        35                  40                  45

Lys Gly Leu Glu Trp Val Ser Ser Ile Ser Gly Ser Gly Ser Asp Thr
    50                  55                  60

Leu Tyr Ala Asp Ser Val Lys Gly Arg Phe Thr Ile Ser Arg Asp Asn
65                  70                  75                  80

Ala Lys Thr Thr Leu Tyr Leu Gln Met Asn Ser Leu Arg Pro Glu Asp
                85                  90                  95

Thr Ala Val Tyr Tyr Cys Thr Ile Gly Gly Ser Leu Ser Arg Ser Ser
            100                 105                 110

Gln Gly Thr Leu Val Thr Val Ser Ser Ala Ser Thr
        115                 120

<210> SEQ ID NO 59
<211> LENGTH: 125
<212> TYPE: PRT
<213> ORGANISM: Artificial Sequence
<220> FEATURE:
<223> OTHER INFORMATION: Nanobody or Nanobody construct

<400> SEQUENCE: 59

His His His His His His Glu Val Gln Leu Val Glu Ser Gly Gly Gly
1               5                   10                  15

Leu Val Gln Pro Gly Asn Ser Leu Arg Leu Ser Cys Ala Ala Ser Gly
            20                  25                  30

Phe Thr Phe Ser Ser Phe Gly Met Ser Trp Val Arg Gln Ala Pro Gly
        35                  40                  45

Lys Gly Leu Glu Trp Val Ser Ser Ile Ser Gly Ser Gly Ser Asp Thr
    50                  55                  60

Leu Tyr Ala Asp Ser Val Lys Gly Arg Phe Thr Ile Ser Arg Asp Asn
65                  70                  75                  80
```

```
Ala Lys Thr Thr Leu Tyr Leu Gln Met Asn Ser Leu Arg Pro Glu Asp
            85                  90                  95

Thr Ala Val Tyr Tyr Cys Thr Ile Gly Gly Ser Leu Ser Arg Ser Ser
            100                 105                 110

Gln Gly Thr Leu Val Thr Val Ser Ser Ala Ser Thr Lys
        115                 120                 125

<210> SEQ ID NO 60
<211> LENGTH: 124
<212> TYPE: PRT
<213> ORGANISM: Artificial Sequence
<220> FEATURE:
<223> OTHER INFORMATION: Nanobody or Nanobody construct

<400> SEQUENCE: 60

His His His His His His Glu Val Gln Leu Val Glu Ser Gly Gly Gly
1               5                   10                  15

Leu Val Gln Pro Gly Asn Ser Leu Arg Leu Ser Cys Ala Ala Ser Gly
            20                  25                  30

Phe Thr Phe Ser Ser Phe Gly Met Ser Trp Val Arg Gln Ala Pro Gly
            35                  40                  45

Lys Gly Leu Glu Trp Val Ser Ser Ile Ser Gly Ser Gly Ser Asp Thr
50                  55                  60

Leu Tyr Ala Asp Ser Val Lys Gly Arg Phe Thr Ile Ser Arg Asp Asn
65                  70                  75                  80

Ala Lys Thr Thr Leu Tyr Leu Gln Met Asn Ser Leu Arg Pro Glu Asp
            85                  90                  95

Thr Ala Val Tyr Tyr Cys Thr Ile Gly Gly Ser Leu Ser Arg Ser Ser
            100                 105                 110

Gln Gly Thr Leu Val Thr Val Ser Ser Ala Ser Pro
        115                 120

<210> SEQ ID NO 61
<211> LENGTH: 123
<212> TYPE: PRT
<213> ORGANISM: Artificial Sequence
<220> FEATURE:
<223> OTHER INFORMATION: Nanobody or Nanobody construct

<400> SEQUENCE: 61

His His His His His His Glu Val Gln Leu Val Glu Ser Gly Gly Gly
1               5                   10                  15

Leu Val Gln Pro Gly Asn Ser Leu Arg Leu Ser Cys Ala Ala Ser Gly
            20                  25                  30

Phe Thr Phe Ser Ser Phe Gly Met Ser Trp Val Arg Gln Ala Pro Gly
            35                  40                  45

Lys Gly Leu Glu Trp Val Ser Ser Ile Ser Gly Ser Gly Ser Asp Thr
50                  55                  60

Leu Tyr Ala Asp Ser Val Lys Gly Arg Phe Thr Ile Ser Arg Asp Asn
65                  70                  75                  80

Ala Lys Thr Thr Leu Tyr Leu Gln Met Asn Ser Leu Arg Pro Glu Asp
            85                  90                  95

Thr Ala Val Tyr Tyr Cys Thr Ile Gly Gly Ser Leu Ser Arg Ser Ser
            100                 105                 110

Gln Gly Thr Leu Val Thr Val Ser Ser Ala Pro
        115                 120
```

```
<210> SEQ ID NO 62
<211> LENGTH: 124
<212> TYPE: PRT
<213> ORGANISM: Artificial Sequence
<220> FEATURE:
<223> OTHER INFORMATION: Nanobody or Nanobody construct

<400> SEQUENCE: 62

His His His His His His Glu Val Gln Leu Val Glu Ser Gly Gly Gly
1               5                   10                  15

Leu Val Gln Pro Gly Asn Ser Leu Arg Leu Ser Cys Ala Ala Ser Gly
            20                  25                  30

Phe Thr Phe Ser Ser Phe Gly Met Ser Trp Val Arg Gln Ala Pro Gly
        35                  40                  45

Lys Gly Leu Glu Trp Val Ser Ser Ile Ser Gly Ser Gly Ser Asp Thr
    50                  55                  60

Leu Tyr Ala Asp Ser Val Lys Gly Arg Phe Thr Ile Ser Arg Asp Asn
65                  70                  75                  80

Ala Lys Thr Thr Leu Tyr Leu Gln Met Asn Ser Leu Arg Pro Glu Asp
                85                  90                  95

Thr Ala Val Tyr Tyr Cys Thr Ile Gly Gly Ser Leu Ser Arg Ser Ser
            100                 105                 110

Gln Gly Thr Leu Val Thr Val Ser Ser Ala Pro Thr
        115                 120

<210> SEQ ID NO 63
<211> LENGTH: 122
<212> TYPE: PRT
<213> ORGANISM: Artificial Sequence
<220> FEATURE:
<223> OTHER INFORMATION: Nanobody or Nanobody construct

<400> SEQUENCE: 63

His His His His His His Glu Val Gln Leu Val Glu Ser Gly Gly Gly
1               5                   10                  15

Leu Val Gln Pro Gly Asn Ser Leu Arg Leu Ser Cys Ala Ala Ser Gly
            20                  25                  30

Phe Thr Phe Ser Ser Phe Gly Met Ser Trp Val Arg Gln Ala Pro Gly
        35                  40                  45

Lys Gly Leu Glu Trp Val Ser Ser Ile Ser Gly Ser Gly Ser Asp Thr
    50                  55                  60

Leu Tyr Ala Asp Ser Val Lys Gly Arg Phe Thr Ile Ser Arg Asp Asn
65                  70                  75                  80

Ala Lys Thr Thr Leu Tyr Leu Gln Met Asn Ser Leu Arg Pro Glu Asp
                85                  90                  95

Thr Ala Val Tyr Tyr Cys Thr Ile Gly Gly Ser Leu Ser Arg Ser Ser
            100                 105                 110

Gln Gly Thr Leu Val Thr Val Ser Ser Trp
        115                 120

<210> SEQ ID NO 64
<211> LENGTH: 122
<212> TYPE: PRT
<213> ORGANISM: Artificial Sequence
<220> FEATURE:
<223> OTHER INFORMATION: Nanobody or Nanobody construct

<400> SEQUENCE: 64

His His His His His His Glu Val Gln Leu Val Glu Ser Gly Gly Gly
1               5                   10                  15
```

Leu Val Gln Pro Gly Asn Ser Leu Arg Leu Ser Cys Ala Ala Ser Gly
            20                  25                  30

Phe Thr Phe Ser Ser Phe Gly Met Ser Trp Val Arg Gln Ala Pro Gly
            35                  40                  45

Lys Gly Leu Glu Trp Val Ser Ile Ser Ser Gly Ser Asp Thr
50                  55                  60

Leu Tyr Ala Asp Ser Val Lys Gly Arg Phe Thr Ile Ser Arg Asp Asn
65                  70                  75                  80

Ala Lys Thr Thr Leu Tyr Leu Gln Met Asn Ser Leu Arg Pro Glu Asp
                85                  90                  95

Thr Ala Val Tyr Tyr Cys Thr Ile Gly Gly Ser Leu Ser Arg Ser Ser
                100                 105                 110

Gln Gly Thr Leu Val Thr Val Ser Ser Leu
            115                 120

<210> SEQ ID NO 65
<211> LENGTH: 123
<212> TYPE: PRT
<213> ORGANISM: Artificial Sequence
<220> FEATURE:
<223> OTHER INFORMATION: Nanobody or Nanobody construct

<400> SEQUENCE: 65

His His His His His His Glu Val Gln Leu Val Glu Ser Gly Gly Gly
1               5                   10                  15

Leu Val Gln Ala Gly Gly Ser Leu Arg Leu Ser Cys Ala Ala Ser Arg
            20                  25                  30

Ser Ile Gly Arg Leu Asp Arg Met Gly Trp Tyr Arg His Arg Pro Gly
            35                  40                  45

Glu Pro Arg Glu Leu Val Ala Thr Ile Thr Gly Ser Ser Ile Asn
        50                  55                  60

Tyr Gly Asp Ser Val Lys Gly Arg Phe Thr Ile Ser Ile Asp Asn Ser
65                  70                  75                  80

Lys Asn Thr Val Tyr Leu Gln Met Asn Ser Leu Arg Pro Glu Asp Thr
                85                  90                  95

Ala Val Tyr Tyr Cys Asn Phe Asn Lys Tyr Val Thr Ser Arg Asp Thr
                100                 105                 110

Trp Gly Gln Gly Thr Leu Val Thr Val Ser Ser
            115                 120

<210> SEQ ID NO 66
<211> LENGTH: 123
<212> TYPE: PRT
<213> ORGANISM: Artificial Sequence
<220> FEATURE:
<223> OTHER INFORMATION: Nanobody or Nanobody construct

<400> SEQUENCE: 66

His His His His His His Glu Val Gln Leu Val Glu Ser Gly Gly Gly
1               5                   10                  15

Ser Val Gln Pro Gly Gly Ser Leu Arg Leu Ser Cys Ala Ala Ser Arg
            20                  25                  30

Ser Ile Gly Arg Leu Asp Arg Met Gly Trp Tyr Arg His Arg Pro Gly
            35                  40                  45

Glu Pro Arg Glu Leu Val Ala Thr Ile Thr Gly Ser Ser Ile Asn
        50                  55                  60

Tyr Gly Asp Ser Val Lys Gly Arg Phe Thr Ile Ser Ile Asp Asn Ser

```
                65                  70                  75                  80
Lys Asn Thr Val Tyr Leu Gln Met Asn Ser Leu Arg Pro Glu Asp Thr
                    85                  90                  95

Ala Val Tyr Tyr Cys Asn Phe Asn Lys Tyr Val Thr Ser Arg Asp Thr
                100                 105                 110

Trp Gly Gln Gly Thr Leu Val Thr Val Ser Ser
            115                 120

<210> SEQ ID NO 67
<211> LENGTH: 123
<212> TYPE: PRT
<213> ORGANISM: Artificial Sequence
<220> FEATURE:
<223> OTHER INFORMATION: Nanobody or Nanobody construct

<400> SEQUENCE: 67

His His His His His His Glu Val Gln Leu Val Glu Ser Gly Gly Gly
1               5                   10                  15

Leu Val Gln Pro Gly Gly Ser Leu Arg Leu Ser Cys Ala Ala Ser Arg
            20                  25                  30

Ser Ile Gly Arg Leu Asp Arg Met Gly Trp Tyr Arg His Arg Pro Gly
        35                  40                  45

Glu Pro Arg Glu Leu Val Ala Thr Ile Thr Gly Gly Ser Ser Ile Asn
    50                  55                  60

Tyr Gly Asp Ser Val Lys Gly Arg Phe Thr Ile Ser Ile Asp Asn Ser
65                  70                  75                  80

Lys Asn Thr Val Tyr Leu Gln Met Asn Ser Leu Lys Pro Glu Asp Thr
                85                  90                  95

Ala Val Tyr Tyr Cys Asn Phe Asn Lys Tyr Val Thr Ser Arg Asp Thr
                100                 105                 110

Trp Gly Gln Gly Thr Leu Val Thr Val Ser Ser
            115                 120

<210> SEQ ID NO 68
<211> LENGTH: 123
<212> TYPE: PRT
<213> ORGANISM: Artificial Sequence
<220> FEATURE:
<223> OTHER INFORMATION: Nanobody or Nanobody construct

<400> SEQUENCE: 68

His His His His His His Glu Val Gln Leu Val Glu Ser Gly Gly Gly
1               5                   10                  15

Leu Val Gln Ala Gly Gly Ser Leu Arg Leu Ser Cys Ala Ala Ser Arg
            20                  25                  30

Ser Ile Gly Arg Leu Asp Arg Met Gly Trp Tyr Arg His Arg Pro Gly
        35                  40                  45

Glu Pro Arg Glu Leu Val Ala Thr Ile Thr Gly Gly Ser Ser Ile Asn
    50                  55                  60

Tyr Gly Asp Ser Val Lys Gly Arg Phe Thr Ile Ser Ile Asp Asn Ser
65                  70                  75                  80

Lys Asn Thr Val Tyr Leu Gln Met Asn Ser Leu Arg Pro Glu Asp Thr
                85                  90                  95

Ala Val Tyr Tyr Cys Asn Phe Asn Lys Tyr Val Thr Ser Arg Asp Thr
                100                 105                 110

Trp Gly Gln Gly Thr Gln Val Thr Val Ser Ser
            115                 120
```

```
<210> SEQ ID NO 69
<211> LENGTH: 123
<212> TYPE: PRT
<213> ORGANISM: Artificial Sequence
<220> FEATURE:
<223> OTHER INFORMATION: Nanobody or Nanobody construct

<400> SEQUENCE: 69

His His His His His His Glu Val Gln Leu Val Glu Ser Gly Gly Gly
1               5                   10                  15

Leu Val Gln Pro Gly Gly Ser Leu Arg Leu Ser Cys Ala Ala Ser Arg
            20                  25                  30

Ser Ile Gly Arg Leu Asp Arg Met Gly Trp Tyr Arg His Arg Pro Gly
        35                  40                  45

Glu Pro Arg Glu Leu Val Ala Thr Ile Thr Gly Gly Ser Ser Ile Asn
    50                  55                  60

Tyr Gly Asp Ser Val Lys Gly Arg Phe Thr Ile Ser Ile Asp Asn Ser
65                  70                  75                  80

Lys Asn Thr Val Tyr Leu Gln Met Asn Ser Leu Arg Pro Glu Asp Thr
                85                  90                  95

Ala Val Tyr Tyr Cys Asn Phe Asn Lys Tyr Val Thr Ser Arg Asp Thr
            100                 105                 110

Trp Gly Gln Gly Thr Gln Val Thr Val Ser Ser
        115                 120

<210> SEQ ID NO 70
<211> LENGTH: 123
<212> TYPE: PRT
<213> ORGANISM: Artificial Sequence
<220> FEATURE:
<223> OTHER INFORMATION: Nanobody or Nanobody construct

<400> SEQUENCE: 70

His His His His His His Glu Val Gln Leu Val Glu Ser Gly Gly Gly
1               5                   10                  15

Leu Val Gln Pro Gly Gly Ser Leu Arg Leu Ser Cys Ala Ala Ser Arg
            20                  25                  30

Ser Ile Gly Arg Leu Asp Arg Met Gly Trp Tyr Arg His Arg Pro Gly
        35                  40                  45

Glu Pro Arg Glu Leu Val Ala Thr Ile Thr Gly Gly Ser Ser Ile Asn
    50                  55                  60

Tyr Gly Asp Ser Val Lys Gly Arg Phe Thr Ile Ser Ile Asp Asn Ser
65                  70                  75                  80

Lys Asn Thr Val Tyr Leu Gln Met Asn Ser Leu Arg Pro Glu Asp Thr
                85                  90                  95

Ala Val Tyr Tyr Cys Asn Phe Asn Lys Tyr Val Thr Ser Arg Asp Thr
            100                 105                 110

Trp Gly Gln Gly Thr Leu Val Gln Val Ser Ser
        115                 120

<210> SEQ ID NO 71
<211> LENGTH: 123
<212> TYPE: PRT
<213> ORGANISM: Artificial Sequence
<220> FEATURE:
<223> OTHER INFORMATION: Nanobody or Nanobody construct

<400> SEQUENCE: 71

His His His His His His Glu Val Gln Leu Val Glu Ser Gly Gly Gly
```

```
            1               5                  10                 15
          Leu Val Gln Pro Gly Gly Ser Leu Arg Leu Ser Cys Ala Ala Ser Arg
                          20                  25                 30

Ser Ile Gly Arg Leu Asp Arg Met Gly Trp Tyr Arg His Arg Pro Gly
                          35                  40                 45

Glu Pro Arg Glu Leu Val Ala Thr Ile Thr Gly Gly Ser Ser Ile Asn
                          50                  55                 60

Tyr Gly Asp Ser Val Lys Gly Arg Phe Thr Ile Ser Ile Asp Asn Ser
           65                  70                  75                 80

Lys Asn Thr Val Tyr Leu Gln Met Asn Ser Leu Arg Pro Glu Asp Thr
                          85                  90                 95

Ala Val Tyr Tyr Cys Asn Phe Asn Lys Tyr Val Thr Ser Arg Asp Thr
                          100                 105                110

Trp Gly Gln Gly Thr Leu Val Thr Val Ser Gly
                          115                 120

<210> SEQ ID NO 72
<211> LENGTH: 123
<212> TYPE: PRT
<213> ORGANISM: Artificial Sequence
<220> FEATURE:
<223> OTHER INFORMATION: Nanobody or Nanobody construct

<400> SEQUENCE: 72

His His His His His His Glu Val Gln Leu Val Glu Ser Gly Gly Gly
           1               5                  10                 15

Leu Val Gln Pro Gly Gly Ser Leu Arg Leu Ser Cys Ala Ala Ser Arg
                          20                  25                 30

Ser Ile Gly Arg Leu Asp Arg Met Gly Trp Tyr Arg His Arg Pro Gly
                          35                  40                 45

Glu Pro Arg Glu Leu Val Ala Thr Ile Thr Gly Gly Ser Ser Ile Asn
                          50                  55                 60

Tyr Gly Asp Ser Val Lys Gly Arg Phe Thr Ile Ser Ile Asp Asn Ser
           65                  70                  75                 80

Lys Asn Thr Val Tyr Leu Gln Met Asn Ser Leu Arg Pro Glu Asp Thr
                          85                  90                 95

Ala Val Tyr Tyr Cys Asn Phe Asn Lys Tyr Val Thr Ser Arg Asp Thr
                          100                 105                110

Trp Gly Gln Gly Thr Leu Val Thr Val Gly Gly
                          115                 120

<210> SEQ ID NO 73
<211> LENGTH: 124
<212> TYPE: PRT
<213> ORGANISM: Artificial Sequence
<220> FEATURE:
<223> OTHER INFORMATION: Nanobody or Nanobody construct

<400> SEQUENCE: 73

His His His His His His Glu Val Gln Leu Val Glu Ser Gly Gly Gly
           1               5                  10                 15

Leu Val Gln Pro Gly Gly Ser Leu Arg Leu Ser Cys Ala Ala Ser Arg
                          20                  25                 30

Ser Ile Gly Arg Leu Asp Arg Met Gly Trp Tyr Arg His Arg Pro Gly
                          35                  40                 45

Glu Pro Arg Glu Leu Val Ala Thr Ile Thr Gly Gly Ser Ser Ile Asn
                          50                  55                 60
```

```
Tyr Gly Asp Ser Val Lys Gly Arg Phe Thr Ile Ser Ile Asp Asn Ser
65                  70                  75                  80

Lys Asn Thr Val Tyr Leu Gln Met Asn Ser Leu Arg Pro Glu Asp Thr
                85                  90                  95

Ala Val Tyr Tyr Cys Asn Phe Asn Lys Tyr Val Thr Ser Arg Asp Thr
            100                 105                 110

Trp Gly Gln Gly Thr Leu Val Thr Val Gly Gly
            115                 120
```

<210> SEQ ID NO 74
<211> LENGTH: 124
<212> TYPE: PRT
<213> ORGANISM: Artificial Sequence
<220> FEATURE:
<223> OTHER INFORMATION: Nanobody or Nanobody construct

<400> SEQUENCE: 74

```
His His His His His His Glu Val Gln Leu Val Glu Ser Gly Gly Gly
1               5                   10                  15

Leu Val Gln Pro Gly Gly Ser Leu Arg Leu Ser Cys Ala Ala Ser Arg
                20                  25                  30

Ser Ile Gly Arg Leu Asp Arg Met Gly Trp Tyr Arg His Arg Pro Gly
            35                  40                  45

Glu Pro Arg Glu Leu Val Ala Thr Ile Thr Gly Gly Ser Ser Ile Asn
        50                  55                  60

Tyr Gly Asp Ser Val Lys Gly Arg Phe Thr Ile Ser Ile Asp Asn Ser
65                  70                  75                  80

Lys Asn Thr Val Tyr Leu Gln Met Asn Ser Leu Arg Pro Glu Asp Thr
                85                  90                  95

Ala Val Tyr Tyr Cys Asn Phe Asn Lys Tyr Val Thr Ser Arg Asp Thr
            100                 105                 110

Trp Gly Gln Gly Thr Leu Val Thr Val Ser Ser Gly
            115                 120
```

<210> SEQ ID NO 75
<211> LENGTH: 125
<212> TYPE: PRT
<213> ORGANISM: Artificial Sequence
<220> FEATURE:
<223> OTHER INFORMATION: Nanobody or Nanobody construct

<400> SEQUENCE: 75

```
His His His His His His Glu Val Gln Leu Val Glu Ser Gly Gly Gly
1               5                   10                  15

Leu Val Gln Pro Gly Gly Ser Leu Arg Leu Ser Cys Ala Ala Ser Arg
                20                  25                  30

Ser Ile Gly Arg Leu Asp Arg Met Gly Trp Tyr Arg His Arg Pro Gly
            35                  40                  45

Glu Pro Arg Glu Leu Val Ala Thr Ile Thr Gly Gly Ser Ser Ile Asn
        50                  55                  60

Tyr Gly Asp Ser Val Lys Gly Arg Phe Thr Ile Ser Ile Asp Asn Ser
65                  70                  75                  80

Lys Asn Thr Val Tyr Leu Gln Met Asn Ser Leu Arg Pro Glu Asp Thr
                85                  90                  95

Ala Val Tyr Tyr Cys Asn Phe Asn Lys Tyr Val Thr Ser Arg Asp Thr
            100                 105                 110

Trp Gly Gln Gly Thr Leu Val Thr Val Ser Ser Ala Ala
            115                 120                 125
```

<210> SEQ ID NO 76
<211> LENGTH: 126
<212> TYPE: PRT
<213> ORGANISM: Artificial Sequence
<220> FEATURE:
<223> OTHER INFORMATION: Nanobody or Nanobody construct

<400> SEQUENCE: 76

```
His His His His His His Glu Val Gln Leu Val Glu Ser Gly Gly Gly
1               5                   10                  15

Leu Val Gln Pro Gly Gly Ser Leu Arg Leu Ser Cys Ala Ala Ser Arg
            20                  25                  30

Ser Ile Gly Arg Leu Asp Arg Met Gly Trp Tyr Arg His Arg Pro Gly
        35                  40                  45

Glu Pro Arg Glu Leu Val Ala Thr Ile Thr Gly Gly Ser Ser Ile Asn
    50                  55                  60

Tyr Gly Asp Ser Val Lys Gly Arg Phe Thr Ile Ser Ile Asp Asn Ser
65                  70                  75                  80

Lys Asn Thr Val Tyr Leu Gln Met Asn Ser Leu Arg Pro Glu Asp Thr
                85                  90                  95

Ala Val Tyr Tyr Cys Asn Phe Asn Lys Tyr Val Thr Ser Arg Asp Thr
            100                 105                 110

Trp Gly Gln Gly Thr Leu Val Thr Val Ser Ser Gly Gly Gly
        115                 120                 125
```

<210> SEQ ID NO 77
<211> LENGTH: 124
<212> TYPE: PRT
<213> ORGANISM: Artificial Sequence
<220> FEATURE:
<223> OTHER INFORMATION: Nanobody or Nanobody construct

<400> SEQUENCE: 77

```
His His His His His His Glu Val Gln Leu Val Glu Ser Gly Gly Gly
1               5                   10                  15

Leu Val Gln Pro Gly Gly Ser Leu Arg Leu Ser Cys Ala Ala Ser Arg
            20                  25                  30

Ser Ile Gly Arg Leu Asp Arg Met Gly Trp Tyr Arg His Arg Pro Gly
        35                  40                  45

Glu Pro Arg Glu Leu Val Ala Thr Ile Thr Gly Gly Ser Ser Ile Asn
    50                  55                  60

Tyr Gly Asp Ser Val Lys Gly Arg Phe Thr Ile Ser Ile Asp Asn Ser
65                  70                  75                  80

Lys Asn Thr Val Tyr Leu Gln Met Asn Ser Leu Arg Pro Glu Asp Thr
                85                  90                  95

Ala Val Tyr Tyr Cys Asn Phe Asn Lys Tyr Val Thr Ser Arg Asp Thr
            100                 105                 110

Trp Gly Gln Gly Thr Leu Val Thr Val Ser Ser Ala
        115                 120
```

<210> SEQ ID NO 78
<211> LENGTH: 123
<212> TYPE: PRT
<213> ORGANISM: Artificial Sequence
<220> FEATURE:
<223> OTHER INFORMATION: Nanobody or Nanobody construct

<400> SEQUENCE: 78

His His His His His Glu Val Gln Leu Val Glu Ser Gly Gly Gly
1               5                   10                  15

Leu Val Arg Pro Gly Gly Ser Leu Arg Leu Ser Cys Ala Ala Ser Arg
            20                  25                  30

Ser Ile Gly Arg Leu Asp Arg Met Gly Trp Tyr Arg His Arg Pro Gly
        35                  40                  45

Glu Pro Arg Glu Leu Val Ala Thr Ile Thr Gly Gly Ser Ser Ile Asn
50                  55                  60

Tyr Gly Asp Ser Val Lys Gly Arg Phe Thr Ile Ser Ile Asp Asn Ser
65                  70                  75                  80

Lys Asn Thr Val Tyr Leu Gln Met Asn Ser Leu Arg Pro Glu Asp Thr
                85                  90                  95

Ala Val Tyr Tyr Cys Asn Phe Asn Lys Tyr Val Thr Ser Arg Asp Thr
            100                 105                 110

Trp Gly Gln Gly Thr Leu Val Thr Val Ser Ser
            115                 120

<210> SEQ ID NO 79
<211> LENGTH: 124
<212> TYPE: PRT
<213> ORGANISM: Artificial Sequence
<220> FEATURE:
<223> OTHER INFORMATION: Nanobody or Nanobody construct

<400> SEQUENCE: 79

His His His His His Glu Val Gln Leu Val Glu Ser Gly Gly Gly Leu
1               5                   10                  15

Val Gln Pro Gly Gly Ser Leu Arg Leu Ser Cys Ala Ala Ser Arg Ser
            20                  25                  30

Ile Gly Arg Leu Asp Arg Met Gly Trp Tyr Arg His Arg Pro Gly Glu
        35                  40                  45

Pro Arg Glu Leu Val Ala Thr Ile Thr Gly Gly Ser Ser Ile Asn Tyr
50                  55                  60

Gly Asp Ser Val Lys Gly Arg Phe Thr Ile Ser Ile Asp Asn Ser Lys
65                  70                  75                  80

Asn Thr Val Tyr Leu Gln Met Asn Ser Leu Arg Pro Glu Asp Thr Ala
                85                  90                  95

Val Tyr Tyr Cys Asn Phe Asn Lys Tyr Val Thr Ser Arg Asp Thr Trp
            100                 105                 110

Gly Gln Gly Thr Leu Val Thr Val Ser Ser Gly Gly
            115                 120

<210> SEQ ID NO 80
<211> LENGTH: 123
<212> TYPE: PRT
<213> ORGANISM: Artificial Sequence
<220> FEATURE:
<223> OTHER INFORMATION: Nanobody or Nanobody construct

<400> SEQUENCE: 80

His His His His His His Glu Val Gln Leu Val Glu Ser Gly Gly Gly
1               5                   10                  15

Leu Val Gln Pro Gly Gly Ser Leu Arg Leu Ser Cys Ala Ala Ser Arg
            20                  25                  30

Ser Ile Gly Arg Leu Asp Arg Met Gly Trp Tyr Arg His Arg Pro Gly
        35                  40                  45

Glu Pro Arg Glu Leu Val Ala Thr Ile Thr Gly Gly Ser Ser Ile Asn
50                  55                  60

Tyr Gly Asp Ser Val Lys Gly Arg Phe Thr Ile Ser Ile Asp Asn Ser
65                  70                  75                  80

Lys Asn Thr Val Tyr Leu Gln Met Asn Ser Leu Arg Pro Glu Asp Thr
                85                  90                  95

Ala Val Tyr Tyr Cys Asn Phe Asn Lys Tyr Val Thr Ser Arg Asp Thr
            100                 105                 110

Trp Gly Gln Gly Thr Leu Val Gln Val Gly Gly
        115                 120

<210> SEQ ID NO 81
<211> LENGTH: 123
<212> TYPE: PRT
<213> ORGANISM: Artificial Sequence
<220> FEATURE:
<223> OTHER INFORMATION: Nanobody or Nanobody construct

<400> SEQUENCE: 81

His His His His His His Glu Val Gln Leu Val Glu Ser Gly Gly Gly
1               5                   10                  15

Val Val Gln Pro Gly Gly Ser Leu Arg Leu Ser Cys Ala Ala Ser Arg
            20                  25                  30

Ser Ile Gly Arg Leu Asp Arg Met Gly Trp Tyr Arg His Arg Pro Gly
        35                  40                  45

Glu Pro Arg Glu Leu Val Ala Thr Ile Thr Gly Ser Ser Ile Asn
    50                  55                  60

Tyr Gly Asp Ser Val Lys Gly Arg Phe Thr Ile Ser Ile Asp Asn Ser
65                  70                  75                  80

Lys Asn Thr Val Tyr Leu Gln Met Asn Ser Leu Arg Pro Glu Asp Thr
                85                  90                  95

Ala Val Tyr Tyr Cys Asn Phe Asn Lys Tyr Val Thr Ser Arg Asp Thr
            100                 105                 110

Trp Gly Gln Gly Thr Leu Val Thr Val Ser Ser
        115                 120

<210> SEQ ID NO 82
<211> LENGTH: 123
<212> TYPE: PRT
<213> ORGANISM: Artificial Sequence
<220> FEATURE:
<223> OTHER INFORMATION: Nanobody or Nanobody construct

<400> SEQUENCE: 82

His His His His His His Glu Val Gln Leu Val Glu Ser Gly Gly Gly
1               5                   10                  15

Leu Val Gln Pro Gly Gly Ser Leu Arg Leu Ser Cys Ala Ala Ser Arg
            20                  25                  30

Ser Ile Gly Arg Leu Asp Arg Met Gly Trp Tyr Arg His Arg Pro Gly
        35                  40                  45

Glu Pro Arg Glu Leu Val Ala Thr Ile Thr Gly Ser Ser Ile Asn
    50                  55                  60

Tyr Gly Asp Ser Val Lys Gly Arg Phe Thr Ile Ser Ile Asp Asn Ser
65                  70                  75                  80

Lys Asn Thr Val Tyr Leu Gln Met Asn Ser Leu Arg Ala Glu Asp Thr
                85                  90                  95

Ala Val Tyr Tyr Cys Asn Phe Asn Lys Tyr Val Thr Ser Arg Asp Thr
            100                 105                 110

Trp Gly Gln Gly Thr Leu Val Thr Val Ser Ser

-continued

```
            115                 120

<210> SEQ ID NO 83
<211> LENGTH: 123
<212> TYPE: PRT
<213> ORGANISM: Artificial Sequence
<220> FEATURE:
<223> OTHER INFORMATION: Nanobody or Nanobody construct

<400> SEQUENCE: 83

His His His His His His Glu Val Gln Leu Val Glu Ser Gly Gly Gly
1               5                   10                  15

Leu Val Gln Pro Gly Gly Ser Leu Arg Leu Ser Cys Ala Ala Ser Arg
            20                  25                  30

Ser Ile Gly Arg Leu Asp Arg Met Gly Trp Tyr Arg His Arg Pro Gly
        35                  40                  45

Glu Pro Arg Glu Leu Val Ala Thr Ile Thr Gly Gly Ser Ser Ile Asn
    50                  55                  60

Tyr Gly Asp Ser Val Lys Gly Arg Phe Thr Ile Ser Ile Asp Asn Ser
65                  70                  75                  80

Lys Asn Thr Val Tyr Leu Gln Met Asn Ser Leu Arg Pro Glu Asp Ala
                85                  90                  95

Ala Val Tyr Tyr Cys Asn Phe Asn Lys Tyr Val Thr Ser Arg Asp Thr
            100                 105                 110

Trp Gly Gln Gly Thr Leu Val Thr Val Ser Ser
        115                 120

<210> SEQ ID NO 84
<211> LENGTH: 123
<212> TYPE: PRT
<213> ORGANISM: Artificial Sequence
<220> FEATURE:
<223> OTHER INFORMATION: Nanobody or Nanobody construct

<400> SEQUENCE: 84

His His His His His His Glu Val Gln Leu Val Glu Ser Gly Gly Gly
1               5                   10                  15

Leu Val Gln Pro Gly Gly Ser Leu Arg Leu Ser Cys Ala Ala Ser Arg
            20                  25                  30

Ser Ile Gly Arg Leu Asp Arg Met Gly Trp Tyr Arg His Arg Pro Gly
        35                  40                  45

Glu Pro Arg Glu Leu Val Ala Thr Ile Thr Gly Gly Ser Ser Ile Asn
    50                  55                  60

Tyr Gly Asp Ser Val Lys Gly Arg Phe Thr Ile Ser Ile Asp Asn Ser
65                  70                  75                  80

Lys Asn Thr Val Tyr Leu Gln Met Asn Ser Leu Arg Pro Glu Asp Thr
                85                  90                  95

Ala Val Tyr Tyr Cys Asn Phe Asn Lys Tyr Val Thr Ser Arg Asp Thr
            100                 105                 110

Trp Gly Gln Gly Thr Leu Val Thr Val Gly Ser
        115                 120

<210> SEQ ID NO 85
<211> LENGTH: 123
<212> TYPE: PRT
<213> ORGANISM: Artificial Sequence
<220> FEATURE:
<223> OTHER INFORMATION: Nanobody or Nanobody construct

<400> SEQUENCE: 85
```

His His His His His His Glu Val Gln Leu Val Glu Ser Gly Gly Gly
1               5                   10                  15

Ser Val Gln Pro Gly Gly Ser Leu Arg Leu Ser Cys Ala Ala Ser Arg
            20                  25                  30

Ser Ile Gly Arg Leu Asp Arg Met Gly Trp Tyr Arg His Arg Pro Gly
        35                  40                  45

Glu Pro Arg Glu Leu Val Ala Thr Ile Thr Gly Gly Ser Ser Ile Asn
    50                  55                  60

Tyr Gly Asp Ser Val Lys Gly Arg Phe Thr Ile Ser Ile Asp Asn Ser
65                  70                  75                  80

Lys Asn Thr Val Tyr Leu Gln Met Asn Ser Leu Arg Pro Glu Asp Thr
                85                  90                  95

Ala Val Tyr Tyr Cys Asn Phe Asn Lys Tyr Val Thr Ser Arg Asp Thr
            100                 105                 110

Trp Gly Gln Gly Thr Leu Val Gln Val Gly Gly
            115                 120

<210> SEQ ID NO 86
<211> LENGTH: 123
<212> TYPE: PRT
<213> ORGANISM: Artificial Sequence
<220> FEATURE:
<223> OTHER INFORMATION: Nanobody or Nanobody construct

<400> SEQUENCE: 86

His His His His His His Glu Val Gln Leu Val Glu Ser Gly Gly Gly
1               5                   10                  15

Ser Val Gln Pro Gly Gly Ser Leu Arg Leu Ser Cys Ala Ala Ser Arg
            20                  25                  30

Ser Ile Gly Arg Leu Asp Arg Met Gly Trp Tyr Arg His Arg Pro Gly
        35                  40                  45

Glu Pro Arg Glu Leu Val Ala Thr Ile Thr Gly Gly Ser Ser Ile Asn
    50                  55                  60

Tyr Gly Asp Ser Val Lys Gly Arg Phe Thr Ile Ser Ile Asp Asn Ser
65                  70                  75                  80

Lys Asn Thr Val Tyr Leu Gln Met Asn Ser Leu Arg Pro Glu Asp Thr
                85                  90                  95

Ala Val Tyr Tyr Cys Asn Phe Asn Lys Tyr Val Thr Ser Arg Asp Thr
            100                 105                 110

Trp Gly Gln Gly Thr Leu Val Gln Val Ser Ser
            115                 120

<210> SEQ ID NO 87
<211> LENGTH: 123
<212> TYPE: PRT
<213> ORGANISM: Artificial Sequence
<220> FEATURE:
<223> OTHER INFORMATION: Nanobody or Nanobody construct

<400> SEQUENCE: 87

His His His His His His Glu Val Gln Leu Val Glu Ser Gly Gly Gly
1               5                   10                  15

Ser Val Gln Pro Gly Gly Ser Leu Arg Leu Ser Cys Ala Ala Ser Arg
            20                  25                  30

Ser Ile Gly Arg Leu Asp Arg Met Gly Trp Tyr Arg His Arg Pro Gly
        35                  40                  45

Glu Pro Arg Glu Leu Val Ala Thr Ile Thr Gly Gly Ser Ser Ile Asn

```
            50                  55                  60

Tyr Gly Asp Ser Val Lys Gly Arg Phe Thr Ile Ser Ile Asp Asn Ser
 65                  70                  75                  80

Lys Asn Thr Val Tyr Leu Gln Met Asn Ser Leu Arg Pro Glu Asp Thr
                 85                  90                  95

Ala Val Tyr Tyr Cys Asn Phe Asn Lys Tyr Val Thr Ser Arg Asp Thr
                100                 105                 110

Trp Gly Gln Gly Thr Leu Val Thr Val Gly Gly
            115                 120

<210> SEQ ID NO 88
<211> LENGTH: 124
<212> TYPE: PRT
<213> ORGANISM: Artificial Sequence
<220> FEATURE:
<223> OTHER INFORMATION: Nanobody or Nanobody construct

<400> SEQUENCE: 88

His His His His His His Glu Val Gln Leu Val Glu Ser Gly Gly Gly
 1               5                  10                  15

Ser Val Gln Pro Gly Gly Ser Leu Arg Leu Ser Cys Ala Ala Ser Arg
                20                  25                  30

Ser Ile Gly Arg Leu Asp Arg Met Gly Trp Tyr Arg His Arg Pro Gly
            35                  40                  45

Glu Pro Arg Glu Leu Val Ala Thr Ile Thr Gly Gly Ser Ser Ile Asn
 50                  55                  60

Tyr Gly Asp Ser Val Lys Gly Arg Phe Thr Ile Ser Ile Asp Asn Ser
 65                  70                  75                  80

Lys Asn Thr Val Tyr Leu Gln Met Asn Ser Leu Arg Pro Glu Asp Thr
                 85                  90                  95

Ala Val Tyr Tyr Cys Asn Phe Asn Lys Tyr Val Thr Ser Arg Asp Thr
                100                 105                 110

Trp Gly Gln Gly Thr Leu Val Gln Val Ser Ser Ala
            115                 120

<210> SEQ ID NO 89
<211> LENGTH: 123
<212> TYPE: PRT
<213> ORGANISM: Artificial Sequence
<220> FEATURE:
<223> OTHER INFORMATION: Nanobody or Nanobody construct

<400> SEQUENCE: 89

His His His His His His Glu Val Gln Leu Val Glu Ser Gly Gly Gly
 1               5                  10                  15

Ser Val Gln Ala Gly Gly Ser Leu Arg Leu Ser Cys Ala Ala Ser Arg
                20                  25                  30

Ser Ile Gly Arg Leu Asp Arg Met Gly Trp Tyr Arg His Arg Pro Gly
            35                  40                  45

Glu Pro Arg Glu Leu Val Ala Thr Ile Thr Gly Gly Ser Ser Ile Asn
 50                  55                  60

Tyr Gly Asp Ser Val Lys Gly Arg Phe Thr Ile Ser Ile Asp Asn Ser
 65                  70                  75                  80

Lys Asn Thr Val Tyr Leu Gln Met Asn Ser Leu Arg Pro Glu Asp Thr
                 85                  90                  95
```

```
Ala Val Tyr Tyr Cys Asn Phe Asn Lys Tyr Val Thr Ser Arg Asp Thr
            100                 105                 110
Trp Gly Gln Gly Thr Leu Val Gln Val Gly Gly
        115                 120
```